(12) United States Patent
Meyer et al.

(10) Patent No.: US 10,105,372 B2
(45) Date of Patent: Oct. 23, 2018

(54) METHODS OF TREATING OBESITY USING ANTIOXIDANT INFLAMMATION MODULATORS

(75) Inventors: Colin J. Meyer, Southlake, TX (US); Warren Huff, Dallas, TX (US)

(73) Assignee: REATA PHARMACEUTICALS, INC., Irving, TX (US)

( * ) Notice: Subject to any disclaimer, the term of this patent is extended or adjusted under 35 U.S.C. 154(b) by 0 days.

(21) Appl. No.: 13/085,338

(22) Filed: Apr. 12, 2011

(65) Prior Publication Data

US 2011/0281955 A1  Nov. 17, 2011

Related U.S. Application Data

(60) Provisional application No. 61/389,090, filed on Oct. 1, 2010, provisional application No. 61/323,276, filed on Apr. 12, 2010.

(51) Int. Cl.
*A61K 31/122* (2006.01)
*A61P 3/04* (2006.01)
*A61K 31/56* (2006.01)

(52) U.S. Cl.
CPC .................. *A61K 31/56* (2013.01)

(58) Field of Classification Search
CPC ................. A61K 31/56; A61P 3/04
USPC ........................................... 514/661
See application file for complete search history.

(56) References Cited

U.S. PATENT DOCUMENTS

| | | | |
|---|---|---|---|
| 4,395,423 A | 7/1983 | Neumann | 514/519 |
| 6,025,395 A | 2/2000 | Breitner et al. | 514/570 |
| 6,326,507 B1 | 12/2001 | Gribble et al. | 558/415 |
| 6,369,101 B1 | 4/2002 | Carlson | 514/468 |
| 6,552,075 B2 | 4/2003 | Gribble et al. | 514/522 |
| 6,642,217 B2 | 11/2003 | Krasutsky et al. | 514/169 |
| 6,800,639 B2 * | 10/2004 | Giles et al. | 514/300 |
| 6,890,946 B2 | 5/2005 | Nakshatri et al. | 514/400 |
| 6,974,801 B2 * | 12/2005 | Honda et al. | 514/25 |
| 7,176,237 B2 | 2/2007 | Honda et al. | 514/519 |
| 7,288,568 B2 | 10/2007 | Gribble et al. | 514/519 |
| 7,435,755 B2 | 10/2008 | Konopleva et al. | 514/519 |
| 7,678,830 B2 | 3/2010 | Honda et al. | 514/519 |
| 7,714,012 B2 | 5/2010 | Honda et al. | 514/396 |
| 7,795,305 B2 | 9/2010 | Konopleva et al. | 514/510 |
| 7,863,327 B2 * | 1/2011 | Gribble et al. | 514/521 |
| 7,915,402 B2 | 3/2011 | Anderson et al. | 540/519 |
| 7,943,778 B2 | 5/2011 | Jiang et al. | 548/247 |
| 8,034,955 B2 | 10/2011 | Gribble et al. | 548/241 |
| 8,067,394 B2 | 11/2011 | Honda et al. | 514/63 |
| 8,067,465 B2 | 11/2011 | Honda et al. | 514/519 |
| 8,071,632 B2 * | 12/2011 | Jiang et al. | 514/364 |
| 8,088,824 B2 * | 1/2012 | Walling et al. | 514/510 |
| 8,129,429 B2 * | 3/2012 | Sporn et al. | 514/510 |
| 8,338,618 B2 * | 12/2012 | Jiang et al. | 548/250 |
| 8,455,544 B2 * | 6/2013 | Sporn et al. | 514/510 |
| 2002/0042535 A1 | 4/2002 | Gribble et al. | 558/429 |
| 2003/0119732 A1 | 6/2003 | Konopleva et al. | 514/510 |
| 2003/0232786 A1 | 12/2003 | Honda et al. | 514/63 |
| 2003/0236303 A1 | 12/2003 | Gribble et al. | 514/519 |
| 2004/0002463 A1 | 1/2004 | Honda et al. | 514/25 |
| 2005/0208151 A1 | 9/2005 | Hurez et al. | 424/649 |
| 2005/0288363 A1 | 12/2005 | Gribble et al. | 514/463 |
| 2007/0155742 A1 | 7/2007 | Honda et al. | 514/231.2 |
| 2007/0249561 A1 | 10/2007 | Taylor | 514/79 |
| 2008/0220057 A1 | 9/2008 | Gribble et al. | 424/450 |
| 2008/0233195 A1 | 9/2008 | Sporn et al. | 424/486 |
| 2008/0261985 A1 | 10/2008 | Honda et al. | 514/239.5 |
| 2009/0048204 A1 | 2/2009 | Walling et al. | 514/49 |
| 2009/0048205 A1 | 2/2009 | Meyer et al. | 514/49 |
| 2009/0060873 A1 | 3/2009 | Sporn et al. | 424/85.6 |
| 2009/0093447 A1 | 4/2009 | Konopleva et al. | 514/171 |
| 2009/0326063 A1 * | 12/2009 | Sporn et al. | 514/529 |
| 2010/0041904 A1 | 2/2010 | Jiang et al. | 549/456 |
| 2010/0048887 A1 | 2/2010 | Anderson et al. | 540/8 |
| 2010/0048892 A1 | 2/2010 | Anderson et al. | 544/154 |
| 2010/0048911 A1 * | 2/2010 | Jiang et al. | 548/250 |
| 2010/0056777 A1 | 3/2010 | Anderson et al. | 540/520 |
| 2010/0261930 A1 | 10/2010 | Honda et al. | 558/429 |
| 2011/0009363 A1 | 1/2011 | Honda et al. | 514/63 |
| 2011/0196007 A1 | 8/2011 | Honda et al. | 514/400 |
| 2011/0245206 A1 | 10/2011 | Jiang et al. | 514/112 |
| 2011/0245233 A1 | 10/2011 | Anderson et al. | 514/212.04 |
| 2012/0238767 A1 * | 9/2012 | Jiang et al. | 552/6 |

FOREIGN PATENT DOCUMENTS

| | | |
|---|---|---|
| JP | 55-055153 | 4/1980 |
| JP | 2005-314381 | 11/2005 |
| JP | 2008-110962 | 5/2008 |
| JP | 2008-247898 | 10/2008 |
| WO | WO 1999/65478 | 12/1999 |
| WO | WO 2000/73253 | 12/2000 |
| WO | WO 2002/03996 | 1/2002 |

(Continued)

OTHER PUBLICATIONS

Polymethacrylate, "Handbook of Pharmaceutical Excipients", Arther H. Kibbe, 3rd ed., pp. 401-406 (2000).*
Nanjoo Suh et al. [Cancer Research 59, 336-341, Jan. 15, 1999].*
Dorrah Deeb et al (Anticancer Research27:3035-3044(2007).*
Adilson Guilherme et al. (Nature Reviews, Molucular Biology, vol. 9, May 2008, 2008, 892).*
Navaneehan et al. (Clin J Am Soc Nephrol 4: 1565-1574, 2009).*
Hevener et al., "The 2009 stock conference report: Inflammation, obesity and metabolic disease," *Obes Rev.*, 11(9):635-644, 2010.
Thaler et al., "Hypothalamic inflammation and energy homeostasis: Resolving the paradox," *Front. Neuroendocrinol*, 31(1):79-84, 2010.
Zhang et al, "Hypothalamic IKKbeta/NF-kappaB and ER stress link overnutrition to energy imbalance and obesity," *Cell*, 135(1): 61-73, 2008.

(Continued)

*Primary Examiner* — Sabiha N Qazi
(74) *Attorney, Agent, or Firm* — Parker Highlander PLLC

(57) ABSTRACT

The present invention relates to methods of treating and/or preventing obesity comprising the administration of antioxidant inflammation modulators described herein, including for example bardoxolone methyl.

23 Claims, 3 Drawing Sheets

(56) References Cited

FOREIGN PATENT DOCUMENTS

| | | |
|---|---|---|
| WO | WO 2002/032410 | 4/2002 |
| WO | WO 2002/047611 | 6/2002 |
| WO | WO 2002/092768 | 11/2002 |
| WO | WO 2003/059339 | 7/2003 |
| WO | WO 2004/080450 | 3/2004 |
| WO | WO 2004/089357 | 4/2004 |
| WO | WO 2004/099246 | 5/2004 |
| WO | WO 2004/064723 | 8/2004 |
| WO | WO 2004/105517 | 12/2004 |
| WO | WO 2005/042002 | 5/2005 |
| WO | WO 2005/046732 | 5/2005 |
| WO | WO 2006/031293 | 7/2005 |
| WO | WO 2005/113761 | 12/2005 |
| WO | WO 2006/029221 | 3/2006 |
| WO | WO 2007/005879 | 1/2007 |
| WO | WO 2008/000070 | 6/2007 |
| WO | WO 2007/127791 | 11/2007 |
| WO | WO 2008/016095 | 2/2008 |
| WO | WO 2008/064132 | 5/2008 |
| WO | WO 2008/064133 | 5/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/0129548 | 10/2009 |
| WO | WO 2009/146218 | 12/2009 |
| WO | WO 2009/0146218 | 12/2009 |
| WO | WO 2010/011782 | 1/2010 |
| WO | WO 2010/093944 | 8/2010 |
| WO | WO 2011/130302 | 10/2011 |

OTHER PUBLICATIONS

Ghanim et al., "Circulating mononuclear cells in the obese are in a proinflammatory state," *Circulation*, 110:1564-1571, 2004.

Marty et al., "RTA 402 (CDDO0Me) Increases survival of mice administered high doses of cytotoxic chemotherapy," presented by Reata Pharmaceuticals, Nov. 2005.

Zhang et al., "Hypothalamic IKKβ/NF-KB and ER stress link overnutrition to energy imbalance and obesity," *Cell*, 135(1):61-73, 2008.

Search Report of the Eurasian Patent Office for Application No. 201291031 dated May 29, 2013 (in Russian).

Deeb, et al., "CDDO-Me Induces Apoptosis and Inhibits Akt, mTOR and NF-κB Signaling Proteins in Prostate Cancer Cells," *Anticancer Research*, 27:3035-3044, 2007.

Office Action and Search Report in Co-pending Taiwanese Application 098113098, dated Aug. 19, 2013. (Chinese, English translation of Search Report).

Alabran, et al., "Human neuroblastoma cells rapidly enter cell cycle arrest and apoptosis following exposure to C-28 derivatives of the synthetic triterpenoid CDDO," *Cancer Biology & Therapy*, 7(5):709-717, 2008.

Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.

Deeb, et al., "CDDO-Me inhibits proliferation, induces apoptosis, down-regulates Akt, mTOR, NF-κB and NF-κB-regulated antiapoptotic and proangiogenic proteins in TRAMP prostate cancer cells," *J. of Experimental Therapeutics and Oncology*, 7:31-39, 2008.

Heather E. Ferguson, "PPARγ ligands have potent anti-fibrotic activity: mechanism of action and implications for therapy of pulmonary fibrosis," Dissertation, University of Rochester, 2008.

Hughes, et al., "The synthetic triterpenoid CDDO-Im inhibits fatty acid synthase expression and has antiproliferative and proapoptotic effects in human liposarcoma cells," *Cancer Investigation*, 26:118-127, 2008.

Hyer, et al., "Apoptotic activity and mechanism of 2-cyano-3,12-dioxoolean-1,9-dien-28-oic acid and related synthetic triterpenoids in prostate cancer," *Cancer Res.*, 68:2927-2933, 2008.

Liu, et al., "Coordinate regulation of enzyme markers for inflammation and for protection against oxidants and electrophiles," *Proc. Natl. Acad. Sci.*, 105(41):15926-15931, 2008.

Andrew E. Place, "Pre-clincial evaluation of the novel synthetic triterpenoid CDDO-Imidazolide," Thesis, Dartmouth College, May 5, 2004.

Riccioni, et al., "Resistance of acute myeloid leukemic cells to the triterpenoid CDDO-Imidazolide is associated with low caspase-8 and FADD levels," *Leukemia Research*, 32:1244-1258, 2008.

Samudio, et al., "Inhibition of mitochondrial metabolism by methyl-2-cyano-3,12-dioxoolean-1,9-diene-28-oate induces apoptotic or autophagic cell death in chronic myelogenous leukemia cells," *Mol. Cancer Ther.*, 7(5):1130-1139, 2008.

Subba Rao, et al., "Chemical modifications of natural triterpenes—glycyrrhetinic and boswellic acids: evaluation of their biological activity," *Tetrahedron*, 64(51):11541-11548, 2008.

Sun, et al., "Therapeutic potential of synthetic triterpenoids in neuroblastoma," *Cancer Biology & Therapy*, 7(5):720-722, 2008.

To, et al., "The synthetic triterpenoid 2-cyano-3,12-dioxooleana-1,9-dien-28-oic acid-imidazolide alters transforming growth factor β-dependent signaling and cell migration by affecting the cytoskeleton and the polarity complex," *J. Biol. Chem.*, 283:11700-11713, 2008.

Venè, et al., "Glycogen synthase kinase 3β regulates cell death induced by synthetic triterpenoids," *Cancer Res.*, 68:6987-6996, 2008.

Wang, "Differentiating and anti-inflammatory activities of the triterpenoid, CDDO," Thesis, Dartmouth College, May 4, 2001.

Wen, et al., "Naturally occurring pentacyclic triterpenes as inhibitors of glycogen phosphorylase: synthesis, structure-activity relationships, and X-ray crystallographic studies," *J. Med. Chem.*, 51:3540-3554, 2008.

Xu, et al., "Inhibition of the signal transducer and activator of transcription-3 (STAT3) signaling pathway by 4-oxo-l-phenyl-1,4-dihydroquinoline-3-carboxylic acid esters," *J. Med. Chem.*, 51:4115-4121, 2008.

Zou, et al., "c-FLIP downregulation contributes to apoptosis induction by the novel synthetic triterpenoid methyl-2-cyano-3,12-dioxooleana-1,9-dien-28-oate (CDDO-Me) in human lung cancer cells," *Cancer Biology & Therapy*, 6(10):1614-1620, 2007.

Zou, et al., "Coupling of endoplasmic reticulum stress to CDDO-Me-induced up-regulation of death receptor 5 via a CHOP-dependent mechanism involving JNK activation," *Cancer Res.*, 68:7484-7492, 2008.

Bastard et al., "Recent advances in the relationship between obesity, inflammation, and insulin resistance," *Eur. Cytokine Netw.*, 17(1):4-12, 2006.

Hotamisligil et al., "Inflammation and metabolic disorders," *Nature*, 444:860-867, 2006.

Kim et al., "Vascular inflammation, insulin resistance, and reduced nitric oxide production precede the onset of peripheral insulin resistance," *Arterioscler. Thromb. Vasc. Biol.*, 28(11):1982-8, 2008. DOI: 10.1161/ATVBAHA.108.169722. Published online Sep. 4, 2008.

Pergola et al., "Bardoxolone methyl and kidney function in CKD with type 2 diabetes," *The New England Journal of Medicine*, 365(4):327-36, 2011. DOI: 10.1056/NEJMoa1105351. Published online Jun. 24, 2011.

Supplement to Pergola et al., "Bardoxolone methyl and kidney function in CKD with type 2 diabetes," *The New England Journal of Medicine*, 365(4):327-36, 2011. DOI: 10.1056/NEJMoa1105351. Published online Jun. 24, 2011.

"RTA 402, Therapeutic Properties I", slides/handouts presented by Reata Pharmaceuticals, Inc. at private partnering meetings at BioSquare 2006 conference, Mar. 8-10, 2006, Geneva, Switzerland.

"RTA 402, Therapeutic Properties II", slides/handouts presented by Reata Pharmaceuticals, Inc. at private partnering meetings at BIO 2006 conference, Apr. 9-12, 2006, Chicago, Illinois.

(56) References Cited

OTHER PUBLICATIONS

"RTA 402, Therapeutic Properties III", slides presented by Reata Pharmaceuticals, Inc. as a podium presentation at BIO 2006 conference, Apr. 9-12, 2006, Chicago, Illinois.
"RTA 402, Therapeutic Properties IV", slides/handouts presented by Reata Pharmaceuticals, Inc. at private partnering meetings at BioPartnering Europe 2006 conference, Oct. 8-10, 2006, London, England.
"RTA 402, Therapeutic Properties IX", slides/handouts presented by Reata Pharmaceuticals, Inc. at a private partnering meeting at BIO Europe 2007 conference, Nov. 12-14, 2007, Hamburg, Germany.
"RTA 402, Therapeutic Properties V", slides/handouts presented by Reata Pharmaceuticals, Inc. at private partnering meetings at BIO 2007 conference, May 6-9, 2007, Boston Massachusetts.
"RTA 402, Therapeutic Properties VI", slides/handouts presented by Reata Pharmaceuticals, Inc. at private partnering meetings at BIO 2007 conference, May 6-9, 2007, Boston, Massachusetts.
"RTA 402, Therapeutic Properties VII", slides presented by Reata Pharmaceuticals, Inc. as a podium presentation at BIO 2007 conference, May 6-9, 2007, Boston, Massachusetts.
"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.
Abraham and Kappas, "Heme oxygenase and the cardiovascular-renal system," *Free Radic. Biol. Med.*, 39 (1): 1-25, 2005.
Agodoa et al., "Effect of ramipril vs amlodipine on renal outcomes in hypertensive nephrosclerosis," *JAMA*, 285:2719-2728, 2001.
Ahmad et al., "Triterpenoid CDDO-Me blocks the NF-κB pathway by direct inhibition of IKKβ on Cys-179", *J. Biol. Chem.*, 281: 35764-9, 2006.
Ahmad et al., "Triterpenoid CDDO-methyl ester inhibits the Janus-activated kinase-1 (JAK1)→signal transducer and activator of transcription-3 (STAT3) pathway by direct inhibition of JAK1 and STAT3," *Cancer Res.*, 68 (8): 2920-2926, 2008.
Albini and Sporn, "Opinion: the tumour microenvironment as a target for chemoprevention," *Nature Reviews Cancer*, 7: 139-147, 2007.
Ambs et al., "p53 and vascular endothelial growth factor regulate tumor growth of NOS2-expressing human carcinoma cells," *Nat. Med.*, 4(12):1371-1376, 1998.
Andreeff et al., "PPARgamma nuclear receptor as a novel molecular target in leukemias," *2002 Keystone Symposia*, Abstract No. 501, 2002.
Araujo et al., "Systemic rather than local heme oxygenase-1 overexpression improves cardiac allograft outcomes in a new transgenic mouse," *J. Immunol.*, 171 (3): 1572-1580, 2003.
Ardestani et al., "Effects of dexamethasone and betamethasone as COX-2 gene expression inhibitors on rigidity in a rat model of Parkinson's disease," *Indian J. Pharmacol.*, 39:235-9, 2007.
Arkan et al., "IKK-beta links inflammation to obesity-induced insulin resistance," *Nat. Med.*, 11(2):191-198, 2005.
Aschner et al., "Effect of the dipeptidyl peptidase-4 inhibitor sitagliptin as monotherapy on glycemic control in patients with type 2 diabetes," *Diabetes Care*, 29(12): 2632-2637, 2006.
Bach, "Heme oxygenase-1 and transplantation tolerance," *Hum. Immunol.*, 67(6):430-432, 2006.
Baeuerle, "NF-κB: ten years after," *Cell*, 87:13-20, 1996.
Bagasra et al., "Activation of the inducible form of nitric oxide synthase in the brains of patients with multiple sclerosis," *Proc. Natl. Acad. Sci. USA*, 92:12041-12045, 1995.
Baldwin, Jr., "The NF-κB and IκB proteins: new discoveries and insights," *Annu. Rev. Immunol.*, 14:649-681, 1996.
Balkwill et al., "Smoldering and polarized inflammation in the initiation and promotion of malignant disease," *Cancer Cell*, 7 (3): 211-217, 2005.
Bargou et al., "Constitutive nuclear factor κB-RelA activation is required for proliferation and survival of Hodgkin's disease tumor cells," *J. Clin. Invest.*, 100:2961-2969, 1997.
Barkett and Gilmore, "Control of apoptosis by Rel/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.
Beal, "Mitochondria, free radicals, and neurodegeneration," *Curr. Opin. Neurobiol.*, 6:661-666, 1996.
Blann et al., "Circulating endothelial cells: Biomarker of vascular disease," *Thromb Haemost*, 93:228-235, 2005.
Bogdan et al., "Contrasting mechanisms for suppression of macrophage cytokine release by transforming growth factor-beta and interleukin-10," *J. Biol. Chem.*, 267:23301-23308, 1992.
Bore et al., "The anti-inflammatory triterpenoid methyl 2-cyano-3,12-dioxoolean 1,9(11)-dien-28-oate methanol solvate hydrate," Acta Crystallorg C., 58(Pt 3):O199-O200, 2002.
Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.
Buzoni-Gatel et al., "Murine ileitis after intracellular parasite infection is controlled by TGF-beta-producing intraepithelial lymphocytes," *Gastroenterolog*, 120:914-924, 2001.
Cai et al., "Local and systemic insulin resistance resulting from hepatic activation of IKK-beta and NF-kappaB," *Nat. Med.*, 11 (2): 183-190, 2005.
Chauhan and Chauhan, "Oxidative stress in autism," *Pathophysiology*, 13(3):171-181 2006.
Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.
Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.
Cho et al., "The transcription factor NRF2 protects against pulmonary fibrosis," *FASEB Journal*, 18:1-29, 2004.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 13, 2006.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 19, 2006.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Aug. 14, 2006.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Sep. 13, 2006.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Nov. 9, 2006.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Oct. 30, 2007.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 31, 2008.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 6, 2009.
ClinicalTrials.gov study record NCT 00508807, "RTA 402 in advanced solid tumors or lymphoid malignancies conditions: lymphoid malignancies; solid tumors," update of Jul. 27, 2007.

(56) References Cited

OTHER PUBLICATIONS

ClinicalTrials.gov study record NCT 00508807, "RTA 402 in advanced solid tumors or lymphoid malignancies conditions: lymphoid malignancies; solid tumors," update of Jan. 22, 2008.
ClinicalTrials.gov study record NCT 00508807, "RTA 402 in advanced solid tumors or lymphoid malignancies conditions: lymphoid malignancies; solid tumors," update of Aug. 27, 2008.
ClinicalTrials.gov study record NCT 00508807, "RTA 402 in advanced solid tumors or lymphoid malignancies conditions: lymphoid malignancies; solid tumors," update of Jul. 27, 2010.
ClinicalTrials.gov study record NCT 00508807, "RTA 402 in advanced solid tumors or lymphoid malignancies conditions: lymphoid malignancies; solid tumors," update of Oct. 5, 2010.
ClinicalTrials.gov study record NCT 00529113, "Study with gemcitabine and RTA 402 for patients with unresectable pancreatic cancer," update of Sep. 13, 2007.
ClinicalTrials.gov study record NCT 00529113, "Study with gemcitabine and RTA 402 for patients with unresectable pancreatic cancer," update of Mar. 10, 2008.
ClinicalTrials.gov study record NCT 00529113, "Study with gemcitabine and RTA 402 for patients with unresectable pancreatic cancer," update of Jun. 12, 2008.
ClinicalTrials.gov study record NCT 00529113, "Study with gemcitabine and RTA 402 for patients with unresectable pancreatic cancer," update of Dec. 1, 2010.
ClinicalTrials.gov study record NCT 00529438, "RTA 402 in patients with advanced solid tumors or lymphoid malignancies conditions: advanced solid tumors; lymphoid malignancies," update of Sep. 13, 2007.
ClinicalTrials.gov study record NCT 00529438, "RTA 402 in patients with advanced solid tumors or lymphoid malignancies conditions: advanced solid tumors; lymphoid malignancies," update of Apr. 21, 2008.
ClinicalTrials.gov study record NCT 00529438, "RTA 402 in patients with advanced solid tumors or lymphoid malignancies conditions: advanced solid tumors; lymphoid malignancies," update of Dec. 21, 2008.
ClinicalTrials.gov study record NCT 00535314, "Study of two dose levels of RTA 402 in patients with advanced malignant melanoma condition: malignant melanoma," update of Sep. 25, 2007.
ClinicalTrials.gov study record NCT 00535314, "Study of two dose levels of RTA 402 in patients with advanced malignant melanoma condition: malignant melanoma," update of Dec. 10, 2007.
ClinicalTrials.gov study record NCT 00550849, "Study to assess the safety, tolerability, and pharmacodynamics of RTA 402 in patients with hepatic dysfunction condition: liver disease," update of Oct. 29, 2007.
ClinicalTrials.gov study record NCT 00550849, "Study to assess the safety, tolerability, and pharmacodynamics of RTA 402 in patients with hepatic dysfunction condition: liver disease," update of Nov. 6, 2007.
ClinicalTrials.gov study record NCT 00664027, "Phase IIa trial to determine the effects of bardoxolone methyl on renal function in patients with diabetic nephropathy condition: diabetic nephropathy," update of Apr. 21, 2008.
ClinicalTrials.gov study record NCT 00664027, "Phase IIa trial to determine the effects of bardoxolone methyl on renal function in patients with diabetic nephropathy condition: diabetic nephropathy," update of Aug. 17, 2008.
ClinicalTrials.gov study record NCT 00664027, "Phase IIa trial to determine the effects of bardoxolone methyl on renal function in patients with diabetic nephropathy condition: diabetic nephropathy," update of Feb. 18, 2009.
ClinicalTrials.gov study record NCT 00664027, "Phase IIa trial to determine the effects of bardoxolone methyl on renal function in patients with diabetic nephropathy condition: diabetic nephropathy," update of Jun. 25, 2011.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Dec. 18, 2008.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Feb. 11, 2009.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Mar. 26, 2009.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Jun. 4, 2009.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Jan. 6, 2011.
ClinicalTrials.gov study record NCT 01053936, "Phase II Pharmacodynamic Trial to Determine the Effects of Bardoxolone Methyl on eGFR in Patients With Type 2 Diabetes and Chronic Kidney Disease," update of Jan. 21, 2010.
ClinicalTrials.gov study record NCT 01053936, "Phase II Pharmacodynamic Trial to Determine the Effects of Bardoxolone Methyl on eGFR in Patients With Type 2 Diabetes and Chronic Kidney Disease," update of Jul. 6, 2010.
ClinicalTrials.gov study record NCT 01053936, "Phase II Pharmacodynamic Trial to Determine the Effects of Bardoxolone Methyl on eGFR in Patients With Type 2 Diabetes and Chronic Kidney Disease," update of Apr. 12, 2011.
Couch et al., "2-cyano-3,12-dioxooleana-1,9(11)-diene-28-oic acid disrupts microtubule polymerization: a possible mechanism contributing to apoptosis," *Molecular Pharmacology,* 69 (4): 1158-1165, 2006.
Couch et al., "Studies on the reactivity of CDDO, a promising new chemopreventive and chemotherapeutic agent: implications for a molecular mechanism of action ," *Bioorganic and Medicinal Chemistry Letters,* 15 (9): 2215-2219, 2005.
Dezube et al., "Interim results of a phase I trial with a novel orally administered synthetic triterpenoid RTA 402 (CDDO-Me) in patients with solid tumors and lymphoid malignancies," *J. Clin. Oncol.,* 2007 ASCO Annual Meeting Proceedings, 25(18S):14101, 2007.
Dickerson et al., "Elevated serum levels of C-reactive protein are associated with mania symptoms in outpatients with bipolar disorder ," *Prog. Neuropsychopharmacol. Biol. Psychiatry,* 31:952-955, 2007.
Ding et al., "Macrophage deactivating factor and transforming growth factors-$\beta_1$ $\beta_2$ and $\beta_3$, inhibit induction of macrophage nitrogen oxide synthesis by IFN$\gamma^1$," *J. Immunol.,* 145:940-944, 1990.
Dinkova-Kostova et al., "Extremely potent triterpenoid inducers of the phase 2 response: correlations of protection against oxidant and inflammatory stress," *PNAS,* 102:4584-4589, 2005.
Dragnev et al., "Specific chemopreventive agents trigger proteasomal degradation of G1 cyclins: implications for combination therapy," *Clin. Cancer Research,* 10 (7): 2570-2577, 2004.
Duan et al., "Immunosuppressive terpenoids from extracts of *Tripterygium wilfordii,*" *Tetrahedron,* 57 (40): 8413-8424, 2001.
Ekmekcioglu et al., "Tumor iNOS predicts poor survival for stage III melanoma patients," *Int. J. Cancer,* 119:861-866, 2006.
Ellies et al., "Mammary tumor latency is increased in mice lacking the inducible nitric oxide synthase," *Int. J. Cancer,* 106:1-7, 2003.
Elliot et al., "The triterpenoid CDDO inhibits expression of matrix metalloproteinase-1, matrix metalloproteinase-13 and Bcl-3 in primary human chondrocytes," *Arthritis Res. Ther.,* 5:R285-R291, 2003.
Elsawa et al., "Preferential Inhibition of Malignant Cell Growth by CDDO in Waldenstrom Macroglobulinemia," *Blood,* 108(11):2528, 2006.

(56) References Cited

OTHER PUBLICATIONS

Finlay et al., "The Effect of A and C Ring Modification of Oleanolic and Ursolic Acid on the Inhibition of Nitric Oxide Formation in Mouse Macrophages," *213th American Chemical Society National Meeting*, Abstract: 084, 1997.

Forstermann, "Janus-faced role of endothelial NO synthase in vascular disease: uncoupling of oxygen reduction from NO synthesis and its pharmacological reversal," *Biol. Chem.*, 387: 1521-1533, 2006.

Gall et al., "Risk factors for development of incipient and overt diabetic nephropathy in patients with non-insulin dependent diabetes mellitus: prospective, observational study," *BMJ*, 314: 783-788, 1997.

Gao et al., "Synthetic Triterpenoids inhibit growth and induce apoptosis in human glioblastoma and neurolastoma cells through inhibition of prosurvival Akt, NF-κB and Notch1 signaling," *J. of Neuro-oncology*, 84 (2): 147-157, 2007.

Ghosh et al., "NF-κB and Rel proteins: evolutionarily conserved mediators of immune response," *Annu Rev Immunol.*, 16:225-260, 1998.

Goldstein et al., "Effect of initial combination therapy with sitagliptin, a dipeptidyl peptidase-4 inhibitor, and metformin on glycemic control in patients with type 2 diabetes," *Diabetes Care*, 30(8):1979-1987, 2007.

Goodman et al., "Heme oxygenase-1 protects against radiocontrast-induced acute kidney injury by regulating anti-apoptotic proteins," *Kidney Int.*, 72 (8): 945-953, 2007.

Guilherme et al., "Adipocyte dysfunctions linking obesity to insulin resistance and type 2 diabetes," *Nat. Rev. Mol. Cell Biol.*, 9 (5): 367-377, 2008.

Guttridge et al., "NF-kappaB controls cell growth and differentiation through transcriptional regulation of cyclin D1," *Mol. Cell. Biol.*, 19 (8): 5785-5799, 1999.

Habeos et al., "Simvastatin activates Keap1/Nrf2 signaling in rat liver," *J. Mol Med.*, 86(11):1279-85, 2008.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Han et al., "CDDO-Imidazolide inhibits growth and survival of c-Myc-induced mouse B cell and plasma cell neoplasms," *Molecular Cancer*, 5:22, 2006.

Hanson et al., "Theories of schizophrenia: a genetic-inflammatory-vascular synthesis," *BMC Medical Genetics*, 6: 7, 2005.

Hansson and Anton, "Function and morphology of the antennal lobe: new developments," *Annu. Rev. Entomol.*, 45, 203-231, 2006.

Hinz et al., "NF-kappaB function in growth control: regulation of cyclin D1 expression and G0/G1-to-S-phase transition," *Mol. Cell. Biol.*, 19 (4): 2690-2698, 1999.

Honda et al., "A novel dicyanotriterpenoid, 2-cyano-3,12-dioxooleanan-1,9(11)-dien-28-onitrile, active at picomolar concentrations for inhibition of nitric oxide production," *Bioorganic & Medicinal Chemistry Letters*, 12:1027-1030, 2002.

Honda et al., "Design and synthesis of 23,24-dinoroleanolic acid derivatives, novel triterpenoid-steroid hybrid molecules," *J. Org. Chem.*, 63:4846-4849, 1998.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "New synthetic oleanane and ursane triterpenoids as inhibitors of nitric oxide production in mouse macrophages," *The Fifth Chemical Congress of North America*, Cancun, Mexico, Abstract 552 and slides for oral presentation, Nov. 1997.

Honda et al., "Novel synthetic oleanane and ursane triterpenoids with various enone functionalities in ring A as inhibitors of nitric oxide production in mouse macrophages," *J. of Medicinal Chemistry*, 43 (9): 1866-1877, 2000.

Honda et al., "Novel synthetic oleanane triterpenoids: a series of highly active inhibitors of nitric oxide production in mouse macrophages," *Bioorg Med Chem Lett*, 9(24):3429-3434, 1999.

Honda et al., "Synthetic oleanane and ursane triterpenoids with modified rings A and C: A series of highly active inhibitors of nitric oxide production in mouse macrophages," *J. Med. Chem*, 43:4233-4246, 2000.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Hotamisligil, "Inflammation and metabolic disorders," *Nature*, 444 (7121): 860-867, 2006.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ikeda et al., "Triterpenoid CDDO-Im downregulates PML/RAR αexpression in acute promyelocytic leukemia cell," *Cell Death and Differentiation*, 12 (5): 523-531, 2005.

Inoue et al., "CDDO induces apoptosis via the intrinsic pathway in lymphoid cells," *Leukemia*, 18 (5): 948-952, 2004.

International Search Report and Written Opinion issued in PCT/US2011/032156, dated Nov. 18, 2011.

International Search Report and Written Opinion issued in PCT/US2009/030771, dated Apr. 9, 2009.

Ishikawa et al., "Heme oxygenase-1 inhibits atherogenesis in Watanabe heritable hyperlipidemic rabbits," *Circulation*, 104 (15): 1831-1836, 2001.

Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Ji et al., "The synthetic triterpenoid CDDO-imidazolide induces monocytic differentiation by activating the Smad and ERK signaling pathways in HL60 leukemia cells," *Molecular Cancer Therapeutics*, 5 (6): 1452-1458, 2006.

Johansen et al., "Pharmacology and preclinical pharmacokinetics of the triterpenoid CDDO methyl ester," *Proc. Amer. Assoc. Cancer Res.*, 44:1728, 2003.

Joyce et al., "Integration of Rac-dependent regulation of cyclin D1 transcription through a nuclear factor-kappaB-dependent pathway," *J. Biol., Chem.*, 274 (36): 25245-25249, 1999.

Kaltschmidt et al., "Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.

Kansanen et al., "Regulation of Nrf2-dependent gene expression by 15-deoxy-Delta12,14-prostaglandin J2," *Free Radic. Biol. Med.*, 47(9):1310-7, 2009.

Karin, "Nuclear factor-kappaB in cancer development and progression," *Nature*, 441:431-436, 2006.

Kawakami et al., "A comparative study of nitric oxide, glutathione, and glutathione peroxidase activities in cerebrospinal fluid from children with convulsive diseases/children with aseptic meningitis," *Brain Dev.*, 28 (4): 243-246, 2006.

(56) References Cited

OTHER PUBLICATIONS

Kendall-Tackett, "Inflammation, cardiovascular disease, and metabolic syndrome as sequelae of violence against women: the role of depression, hostility, and sleep disturbance," *Trauma Biolence Abuse,* 8 (2): 117-126, 2007.

Khan et al., "A dichotomous role for nitric oxide during acute Toxoplasma gondii infection in mice," *Proc. Natl. Acad. Sci. USA,* 94:13955-13960, 1997.

Kim et al., "An inducible pathway for degradation of FLIP protein sensitizes tumor cells to TRAIL-induced apoptosis," *J. of Biological Chemistry,* 277 (25): 22320-22329, 2002.

Kim et al., "Capasase-3 activation is involved in apoptosis induced by a synthetic triterpenoid in Non-small cell lung cancer (NSCLC) cells," *Proc. Amer. Assoc. Cancer Res.,* 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," *Molecular Cancer Therapeutics,* 1:177-184, 2002.

Kobayashi and Yamamoto, "Molecular mechanisms activating the Nrf2-Keap 1 pathway of antioxidant gene regulation," *Antioxid. Redox. Signal.,* 7:385-394, 2005.

Kobayashi et al., "The antioxidant defense system Keap1-Nrf2 comprises a multiple sensing mechanism for responding to a wide range of chemical compounds," *Mol. Cell Biol.,* 29(2):493-502, 2009.

Konopleva et al., "Activation of nuclear transcription factor PPARgamma by the novel triterpenoid CDDO as targeted therapy in breast cancer," *2002 Keystone Symposium,* Abstract No. 539, 2002.

Konopleva et al., "Mechanisms and Activity of PPARgamma-Active Triterpenoids CDDO and CDDO-Me in Leukemias," *Blood,* 106:2460, 2005.

Konopleva et al., "Novel synthetic triterpenoid CDDO-Me: potent antiproliferative, proapoptotic and differentiating agent in AML," *Blood,* 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood,* 94(Suppl 1):479a, Abstract #2140, 1999.

Konopleva et al., "Novel triterpenoid CDDO-Me is a potent inducer of apoptosis and differentiation in acute myelogenous leukemia," *Blood,* 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.,* 3:1249-1262, 2004.

Konopleva et al., "PPARγ nuclear receptor as a novel therapeutic target in AML," *Proc. of the AACR,* ,42, Abstract #4458, 2001.

Konopleva et al., "PPARgamma Ligand CDDO Induces Apoptosis in Leukemias Via Multiple Apoptosis Pathways," *Abstracts of the 44th Annual Meeting of the American Society of Hematology,* Abstract No. 2209, 2002.

Konopleva et al., "PPARgamma Ligands Are Potent Inducers of Apoptosis in Leukemias and Lymphomas," *American Society of Hematology 43rd Annual Meeting and Exposition,* Abstract No. 501, 2001.

Konopleva et al., "PPARgamma Nuclear Receptor as a Novel Molecular Target in Leukemia Therapy," *Proc. Amer. Assoc. Cancer Res.,* 43:4730, 2002.

Konopleva et al., "Suppression of ERK Activation is Required for Triterpenoid Methyl-CDDO-Induced Apoptosis in AML," *Blood,* 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.,* 5:317-328, 2006.

Konopleva et al., "Synthetic triterpenoid CDDO as a novel therapy for resistant breast cancer," *Proc. Amer. Assoc. Cancer Res.,* 44:2726, 2003.

Konopleva et al., "The novel triterpenoid CDDO-Me suppresses MAPK pathways and promotes p38 activation in acute myeloid leukemia cells," *Leukemia,* 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.,* 64:7927-7935, 2004.

Konopleva et al., "Triterpenoid methyl-CDDO s a potent inducer of apoptosis in CD34+ AML progenitor cells via activation of SAPK pathways and inhibition of MAPK cascades," *Blood,* 104:2533, 2004.

Korovin and Tkachev, "Synthesis of quinoxalines fused with triterpenes, ursolic acid and betulin derivatives," *Russian Chemical Bulletin,* (Translation of Izvestiya Akademii Nauk, Seriya Khimicheskaya), 20 (2): 304-310, 2001.

Koschmieder et al. "CDDO induces granulocytic differentiation of myeloid leukemic blasts through translational up-regulation of p42 CCAAT enhancer-binding protein alph," *Blood,* 110 (10): 3695-3705, 2007.

Kress et al., "Triterpenoids display single agent activity in a mouse model of CLL/SBL," *Blood,* 108(11):2530, 2006.

Kress et al., "Triterpenoids display single agent anti-tumor activity in a transgenic mouse model of chronic lymphocytic leukemia and small B cell lymphoma," *PLOS ONE,* 6(e559):1-11, 2007.

Kruger et al., "Up-regulation of heme oxygenase provides vascular protection in an animal model of diabetes through its antioxidant and antiapoptotic effects," *J. Pharmacol. Exp. Ther.,*319 (3): 1144-1152, 2006.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.,* 46:2240, 2005.

Lee et al., "Double-stranded RNA induces iNOS gene expression in Schwann cells, sensory neuronal death, and peripheral nerve demyelination," *Glia,* 55(7): 712-722, 2007.

Lencz et al., "Converging evidence for a pseudoautosomal cytokine receptor gene locus in schizophrenia," *Mol. Psychiatry,* 12 (6): 572-580, 2007.

Leonard et al., "Expression of nitric oxide synthase in inflammatory bowel disease is not affected by corticosteroid treatment," *J. Clin. Pathol.,* 51:750-753, 1998.

Li and Nel, "Role of the Nrf2-mediated signaling pathway as a negative regulator of inflammation: implications for the impact of particulate pollutants on asthma," *Antioxidants & Redox Signaling,* 8:88-98, 2006.

Liby et al., "Novel semisynthetic analogues of betulinic acid with diverse cytoprotective, antiproliferative, and proapoptotic activities," *Mol. Cancer. Ther.,* 6(7): 2113-2119, 2007.

Liby et al., "The rexinoid LG100268 and the synthetic triterpenoid CDDO-methyl amide are more potent than erlotinib for prevention of mouse lung carcinogenesis," *Mol. Cancer Ther.,* 7:1251-1257, 2008.

Liby et al., "The synthetic triterpenoid CDDO-Imidazolide suppresses STAT phosphorylation and induces apoptosis in myeloma and lung cancer cells," *Clinical Cancer Research,* 12 (14 Part 1): 4288-4293, 2006.

Liby et al., "The synthetic triterpenoids CDDO-Methyl ester and CDDO-ethyl amid prevent lung cancer induced by vinyl carbamate in A/J mice," *Cancer Research,* 67 (6): 1-7, 2007.

Liby et al., "The synthetic triterpenoids, CDDO and CDDO-imidazolide, are potent inducers of heme oxygenase-1 and Nrf2/ARE signaling," *Cancer Res.,* 65:4789-4798, 2005.

Liby et al., "Triterpenoids and rexinoids as multifunctional agents for the prevention and treatment of cancer," *Nat. Rev. Cancer,* 7 (5): 357-369, 2007.

Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.,* 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

(56) References Cited

OTHER PUBLICATIONS

Liu et al., "Heme oxygenase-1 (HO-1) inhibits postmyocardial infarct remodeling and restores ventricular function," *FASEB J.*, 20 (2): 207-216, 2006.

Lozano et al., "Losartan reduces microalbuminuria in hypertensive microalbuminuric type 2 diabetics," *Nephrol Dial Transplant*, 16(Suppl 1):85-89, 2001.

Luo et al., "IKK/NF-kappaB signaling: balancing life and death—a new approach to cancer therapy," *J. Clin. Invest.*, 115 (10): 2625-2631, 2005.

Ma et al., "Multiorgan autoimmune inflammation, enhanced lymphoproliferation, and impaired homeostasis of reactive oxygen species in mice lacking the antioxidant-activated transcription factor Nrf2," *Am J Pathol*, 168:1960-1974, 2006.

MacMicking et al., "Altered responses to bacterial infection and endotoxic shock in mice lacking inducible nitric oxide synthase," *Cell*, 81:641-650, 1995.

Maines and Gibbs, "30 some years of heme oxygenase: from a 'molecular wrecking ball' to a 'mesmerizing' trigger of cellular events," *Biochem. Biophys. Res. Commun.*, 338:568-577, 2005.

Mann et al., "Renal outcomes with telmisartan, ramipril, or both, in people at high vascular risk (the ONTARGET study): a multicentre, randomized, double-blind, controlled trial," *Lancet*, 372:547-553, 2008.

Mantovani et al., "Inflammation by remote control," *Nature*, 435:752-753, 2005.

Marrogi et al., "Nitric oxide synthase, cyclooxygenase 2, and vascular endothelial growth factor in the angiogenesis of non-small cell lung carcinoma," *Clinical Cancer Research*, 6:4739-4744, 2000.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.

Minns et al., "A novel triterpenoid induces transforming growth factor beta production by intraepithelial lymphocytes to prevent ileitis," *Gastroenterology*, 127:119-126, 2004.

Mix et al., "A synthetic triterpenoid selectively inhibits the induction of matrix metalloproteinases 1 and 13 by inflammmatory cytokines," *Arthritis Rheum.*, 44:1096-1104, 2001.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Morris et al., "Association of a functional inducible nitric oxide synthase promoter variant with complications in type 2 diabetes," *J. Mol. Med.*, 80 (2): 96-104, 2002.

Morse and Choi, "Heme oxygenase-1: from bench to bedside," *Am. J. Respir. Crit. Care Med.*, 172 (6): 660-670, 2005.

Morse and Choi, "Heme oxygenase-1: the 'emerging molecule' has arrived," *Am. J. Respir. Crit. Care Med.*, 27(1):8-16, 2002.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Na and Surh et al., "Transcriptional regulation via cysteine thiol modification: a novel molecular strategy for chemoprevention and cytoprotection," *Mol. Carcinog.*, 45 (6): 368-380, 2006.

Naik et al., Role of oxidative stress in pathophysiology of peripheral neuropathy and modulation by N-acetyl-L-cysteine in rats, *Eur. J. Pain*, 10 (7): 573-579, 2006.

Nath et al., "Progression of progressive multifocal leukoencephalopathy despite treatment with beta-interferon," *Neurology*, 66(1): 149-150, 2006.

Nath, "Heme oxygenase-1: a provenance for cytoprotective pathways in the kidney and other tissues," *Kidney Int.*, 70, 432-443, 2006.

Nathan and Xie, "Nitric oxide synthases: roles, tolls, and controls," *Cell*, 78:915-918, 1994.

Nathan, "Points of control in inflammation," *Nature*, 420:846-852, 2002.

Nguyen et al., "The Nrf2-antioxidant response element signaling pathway and its activation by oxidative stress," *J. Biol Chem.*, 284(20):13291-5, 2009.

Nichols, "NF-kappaB and reperfusion injury," *Drug News Perspect.*, 17 (2): 99-104, 2004.

Niikura et al., "The effects of synthetic triterpenoids on superficial zone protein synthesis in articular chondrocytes," Abstract, *Orthopedic Research Society*, San Diego, 2007.

Niikura et al., "The effects of synthetic triterpenoids on szp synthesis in articular chondrocytes," Abstract P197, *Osteoarthritis and Cartilage*, 14(Suppl B):S112-S113, 2006.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Osburn et al., "Genetic of pharmacologic amplification of Nrf2 signaling inhibits acute inflammatory liver injury in mice," *Toxicological Sciences*, 104:218-227, 2008.

Pahl, "Activators and target genes of Rel/NF-κB transcription factors," *Oncogene*, 18:6853-6866, 1999.

Pall, "Nitric oxide synthase partial uncoupling as a key switching mechanism for the NO/ONOO-cycle," *Med. Hypoth.*, 69 (4): 821-825, 2007.

Pedersen et al., "The triterpenoid CDDO induces apoptosis in refractory CLL B cells," *Blood*, 100:2965-2972, 2002.

Place et al., "The novel synthetic triterpenoid, CDDO-imidazolide, inhibits inflammatory response and tumor growth in vivo," *Clin. Cancer Res.*, 9:2798-2806, 2003.

Rajakariar et al., "Hematopoietic prostaglandin D2 synthase controls the onset and resolution of acute inflammation through PGD2 and 15-deoxyDelta12 14 PGJ2," *PNAS USA*, 104 (52): 20979-20984, 2007.

Rangasamy et al., "Disruption of Nrf2 enhances susceptibility to severe airway inflammation and asthma in mice," *Journal of Experimental Medicine*, 202:47-59, 2005.

Rayet and Gelinas, "Aberrant rel/nfkb genes and activity in human cancer," *Oncogene*, 18:6938-6947, 1999.

Ross et al., "Breast cancer biomarkers and molecular medicine," *Expert Rev. Mol. Diagn.*, 3(5): 573-585, 2003.

Ross et al., "HER-2/neu testing in breast cancer," *Am. J. Clin. Pathol.*, 120(Suppl):S53-71, 2003.

Rossi et al., "Anti-inflammatory cyclopentenone prostaglandins are direct inhibitors of IkappaB kinase," *Nature*, 403:103-108, 2000.

Ruster et al., "Detection of elevated N epsilon-carboxymethyllysine levels in muscular tissue and in serum of patients with fibromyalgia," *Scand. J.Rheumatol.*, 34 (6): 460-463, 2005.

Ruvolo et al., "The novel triterpenoid methyl-CDDO inhibits Bc12 phosphorylation and potently kolls U937 cells," *Blood*, 94(10), Suppl. 1, Part 1: 280A, abstract #1251, 1999.

Sacerdoti et al., "Heme oxygenase overexpression attenuates glucose-mediated oxidative stress in quiescent cell phase: linking heme to hyperglycemia complications," *Curr. Neurovasc. Res.*, 2(2): 103-111, 2005.

Salvemini et al., "Endogenous nitric oxide enhances prostaglandin production in a model of renal inflammation," *J. Clin. Invest.*, 93(5):1940-1947, 1994.

Salvemini et al., "Nitric oxide activates cyclooxygenase enzymes," *Proc. Natl. Acad. Sci. USA*, 90(15):7240-7244, 1993.

Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

(56) References Cited

OTHER PUBLICATIONS

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: Abstract No. 4693, 2006.

Samudio et al., "The novel triterpenoid CDDOme potently synergizes with inhibition of bc1-2 function to induce apoptosis in AML via disruption of intracellular redox homeostasis," *Proc. Amer. Assoc. Cancer Res.*, 46: Abstract No. 4955, 2005.

Sarchielli et al., "NF-kappaB activity and iNOS expression in monocytes from internal jugular blood of migraine without aura patients during attacks," *Cephalalgia*, 26 (9): 1071-1079, 2006.

Satoh et al., "Activation of the Keap1/Nrf2 pathway for neuroprotection by electrophillic phase II inducers," *PNAS*, 103 (3): 768-773, 2006.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.

Schulz et al., "Nitric oxide, tetrahydrobiopterin, oxidative stress, and endothelial dysfunction in hypertension," *Antioxid. Redox. Sig.*, 10 (6):1115-1126, 2008.

Sengul et al., "Beneficial effect of lisinopril plus telmisartan in patients with type 2 diabetes, microalbuminuria and hypertension," *Diabetes Research and Clinical Practice*, 71:210-219, 2006.

Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.

Shin et al., "NRF2 modulates aryl hydrocarbon receptor signaling: influence on adipogenesis," *Molecular and Cellular Biology*, 27 (20): 7188-7197, 2007.

Shin et al., "Role of Nrf2 in prevention of high-fat diet-induced obesity by synthetic triterpenoid CDDO-imidazolidem" *Eur. J Pharmacol.*, 620(1-3):138-144, 2009.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.

Singh and Evans, "Nitric oxide, the biological mediator of the decade: fact or fiction?" *Eur. Respir. J.*, 10:699-707, 1997.

Singh et al., "Anti-inflammatory activity of oleanolic acid in rats and mice," *J. Pharm.Pharmacol.*, 44:456-458, 1992.

Sjöholm and Nyström, "Inflammation and the etiology of type 2 diabetes," *Diabetes Metab. Res. Rev.*, 22: 4-10, 2006.

Sporn and Roberts, "Peptide growth factors and inflammation, tissue repair, and cancer," *J. Clin. Invest.*, 78:329-332, 1986.

Sporn et al., "Prospects for prevention and treatment of cancer with selective PPARγ modulators (SPARMs)," *Trends in Molecular Medicine*, 7(9):395-400, 2001.

Stacul et al., "Strategies to reduce the risk of contrast-induced nephropathy," *Am J Cardiol*, 98(suppl):59K-77K, 2006.

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.

Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "New triterpenoids as cancer preventive and anti-inflammatory agents," *Proceedings of the American Association for Cancer Research*, Abstract No. 1457, 38: 216, 1997.

Suh et al., "New triterpenoids as cancer preventive and anti-inflammatory agents," Presentation presented at *Proceedings of the American Association for Cancer Research*, 1997.

Suh et al., "Novel triterpenoids suppress inducible nitric oxide synthase (iNOS) and inducible cyclooxygenase (COX-2) in mouse macrophages," *Cancer Research*, 58:717-723, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al., "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," *American Society of Hematology 43rd Annual Meeting and Exposition*, Abstract No. 498, 2001.

Sun et al., "Structure-activity relationships of oleanan- and ursane-type triterpenoids," *Botanical Studies*, 47:339-368, 2006.

Sun et al., "The Synthetic Triterpenoid, CDDO, Suppresses Alloreactive T Cell Responses and Reduces Murine Early Acute Graft-versus-Host Disease Mortality," *Biology of Blood and Marrow Transplantation*, 13 (5): 521-529, 2007.

Sussan et al., "Disruption of Nrf2, a key inducer of antioxidant defenses, attenuates ApoE-mediated atherosclerosis in mice," *PLoS One*, 3 (11): 1-9, 2008.

Tabe et al., "Chromatin-Mediated Transcriptional Activation with Novel Peroxisome Proliferator—Activated Receptor gamma(P-PARgamma) Ligand 2-cyano-1,9-dien-28-oic Acid (CDDO) in Acute Promyelocytic Leukemia Cells," *Abstracts of the 44th Annual Meeting of the American Society of Hematology*, Abstract No. 2191, 2002.

Takahashi et al., "Organ protective role of heme oxygenase-1 against oxidative stress," *Folia Pharmacolgica Japonica*, 130:252-256, 2007. (English translation).

Takahashi et al., "Role of Stress Protein in Organopathy," *Renal and Intestinal Injury*, 30:359-365, 2006. (English Translation).

Thimmulappa et al., "Nrf2 is a critical regulator of the innate immune response and survival during experimental sepsis," *J. Clinical Investigation*, 116 (4): 984-995, 2006.

Thimmulappa et al., "Nrf2-dependent protection from LPS induced inflammatory response and mortality by CDDO-imidazolide," *Biochem. Biophys. Res. Commun.*, 351:883-889, 2006.

Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.

Torres et al., "Inflammation and nitric oxide production in skeletal muscle of type 2 diabetic patients," *Journal of Endocrinology*, 181:419-427, 2004.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

Tsao et al., "DRIP205 co-activator overexpression enhances PPARgamma-mediated differentiation of leukemia cells by CDDO," *Proc. Amer. Assoc. Cancer Res.*, 46: Abstract No. 1855, 2005.

Tsao et al., "Targeted Induction of Apoptosis in Leukemias by PPARgammma Ligation," *American Society of Hematology 43rd Annual Meeting and Exposition*, Abstract No. 2381, 2001.

Tumlin et al., "Pathophysiology of contrast-induced nephropathy," *Am. J. Cardiol.*, 98 (6A): 14K-20K, 2006.

Van Muiswinkel and Kuiperij, "The Nrf2-ARE signaling pathway: promising drug target to combat oxidative stress in neurodegenerative disorders," *Current Drug Target—CNS & Neurological Disorders*, 4:267-281, 2005.

Vannini et al., "The synthetic oleanane triterpenoid, CDDO-methyl ester, is a potent antiangiogenic agent," *Molecular Cancer Therapeutics*, 6 (12 Part 1), 3139-3146, 2007.

Vázquez et al., "Human immunodeficiency virus type 1-induced macrophage gene expression includes the p21 gene, a target for viral regulation," *J. Virol.*, 79:4479-4491, 2005.

(56) References Cited

OTHER PUBLICATIONS

Viberti et al., "Microalbuminuria reduction with valsartan in patients with type 2 diabetes mellitus—A blood pressure-independent effect," *Circulation,* 106:672-678, 2002.

Vilayur and Harris, "Emerging therapies for chronic kidney disease: what is their role?" *Nature Reviews,* 5: 375-383, 2009.

Vincenti et al., "The synthetic triterpenoid TP-222 inhibits RANKL induction of differentiation and MMP-9 gene expression in osteoclasts," Abstract 1385, *American College of Rheumatology Annual Scientific Meeting,* 2006.

Wang et al., "Synthetic triterpenoid CDDO and its derivatives increase ceramides and are cytotoxic to pediatric acute lymphoblastic leukemia cell lines," *Proc. Am. Assoc. Cancer Res.,* 47: 4643, 2006.

Wardle, "Nuclear factor kappaB for the nephrologist," *Nephrol. Dial. Transplant.,* 16(9):1764-8, 2001.

Yao et al., "Cisplatin nephrotoxicity: a review," *Am J Med Sci,* 334(2):115-124, 2007.

Yates et al., "Pharmacodynamic characterization of chemopreventive triterpenoids as exceptionally potent inducers of Nrf2-regulated genes," *Mol. Cancer Ther.,* 6:154-162, 2007.

Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.,* 66 (4): 2488-2494, 2007.

Yoh et al., "Nrf2-deficient female mice develop lupus-like autoimmune nephritis," *Kidney Int.,* 60(4):1343-1353, 2001.

Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.,* 5 (12): 3232-3239, 2006.

Yu and Kensler, "Nrf2 as a target for cancer chemoprevention," *Mutat. Res.,* 591 (1-2): 93-102, 2005.

Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," *Cancer & Biology Therapy,* 5(5):492-497, 2006.

Zapata et al., "CDDO and CDDO-Im Reduce Tumor Burden in a Transgenic Mouse Model of CLL," *Blood,* 104:3477, 2004.

Zapata et al., "Triterpenoids show activity against leukemic cells in a transgenic mouse model of CLL," *Proc. Amer. Assoc. Cancer Res.,* 46: Abstract No. 5179, 2005.

Zhang et al., "Synthetic triterpenoid CDDO as effective therapy for HER2-expressing resistant breast cancer," *Proc. Amer. Assoc. Cancer Res.,* Abstract No. 3799, 2004.

Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.,* 123:380-387, 2004.

Zingarelli et al., "Nuclear factor-κB as a therapeutic target in critical care medicine," *Crit Care Med.,* 31(Suppl):S105-S111, 2003.

Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.,* 64:7570-7578, 2004.

Aggarwal, "Targeting inflammation-induced obesity and metabolic diseases by curcumin and other nutraceuticals," *Annu. Rev. Nutr,* 30:173-199, 2010.

Palsamy and Subramanian, "Resveratrol protects diabetic kidney by attenuating hyperglycemia-mediated oxidative stress and renal inflammatory cytokines via Nrf2-Keap1 signaling," *Biochimica et Biophysica Acta,* 1812(7):719-731, 2011.

Li et al., "Nuclear Factor-kappa B Signaling in Skeletal Muscle Atrophy," *J. Mol. Med. (Berl).,* 86(10):1113-1126, 2008.

\* cited by examiner

FIGS. 1A-C

METHODS OF TREATING OBESITY USING ANTIOXIDANT INFLAMMATION MODULATORS

The present application claims the benefit of priority to U.S. Provisional Applications 61/389,090, filed Oct. 1, 2010, and 61/323,276, filed Apr. 12, 2010, the entire contents of which are incorporated herein by reference in their entireties.

BACKGROUND OF THE INVENTION

I. Field of the Invention

The present invention relates generally to the fields of biology and medicine. More particularly, it concerns methods for the prevention and/or treatment of diseases, such as obesity, with antioxidant inflammation modulators (AIMs).

II. Description of Related Art

Obesity has become a major health problem in the United States and other developed nations. In the United States, 65% of the adult population is considered overweight or obese, and more than 30% of adults meet the criteria for obesity. The World Health Organization has estimated that more than 1 billion adults worldwide are overweight, with 300 million of these considered clinically obese (Hotamisligil, 2006). The incidence of obesity in children is also growing rapidly in many countries. Obesity is a major risk factor for cardiovascular disease, stroke, insulin resistance, type 2 diabetes, liver disease, neurodegenerative disease, respiratory diseases and other severe illnesses, and has been implicated as a risk factor for certain types of cancer including breast and colon cancer. Aside from its impacts on physical health, obesity has significant adverse effects on quality of life and psychological well-being. The incidence of obesity, already high, is likely to grow as a result of increasingly sedentary lifestyles in many countries. In addition, certain widely used psychiatric drugs, notably atypical antipsychotics, are associated with weight gain and increased risk of diabetes. Since these drugs must be used chronically to achieve adequate control of psychiatric symptoms, and treatment compliance in patients with mental disorders is frequently poor, these side effects present both a barrier to compliance and a significant additional health risk to patients.

Although it is well established that weight loss can be achieved through reduced caloric intake and increased physical activity, obesity has continued to be an intractable problem in Western countries, especially in the United States. The discovery of safe and effective drugs to induce weight loss has been a major research goal for decades. However, to date the drugs that have shown efficacy have been burdened with significant side effects or have shown only modest efficacy. For example, amphetamines have been used effectively as appetite suppressants but have a strong risk of dependence along with other side effects. The discovery of leptin, a peptide hormone that plays a major role in appetite regulation, was considered to be a potential breakthrough in the treatment of obesity, but in clinical trials, leptin was not effective. More recently, cannabinoid receptor antagonists were under development as anti-obesity drugs but showed unacceptable psychiatric side effects. Similarly, drugs designed to reduce fat absorption in the digestive tract have been associated with significant gastrointestinal side effects.

Accordingly, there is a significant need for new anti-obesity treatments. In particular, there is a need for anti-obesity treatments with limited side effects that may be safely used in combination with other drugs that are in common use in obese patients, such as antidiabetic drugs, antihypertensive drugs, cholesterol-reducing agents, and insulin. Thus, agents that can be used for the treatment of obesity would represent a significant advance.

SUMMARY OF THE INVENTION

Thus, in accordance with the present invention, there are provided methods of treating overweight or obese subjects with selective activators of the antioxidant transcription factor Nrf2, such as an antioxidant inflammation modulator (AIM) so as to reduce the weight of the subject. In some aspects, there is provided a method of reducing weight in a subject in need thereof comprising administering to the subject an antioxidant inflammation modulator (AIM) in an amount sufficient to reduce the subject's weight. In some aspects, there is provided a method of pt in a subject in need thereof comprising administering to the subject an antioxidant inflammation modulator (AIM) in an amount sufficient to reduce the subject's weight.

In some embodiments, the subject has excess body fat. In some embodiments, the subject is overweight. In some embodiments, the subject's body mass index (BMI) is from 25 kg/m² to 30 kg/m². In some embodiments, the subject is obese or exhibits one of more symptoms of obesity. In some embodiments, the obesity is class I. In some embodiments, the subject's BMI is from 30 kg/m² to 35 kg/m². In some embodiments, the obesity is class II. In some embodiments, the subject's BMI is from 35 kg/m² to 40 kg/m². In some embodiments, the obesity is class III. In some embodiments, the subject's BMI is from 40 kg/m² to 80 kg/m². In some embodiments, the subject is a human subject.

In some variations of one or more of the above embodiments, the method reduces a subject's weight by 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45% 50%, 55%, 60% or 65%. In some variations of one or more of the above embodiments, the method also selectively induces Nrf2 in the subject. In some variations of one or more of the above embodiments, the method also inhibits activation of NF-κB in the subject.

In some variations of one or more of the above embodiments, the AIM is a compound of the formula:

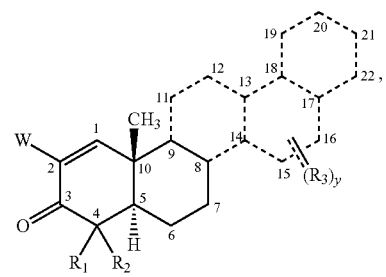

wherein:
W is an electron withdrawing group;
$R_1$ and $R_2$ are each independently:
hydrogen, hydroxy, alkyl$_{(C≤8)}$, substituted alkyl$_{(C≤8)}$, alkenyl$_{(C≤8)}$, substituted alkenyl$_{(C≤8)}$, alkoxy$_{(C≤8)}$ or substituted alkoxy$_{(C≤8)}$; or
$R_1$ and $R_2$ are taken together and are alkanediyl$_{(C≤18)}$, alkenediyl$_{(C≤18)}$, arenediyl$_{(C≤18)}$, alkoxydiyl$_{(C≤18)}$, alkenyloxydiyl$_{(C \leq 18)}$, alkylaminodiyl$_{(C \leq 18)}$, alkenylaminodiyl$_{(C \leq 18)}$, or alkenylaminooxydiyl$_{(C \leq 18)}$;

each $R_3$ is independently:

hydroxy, halo, oxo, amino, hydroxyamino, nitro, imino, cyano, azido, mercapto, or thio;

alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylidene$_{(C \leq 12)}$, alkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, acyloxy$_{(C \leq 12)}$, alkylamino$_{(C \leq 12)}$, dialkylamino$_{(C \leq 12)}$, alkoxyamino$_{(C \leq 12)}$, alkenylamino$_{(C \leq 12)}$, alkynylamino$_{(C \leq 12)}$, arylamino$_{(C \leq 12)}$, aralkylamino$_{(C \leq 12)}$, heteroarylamino$_{(C \leq 12)}$, heteroaralkylamino$_{(C \leq 12)}$, alkylsulfonylamino$_{(C \leq 12)}$, amido$_{(C \leq 12)}$, alkylimino$_{(C \leq 12)}$, alkenylimino$_{(C \leq 12)}$, alkynylimino$_{(C \leq 12)}$, arylimino$_{(C \leq 12)}$, aralkylimino$_{(C \leq 12)}$, heteroarylimino$_{(C \leq 12)}$, heteroaralkylimino$_{(C \leq 12)}$, acylimino$_{(C \leq 12)}$ or a substituted version of any of these groups; or any two $R_3$ in $(R_3)_y$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, or alkenylaminooxydiyl$_{(C \leq 18)}$; and y is from 0 to 8;

or a pharmaceutically-acceptable salt or tautomer thereof.

In some variations of one or more of the above embodiments, the AIM is a compound of the formula:

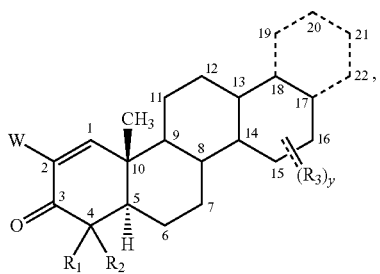

wherein:

W is an electron withdrawing group;

$R_1$ and $R_2$ are each independently:

hydrogen, hydroxy, alkyl$_{(C \leq 8)}$, substituted alkyl$_{(C \leq 8)}$, alkenyl$_{(C \leq 8)}$, substituted alkenyl$_{(C \leq 8)}$, alkoxy$_{(C \leq 8)}$ or substituted alkoxy$_{(C \leq 8)}$; or $R_1$ and $R_2$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, or alkenylaminooxydiyl$_{(C \leq 18)}$;

each $R_3$ is independently:

hydroxy, halo, oxo, amino, hydroxyamino, nitro, imino, cyano, azido, mercapto, or thio;

alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylidene$_{(C \leq 12)}$, alkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, acyloxy$_{(C \leq 12)}$, alkylamino$_{(C \leq 12)}$, dialkylamino$_{(C \leq 12)}$, alkoxyamino$_{(C \leq 12)}$, alkenylamino$_{(C \leq 12)}$, alkynylamino$_{(C \leq 12)}$, arylamino$_{(C \leq 12)}$, aralkylamino$_{(C \leq 12)}$, heteroarylamino$_{(C \leq 12)}$, heteroaralkylamino$_{(C \leq 12)}$, alkylsulfonylamino$_{(C \leq 12)}$, amido$_{(C \leq 12)}$, alkylimino$_{(C \leq 12)}$, alkenylimino$_{(C \leq 12)}$, alkynylimino$_{(C \leq 12)}$, arylimino$_{(C \leq 12)}$, aralkylimino$_{(C \leq 12)}$, heteroarylimino$_{(C \leq 12)}$, heteroaralkylimino$_{(C \leq 12)}$, acylimino$_{(C \leq 12)}$ or a substituted version of any of these groups; or any two $R_3$ in $(R_3)_y$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, or alkenylaminooxydiyl$_{(C \leq 18)}$; and y is from 0 to 8;

or a pharmaceutically-acceptable salt or tautomer thereof.

In some variations of one or more of the above embodiments, the AIM is a compound of the formula:

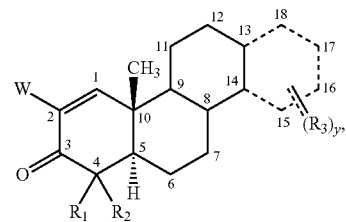

wherein:

W is an electron withdrawing group;

$R_1$ and $R_2$ are each independently:

hydrogen, hydroxy, alkyl$_{(C \leq 8)}$, substituted alkyl$_{(C \leq 8)}$, alkenyl$_{(C \leq 8)}$, substituted alkenyl$_{(C \leq 8)}$, alkoxy$_{(C \leq 8)}$ or substituted alkoxy$_{(C \leq 8)}$; or $R_1$ and $R_2$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, or alkenylaminooxydiyl$_{(C \leq 18)}$;

each $R_3$ is independently:

hydroxy, halo, oxo, amino, hydroxyamino, nitro, imino, cyano, azido, mercapto, or thio;

alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylidene$_{(C \leq 12)}$, alkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, acyloxy$_{(C \leq 12)}$, alkylamino$_{(C \leq 12)}$, dialkylamino$_{(C \leq 12)}$, alkoxyamino$_{(C \leq 12)}$, alkenylamino$_{(C \leq 12)}$, alkynylamino$_{(C \leq 12)}$, arylamino$_{(C \leq 12)}$, aralkylamino$_{(C \leq 12)}$, heteroarylamino$_{(C \leq 12)}$, heteroaralkylamino$_{(C \leq 12)}$, alkylsulfonylamino$_{(C \leq 12)}$, amido$_{(C \leq 12)}$, alkylimino$_{(C \leq 12)}$, alkenylimino$_{(C \leq 12)}$, alkynylimino$_{(C \leq 12)}$, arylimino$_{(C \leq 12)}$, aralkylimino$_{(C \leq 12)}$, heteroarylimino$_{(C \leq 12)}$, heteroaralkylimino$_{(C \leq 12)}$, acylimino$_{(C \leq 12)}$ or a substituted version of any of these groups; or any two $R_3$ in $(R_3)_y$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, or alkenylaminooxydiyl$_{(C \leq 18)}$; and y is from 0 to 7;

or a pharmaceutically-acceptable salt or tautomer thereof.

In some embodiments, the AIM is a compound of the formula:

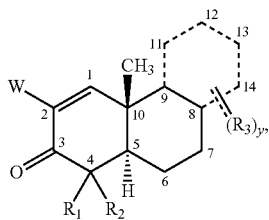

wherein:
W is an electron withdrawing group;
$R_1$ and $R_2$ are each independently:
hydrogen, hydroxy, alkyl$_{(C\le 8)}$, substituted alkyl$_{(C\le 8)}$, alkenyl$_{(C\le 8)}$, substituted alkenyl$_{(C\le 8)}$, alkoxy$_{(C\le 8)}$ or substituted alkoxy$_{(C\le 8)}$; or
$R_1$ and $R_2$ are taken together and are alkanediyl$_{(C\le 18)}$, alkenediyl$_{(C\le 18)}$, arenediyl$_{(C\le 18)}$, alkoxydiyl$_{(C\le 18)}$, alkenyloxydiyl$_{(C\le 18)}$, alkylaminodiyl$_{(C\le 18)}$, alkenylaminodiyl$_{(C\le 18)}$, or alkenylaminooxydiyl$_{(C\le 18)}$;
each $R_3$ is independently:
hydroxy, halo, oxo, amino, hydroxyamino, nitro, imino, cyano, azido, mercapto, or thio;
alkyl$_{(C\le 12)}$, alkenyl$_{(C\le 12)}$, alkynyl$_{(C\le 12)}$, aryl$_{(C\le 12)}$, aralkyl$_{(C\le 12)}$, heteroaryl$_{(C\le 12)}$, heteroaralkyl$_{(C\le 12)}$, acyl$_{(C\le 12)}$, alkylidene$_{(C\le 12)}$, alkoxy$_{(C\le 12)}$, alkenyloxy$_{(C\le 12)}$, alkynyloxy$_{(C\le 12)}$, aryloxy$_{(C\le 12)}$, aralkoxy$_{(C\le 12)}$, heteroaryloxy$_{(C\le 12)}$, heteroaralkoxy$_{(C\le 12)}$, acyloxy$_{(C\le 12)}$, alkylamino$_{(C\le 12)}$, dialkylamino$_{(C\le 12)}$, alkoxyamino$_{(C\le 12)}$, alkenylamino$_{(C\le 12)}$, alkynylamino$_{(C\le 12)}$, arylamino$_{(C\le 12)}$, aralkylamino$_{(C\le 12)}$, heteroarylamino$_{(C\le 12)}$, heteroaralkylamino$_{(C\le 12)}$, alkylsulfonylamino$_{(C\le 12)}$, amido$_{(C\le 12)}$, alkylimino$_{(C\le 12)}$, alkenylimino$_{(C\le 12)}$, alkynylimino$_{(C\le 12)}$, arylimino$_{(C\le 12)}$, aralkylimino$_{(C\le 12)}$, heteroarylimino$_{(C\le 12)}$, heteroaralkylimino$_{(C\le 12)}$, acylimino$_{(C\le 12)}$ or a substituted version of any of these groups; or
any two $R_3$ in $(R_3)_y$ are taken together and are alkanediyl$_{(C\le 18)}$, alkenediyl$_{(C\le 18)}$, arenediyl$_{(C\le 18)}$, alkoxydiyl$_{(C\le 18)}$, alkenyloxydiyl$_{(C\le 18)}$, alkylaminodiyl$_{(C\le 18)}$, alkenylaminodiyl$_{(C\le 18)}$, or alkenylaminooxydiyl$_{(C\le 18)}$; and
y is from 0 to 6;
or a pharmaceutically-acceptable salt or tautomer thereof.

In some variations of one or more of the above embodiments, the AIM is a compound of the formula:

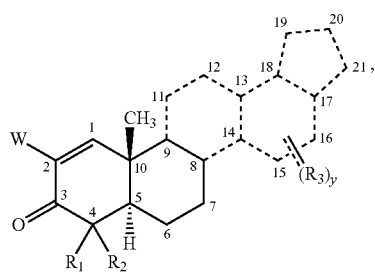

wherein:
W is an electron withdrawing group;
$R_1$ and $R_2$ are each independently:
hydrogen, hydroxy, alkyl$_{(C\le 8)}$, substituted alkyl$_{(C\le 8)}$, alkenyl$_{(C\le 8)}$, substituted alkenyl$_{(C\le 8)}$, alkoxy$_{(C\le 8)}$ or substituted alkoxy$_{(C\le 8)}$; or
$R_1$ and $R_2$ are taken together and are alkanediyl$_{(C\le 18)}$, alkenediyl$_{(C\le 18)}$, arenediyl$_{(C\le 18)}$, alkoxydiyl$_{(C\le 18)}$, alkenyloxydiyl$_{(C\le 18)}$, alkylaminodiyl$_{(C\le 18)}$, alkenylaminodiyl$_{(C\le 18)}$, or alkenylaminooxydiyl$_{(C\le 18)}$;
each $R_3$ is independently:
hydroxy, halo, oxo, amino, hydroxyamino, nitro, imino, cyano, azido, mercapto, or thio;
alkyl$_{(C\le 12)}$, alkenyl$_{(C\le 12)}$, alkynyl$_{(C\le 12)}$, aryl$(c\le 12)$, aralkyl$_{(C\le 12)}$, heteroaryl$_{(C\le 12)}$, heteroaralkyl$_{(C\le 12)}$, acyl$_{(C\le 12)}$, alkylidene$_{(C\le 12)}$, alkoxy$_{(C\le 12)}$, alkenyloxy$_{(C\le 12)}$, alkynyloxy$_{(C\le 12)}$, aryloxy$_{(C\le 12)}$, aralkoxy$_{(C\le 12)}$, heteroaryloxy$_{(C\le 12)}$, heteroaralkoxy$_{(C\le 12)}$, acyloxy$_{(C\le 12)}$, alkylamino$_{(C\le 12)}$, dialkylamino$_{(C\le 12)}$, alkoxyamino$_{(C\le 12)}$, alkenylamino$_{(C\le 12)}$, alkynylamino$_{(C\le 12)}$, arylamino$_{(C\le 12)}$, aralkylamino$_{(C\le 12)}$, heteroarylamino$_{(C\le 12)}$, heteroaralkylamino$_{(C\le 12)}$, alkylsulfonylamino$_{(C\le 12)}$, amido$_{(C\le 12)}$, alkylimino$_{(C\le 12)}$, alkenylimino$_{(C\le 12)}$, alkynylimino$_{(C\le 12)}$, arylimino$_{(C\le 12)}$, aralkylimino$_{(C\le 12)}$, heteroarylimino$_{(C\le 12)}$, heteroaralkylimino$_{(C\le 12)}$, acylimino$_{(C\le 12)}$ or a substituted version of any of these groups; or
any two $R_3$ in $(R_3)_y$ are taken together and are alkanediyl$_{(C\le 18)}$, alkenediyl$_{(C\le 18)}$, arenediyl$_{(C\le 18)}$, alkoxydiyl$_{(C\le 18)}$, alkenyloxydiyl$_{(C\le 18)}$, alkylaminodiyl$_{(C\le 18)}$, alkenylaminodiyl$_{(C\le 18)}$, or alkenylaminooxydiyl$_{(C\le 18)}$; and
y is from 0 to 8;
or a pharmaceutically-acceptable salt or tautomer thereof.

In some variations of one or more of the above embodiments, W is cyano, fluoro or —CF$_3$.

In some variations of one or more of the above embodiments, the AIM is a compound of the formula:

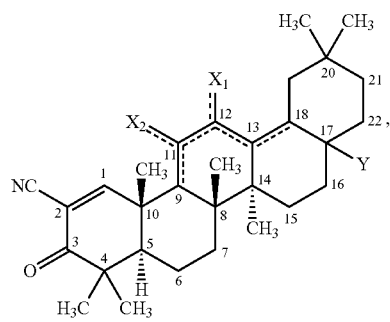

wherein:
$X_1$ and $X_2$ are independently:
hydrogen, hydroxy, halo, oxo, amino, hydroxyamino, nitro, imino, cyano, azido, mercapto, or thio; or
alkyl$_{(C\le 12)}$, alkenyl$_{(C\le 12)}$, alkynyl$_{(C\le 12)}$, aryl$_{(C\le 12)}$, aralkyl$_{(C\le 12)}$, heteroaryl$_{(C\le 12)}$, heteroaralkyl$_{(C\le 12)}$, acyl$_{(C\le 12)}$, alkylidene$_{(C\le 12)}$, alkoxy$_{(C\le 12)}$, alkenyloxy$_{(C\le 12)}$, alkynyloxy$_{(C\le 12)}$, aryloxry$_{(C\le 12)}$, aralkoxy$_{(C\le 12)}$, heteroaryloxy$_{(C\le 12)}$, heteroaralkoxy$_{(C\le 12)}$, acyloxy$_{(C\le 12)}$, alkylamino$_{(C\le 12)}$, dialkylamino$_{(C\le 12)}$, alkoxyamino$_{(C\le 12)}$, alkenylamino$_{(C≤12)}$, alkynylamino$_{(C≤12)}$, arylamino$_{(C≤12)}$, aralkylamino$_{(C≤12)}$, heteroarylamino$_{(C≤12)}$, heteroaralkylamino$_{(C≤12)}$, alkylsulfonylamino$_{(C≤12)}$, amido$_{(C≤12)}$, alkylimino$_{(C≤12)}$, alkenylimino$_{(C≤12)}$, alkynylimino$_{(C≤12)}$, arylimino$_{(C≤12)}$, aralkylimino$_{(C≤12)}$, heteroarylimino$_{(C≤12)}$, heteroaralkylimino$_{(C≤12)}$, acylimino$_{(C≤12)}$ or a substituted version of any of these groups;

Y is hydrogen, hydroxy, halo, amino, hydroxyamino, nitro, cyano, azido, mercapto, alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heteroaralkoxy$_{(C≤12)}$, acyloxy$_{(C≤12)}$, alkylamino$_{(C≤12)}$, dialkylamino$_{(C≤12)}$, alkoxyamino$_{(C≤12)}$, alkenylamino$_{(C≤12)}$, alkynylamino$_{(C≤12)}$, arylamino$_{(C≤12)}$, aralkylamino$_{(C≤12)}$, heteroarylamino$_{(C≤12)}$, heteroaralkylamino$_{(C≤12)}$ or alkylsulfonylamino$_{(C≤12)}$; and or a pharmaceutically-acceptable salt or tautomer thereof.

In some embodiments, the AIM is bardoxolone methyl. In some of the embodiments, at least a portion of the bardoxolone methyl is present as a crystalline form having an X-ray diffraction pattern (CuKα) comprising significant diffraction peaks at about 8.8, 12.9, 13.4, 14.2 and 17.4°2θ. For example, the X-ray diffraction pattern (CuKα) is in some embodiments substantially as shown in FIG. 1A or FIG. 1B. In some of the embodiments, at least a portion of the bardoxolone methyl is present as an amorphous form having an X-ray diffraction pattern (CuKα) with a halo peak at approximately 13.5°2θ, substantially as shown in FIG. 1C, and a $T_g$. In some of the embodiments, the $T_g$ value is in the range of about 120° C. to about 135° C. In some of the embodiments, the $T_g$ value is in the range of about 125° C. to about 130° C.

In some variations of one or more of the above embodiments, the sufficient amount to reduce the subject's weight is a daily dose from about 0.1 mg to about 30 mg of the AIM.

In some variations of one or more of the above embodiments, the AIM is administered orally, intraarterially or intravenously. In some variations of one or more of the above embodiments, the AIM is formulated as a hard or soft capsule or a tablet. In some variations of one or more of the above embodiments, the AIM is formulated as a solid dispersion comprising (i) the compound and (ii) an excipient, for example, the excipient may be a methacrylic acid—ethyl acrylate copolymer. In some embodiments, the ratio of the methacrylic acid—ethyl acrylate copolymer is 1:1.

In some variations of one or more of the above embodiments, the weight of the subject has been measured or will be measured. For example, in some embodiments, the weight of the subject has been measured prior to administering the AIM and will be measured after administering the AIM.

In some variations of one or more of the above embodiments, the BMI of the subject has been measured or will be measured. For example, in some embodiments, the BMI of the subject has been measured prior to administering the AIM and will be measured after administering the AIM.

In some variations of one or more of the above embodiments, the subject also suffers from renal disease, cardiovascular disease, diabetes, autoimmune disease, respiratory disease, neurodegenerative disease, liver disease, infectious disease, or cancer, or has undergone or will undergo organ or tissue transplant.

In some variations of one or more of the above embodiments, the subject does not also suffer from renal disease, cardiovascular disease, diabetes, autoimmune disease, respiratory disease, neurodegenerative disease, liver disease, infectious disease, or cancer, or has not or will not undergo transplant.

In some variations of one or more of the above embodiments, the subject has diabetes. In some variations of one or more of the above embodiments, the subject does not have diabetes. In some variations of one or more of the above embodiments, the subject exhibits one or more symptoms of diabetes. In some variations of one or more of the above embodiments, the subject does not exhibit any symptoms of diabetes. In some variations of one or more of the above embodiments, the subject has been identified as having diabetes. In some variations of one or more of the above embodiments, the subject has been identified as not having diabetes. In some variations of one or more of the above embodiments, the level of a marker of diabetes in the subject has been measured or will be measured.

In some variations of one or more of the above embodiments, the subject has elevated levels of at least one biomarker associated with diabetes, cardiovascular disease, renal disease, fatty liver disease or metabolic syndrome. In some variations of one or more of the above embodiments, the subject does not have elevated levels of at least one biomarker associated with diabetes, cardiovascular disease, renal disease, fatty liver disease or metabolic syndrome. In some variations of one or more of the above embodiments, the subject does not have elevated levels of any biomarker associated with diabetes, cardiovascular disease, renal disease, fatty liver disease or metabolic syndrome. In some embodiments, the biomarker is a marker of insulin resistance, leptin resistance, adiponectin resistance, cardiovascular stress, or renal dysfunction. In some embodiments, the biomarker is a marker of insulin resistance. In some embodiments, the biomarker is fasting glucose or hemoglobin A1c. In some embodiments, the biomarker is a marker of leptin resistance. In some embodiments, the biomarker is a marker of adiponectin resistance. In some embodiments, the biomarker is adiponectin. In some embodiments, the biomarker is a marker of cardiovascular stress. In some embodiments, the biomarker is circulating endothelial cells or C-reactive protein. In some embodiments, the biomarker is circulating endothelial cells. In some embodiments, the biomarker is iNOS-positive circulating endothelial cells. In some embodiments, the biomarker is a marker of renal disease. In some embodiments, the biomarker is serum creatinine. In some embodiments, the biomarker is cystatin C. In some embodiments, the biomarker is uric acid.

In some variations of one or more of the above embodiments, the subject has chronic kidney disease (CKD) or exhibits one or more symptoms of CKD. In some variations of one or more of the above embodiments, the subject does not have chronic kidney disease (CKD). In some variations of one or more of the above embodiments, the subject does not exhibit any symptoms of CKD. In some variations of one or more of the above embodiments, the subject has been identified as having CKD. In some variations of one or more of the above embodiments, the subject has been identified as not having CKD. In some variations of one or more of the above embodiments, the level of a marker of CKD in the subject has been measured or will be measured. In some of the embodiments, the CKD is characterized by a serum creatinine level of 1.3-3.0 mg/DL where the subject is a human female or a serum creatinine level of 1.5-3.0 mg/DL where the subject is a human male. In some embodiments, the CKD is stage 4. In some variations of one or more of the above embodiments, the subject does not have stage 4 chronic kidney disease (CKD).

In some variations of one or more of the above embodiments, the subject has diabetic nephropathy (DN) or exhibits one or more symptoms of DN. In some variations of one or more of the above embodiments, the subject does not have diabetic nephropathy (DN). In some variations of one or more of the above embodiments, the subject does not exhibit any symptoms of DN. In some embodiments, the subject has been identified as having DN. In some embodiments, the subject has been identified as not having DN. In some variations of one or more of the above embodiments, the level of a marker of DN in the subject has been measured or will be measured.

In some variations of one or more of the above embodiments, administering the AIM results in an improvement in estimated glomerular filtration rate (eGFR) of the subject. In some embodiments, the administering reduces the level of serum creatinine in the subject. In some embodiments, the level of serum creatinine in the blood of the subject has been measured or will be measured. In some variations of one or more of the above embodiments, the level of blood urea nitrogen (BUN) in the subject has been measured or will be measured.

In some variations of one or more of the above embodiments, the level of Adiponectin in the blood of the subject has been measured or will be measured.

In some variations of one or more of the above embodiments, the level of Angiotensin II in the subject has been measured or will be measured.

In some variations of one or more of the above embodiments, the subject has insulin resistance or exhibits one or more symptoms of insulin resistance. In some variations of one or more of the above embodiments, the subject does not have insulin resistance. In some variations of one or more of the above embodiments, the subject does not exhibit any symptoms of insulin resistance. In some embodiments, the subject has been identified as having insulin resistance. In some embodiments, the subject has been identified as not having insulin resistance. In some variations of one or more of the above embodiments, the level of a marker of insulin resistance in the subject has been measured or will be measured. In some embodiments, the level of hemoglobin A1c in the subject has been measured or will be measured. In some embodiments, a blood sugar level of the subject has been measured or will be measured. In some embodiments, the administering reduces the level of hemoglobin A1c or fasting blood glucose in the subject. In some embodiments, a fasting glucose level of the subject has been measured or will be measured. In some embodiments, the insulin sensitivity of the subject has been measured or will be measured by a hyperinsulinemic euglycemic clamp test. In some embodiments, a glucose disposal rate (GDR) in the subject has been measured or will be measured.

In some variations of one or more of the above embodiments, the subject has glucose intolerance or exhibits one or more symptoms of glucose intolerance. In some variations of one or more of the above embodiments, the subject does not have glucose intolerance. In some variations of one or more of the above embodiments, the subject does not exhibit any symptoms of glucose intolerance. In some embodiments, the subject has been identified as having glucose intolerance. In some embodiments, the subject has been identified as not having glucose intolerance. In some variations of one or more of the above embodiments, the level of a marker of glucose intolerance in the subject has been measured or will be measured. In some embodiments, the level of hemoglobin A1c in the subject has been measured or will be measured. In some embodiments, a blood sugar level of the subject has been measured or will be measured. In some embodiments, the administering reduces the level of hemoglobin A1c or fasting blood glucose in the subject. In some embodiments, a fasting glucose level of the subject has been measured or will be measured. In some embodiments, the insulin sensitivity of the subject has been measured or will be measured by a hyperinsulinemic euglycemic clamp test. In some embodiments, a glucose disposal rate (GDR) in the subject has been measured or will be measured.

In some variations of one or more of the above embodiments, the subject has cardiovascular disease (CVD) or exhibits one or more symptoms of CVD. In some variations of one or more of the above embodiments, the subject does not have cardiovascular disease (CVD) or does not exhibit any symptoms of CVD. In some variations of one or more of the above embodiments, the subject does not exhibit any symptoms of CVD. In some variations of one or more of the above embodiments, the subject has been identified as having CVD. In some variations of one or more of the above embodiments, the subject has been identified as not having CVD. In some variations of one or more of the above embodiments, the level of a marker of CVD in the subject has been measured or will be measured.

In some variations of one or more of the above embodiments, the number of circulating endothelial cells (CECs) in the blood of the subject has been measured or will be measured. In some embodiments, the CECs are iNOS-positive circulating endothelial cells. In some embodiments, the administering also reduces the level of circulating endothelial cells in the subject. In some embodiments, the administering also reduces the level of hemoglobin A1c or fasting blood glucose in the subject.

In some variations of one or more of the above embodiments, the subject has fatty liver disease (FLD) or exhibits one or more symptoms of FLD. In some variations of one or more of the above embodiments, the subject does not have fatty liver disease (FLD) or does not exhibit any symptoms of FLD. In some variations of one or more of the above embodiments, the subject does not exhibit any symptoms of FLD. In some variations of one or more of the above embodiments, the subject has been identified as having FLD. In some variations of one or more of the above embodiments, the subject has been identified as not having FLD. In some variations of one or more of the above embodiments, the level of a marker of FLD in the subject has been measured or will be measured.

In some variations of one or more of the above embodiments, the subject has been identified as having cancer. In some variations of one or more of the above embodiments, the subject has been identified as not having cancer. In some variations of one or more of the above embodiments, the subject has been identified as having cancer and diabetes. In some variations of one or more of the above embodiments, the subject has been identified as not having cancer and/or not having diabetes.

In some variations of one or more of the above embodiments, if the sufficient amount were administered to a non-obese subject, the non-obese subject's weight would not be reduced significantly.

In some embodiments, the compound is formulated as a hard or soft capsule, a tablet, a syrup, a suspension, a solid dispersion, a wafer, or an elixir. In some variations, the soft capsule is a gelatin capsule. In variations, the compound is formulated as a solid dispersion. In some variations the hard capsule, soft capsule, tablet or wafer further comprises a protective coating. In some variations, the formulated compound comprises an agent that delays absorption. In some variations, the formulated compound further comprises an agent that enhances solubility or dispersibility. In some variations, the compound is dispersed in a liposome, an oil in water emulsion or a water in oil emulsion.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose is 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is administered in a single dose per day. In some embodiments, the pharmaceutically effective amount is administered in two or more doses per day.

In some embodiments, the subject is a primate. In some variations, the primate is a human. In other variations, the subject is a cow, horse, dog, cat, pig, mouse, rat or guinea pig.

In another aspect there is provided a method of reducing a subject's weight comprising administering to the subject a compound of the formula,

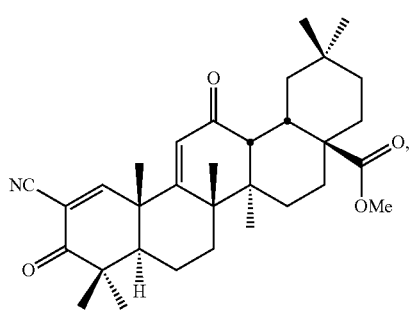

in an amount sufficient to reduce the subject's weight, where the subject has been identified as (i) being overweight or obese; and (ii) not having diabetes.

In another aspect, there is provided a method of reducing a subject's weight comprising administering to the subject a compound of the formula,

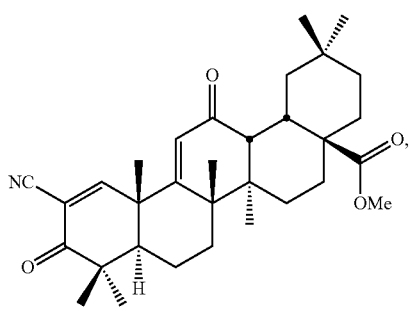

in an amount sufficient to reduce the subject's weight, wherein:
(a) at least a portion of the compound is present as an amorphous form having an X-ray diffraction pattern (CuKα) with a halo peak at approximately 13.5°2θ, substantially as shown in FIG. 1C, and a $T_g$ from about 120° C. to about 135° C.; and
(b) where the subject has been identified as
(i) being overweight or obese; and
(ii) not having diabetes.

In some embodiments, the subject is a human and the amount is a daily dose from 5 mg to 50 mg. In some embodiments, the daily dose is about 10 mg. In some embodiments, the daily dose is about 20 mg. In some embodiments, the daily dose is about 40 mg.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 1A shows unmicronized Form A; FIG. 1B shows micronized Form A; FIG. 1C shows Form B.

DESCRIPTION OF ILLUSTRATIVE EMBODIMENTS

Figure 1:
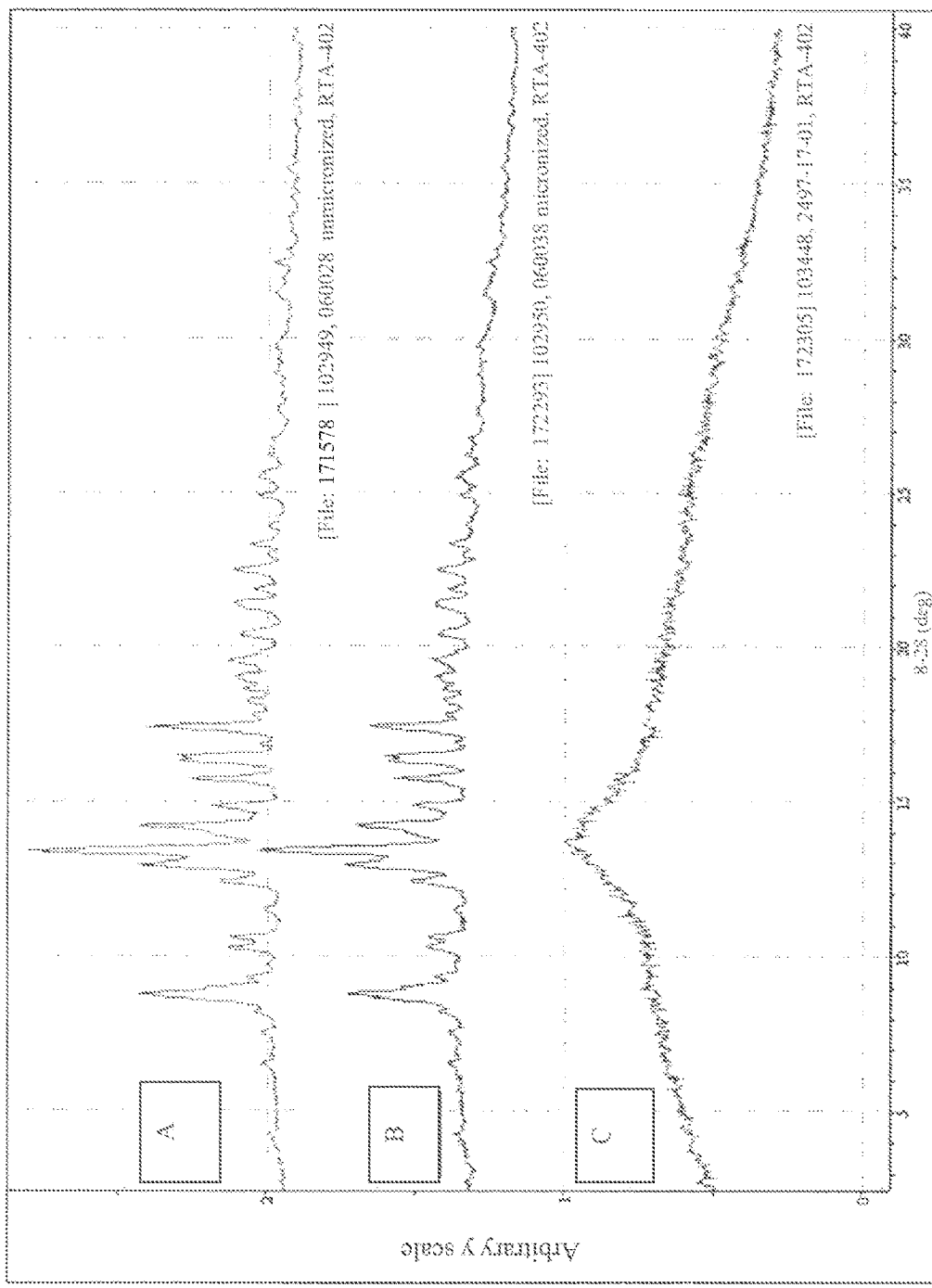
FIGS. 1A-C—X-ray Powder Diffraction (XRPD) Spectra of Forms A and B of RTA 402.

The current invention provides methods of using antioxidant inflammation modulators compounds that may be used, for example, to induce weight loss in patients having established obesity and complications thereof, and have limited side effects. For example, bardoxolone methyl, induces weight loss in clinically obese patients while at the same time improving measures of kidney function, glycemic control and insulin resistance, and cardiovascular disease. This combination of effects represents a significant advance in the state of the art. These and other aspects of the invention are described in greater detail below.

I. Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

The symbol "—" means a single bond, "=" means a double bond, and "≡" means triple bond. The symbol "⋯" represents a single bond or a double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "▬◀" means a single bond where the group attached to the thick end of the wedge is "into the page". The symbol "⌇" means a single bond where the conformation is unknown (e.g., either R or S), the geometry is unknown (e.g., either E or Z) or the compound is present as mixture of conformation or geometries (e.g., a 50%/50% mixture).

When a group "R" is depicted as a "floating group" on a ring system, for example, in the formula:

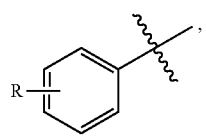

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

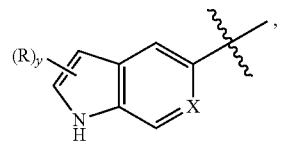

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

When y is 2 and "(R)$_y$" is depicted as a floating group on a ring system having one or more ring atoms having two replaceable hydrogens, e.g., a saturated ring carbon, as for example in the formula:

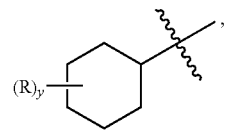

then each of the two R groups can reside on the same or a different ring atom. For example, when R is methyl and both R groups are attached to the same ring atom, a geminal dimethyl group results. Where specifically provided for, two R groups may be taken together to form a divalent group, such as one of the divalent groups further defined below. When such a divalent group is attached to the same ring atom, a spirocyclic ring structure will result.

In the case of a double-bonded R group (e.g., oxo, imino, thio, alkylidene, etc.), any pair of implicit or explicit hydrogen atoms attached to one ring atom can be replaced by the R group. This concept is exemplified below:

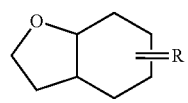

represents

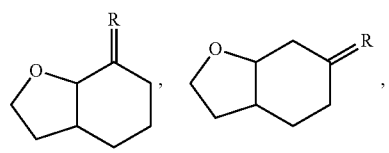

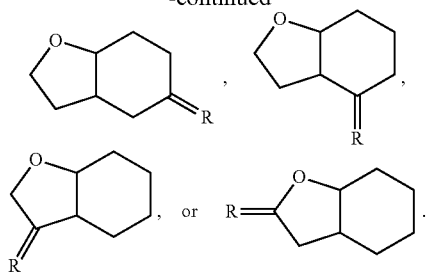

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≤8)}$," is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

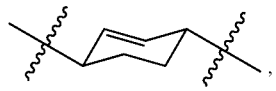 [SMILES: *C1C=CC(*)CC1]

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

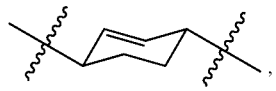 [SMILES: *C1C=CC(*)CC1]

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen.

The groups, —C≡CH, —C≡CCH₃, —C≡CC₆H₅ and —CH₂C≡CCH₃, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH₃)₃, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH₂—, and —C≡CCH(CH₃)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C₆H₄CH₂CH₃ (ethylphenyl), —C₆H₄CH₂CH₂CH₃ (propylphenyl), —C₆H₄CH(CH₃)₂, —C₆H₄CH(CH₂)₂, —C₆H₃(CH₃)CH₂CH₃ (methylethylphenyl), —C₆H₄CH=CH₂ (vinylphenyl), —C₆H₄CH=CHCH₃, —C₆H₄C≡CH, —C₆H₄C≡CCH₃, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C₆H₄F, —C₆H₄Cl, —C₆H₄Br, —C₆H₄I, —C₆H₄OH, —C₆H₄OCH₃, —C₆H₄OCH₂CH₃, —C₆H₄OC(O)CH₃, —C₆H₄NH₂, —C₆H₄NHCH₃, —C₆H₄N(CH₃)₂, —C₆H₄CH₂OH, —C₆H₄CH₂OC(O)CH₃, —C₆H₄CH₂NH₂, —C₆H₄CF₃, —C₆H₄CN, —C₆H₄CHO, —C₆H₄CHO, —C₆H₄C(O)CH₃, —C₆H₄C(O)C₆H₅, —C₆H₄CO₂H, —C₆H₄CO₂CH₃, —C₆H₄CONH₂, —C₆H₄CONHCH₃, and —C₆H₄CON(CH₃)₂.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

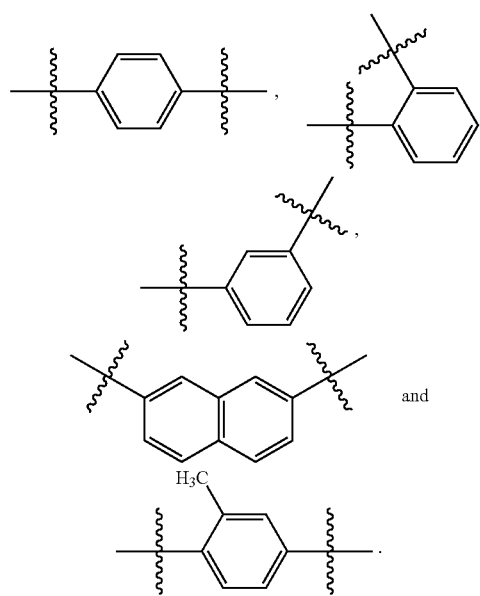

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with two atoms, aromatic carbon atom and/or aromatic nitrogen, as the point of attachment, said carbon atom or nitrogen atom forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. Non-limiting examples of heteroarenediyl groups include:

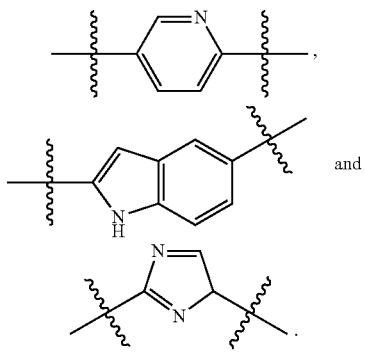

The term "substituted heteroarenediyl" refers to a divalent group, wherein the heteroarenediyl group is attached with two σ-bonds, with an aromatic carbon atom or nitrogen atom as points of attachment, said carbon atom or nitrogen atom forming part of one or more six-membered aromatic ring structure(s), wherein at least one of the ring atoms is nitrogen, oxygen or sulfur, and wherein the divalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)C₆H₄CH₂CH₃, —COC₆H₃(CH₃)₂, and —C(O)CH₂C₆H₅, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH₂CF₃, —CO₂H (carboxyl), —CO₂CH₃ (methylcarboxyl), —CO₂CH₂CH₃, —CO₂CH₂CH₂CH₃, —CO₂C₆H₅, —CO₂CH(CH₃)₂, —CO₂CH(CH₂)₂, —C(O)NH₂ (carbamoyl), —C(O)NHCH₃, —C(O)NHCH₂CH₃, —CONHCH(CH₃)₂, —CONHCH(CH₂)₂, —CON(CH₃)₂, —CONHCH₂CF₃, —CO-pyridyl, —CO-imidazoyl, and —C(O)N₃, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH₂, =CH(CH₂CH₃), and =C(CH₃)₂. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH₃, —OCH₂CH₃, —OCH₂CH₂CH₃, —OCH(CH₃)₂, —OCH(CH₂)₂, —O-cyclopentyl, and —O-cyclohexyl. The term "substituted alkoxy" refers to the group —OR, in which R is a substituted alkyl, as that term is defined above. For example, —OCH₂CF₃ is a substituted alkoxy group.

The term "alkoxydiyl" when used without the "substituted" modifier refers to a non-aromatic divalent group, wherein the alkoxydiyl group is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds in the group's backbone, further having no backbone atoms other than carbon or oxygen and having at least one of each of these atoms in the group's backbone, and no side chains comprising groups other than hydrogen or alkyl. The groups, —O—CH₂CH₂—, —CH₂—O—CH₂CH₂—, —O—CH₂CH₂—O— and —O—CH₂—O— are non-limiting examples of alkoxydiyl groups. The term "substituted alkanyloxydiyl" refers to a divalent group that is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds, and at least one atom independently selected from the group consisting of N, F, Cl, Br, I, Si, P, and S, or having additional oxygen atoms beyond those in the group's backbone. The following groups are non-limiting example of a substituted alkoxydiyl groups: —O—CH$_2$C(OH)H—O— and —O—CH$_2$C(Cl)H—O—.

The terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkenyloxydiyl" when used without the "substituted" modifier refers to a divalent group that is nonaromatic prior to attachment, wherein the alkenyloxydiyl group is attached with two σ-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment, further having no backbone atoms other than carbon or oxygen and having at least one of each of these atoms in the group's backbone, and no side chains comprising groups other than hydrogen or alkyl. The groups, —O—CH═CH—, —O—CH═CHO— and —O—CH═CHCH$_2$— are non-limiting examples of alkenyloxydiyl groups. The term "substituted alkenyloxydiyl" refers to a divalent group that is nonaromatic prior to attachment, wherein the substituted alkenyloxydiyl group is attached with two σ-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment and at least one atom independently selected from the group consisting of N, F, Cl, Br, I, Si, P, and S, or having additional oxygen atoms beyond those in the group's backbone. The following groups are non-limiting example of a substituted alkenyloxydiyl groups: —O—CH═C(OH)—O— and —O—CH═C(Cl)—O—.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, hetero aryl amino, hetero aralkyl amino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylaminodiyl" when used without the "substituted" modifier refers to a non-aromatic divalent group, wherein the alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no double or triple bonds in the group's backbone, further having no backbone atoms other than carbon or nitrogen and having at least one of each of these atoms in the group's backbone, and no side chains comprising groups other than hydrogen or alkyl. The groups, —NH—CH$_2$CH$_2$—, —CH$_2$—NH—CH$_2$CH$_2$—, —NH—CH$_2$CH$_2$—NH— and —NH—CH$_2$—NH— are non-limiting examples of alkylaminodiyl groups. The term "substituted alkylaminodiyl" refers to a divalent group, wherein the substituted alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no carbon-carbon double or triple bonds in the group's backbone, and at least one atom independently selected from the group consisting of O, F, Cl, Br, I, Si, P, and S, or having additional nitrogen atom beyond those in the group's backbone. The following groups are non-limiting example of a substituted alkylaminodiyl groups: —NH—CH$_2$C(OH)H—NH— and —NH—CH$_2$C(Cl)H—CH$_2$—.

The term "alkenylaminodiyl" when used without the "substituted" modifier refers to a divalent group that is nonaromatic prior to attachment, wherein the alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon-nitrogen double that is non-aromatic at least prior to attachment, further having no backbone atoms other than carbon or nitrogen, and no side chains comprising groups other than hydrogen or alkyl. The groups, —NH—CH=CH—, —NH—CH=N— and —NH—CH=CH—NH— are non-limiting examples of alkenylaminodiyl groups. The term "substituted alkenylaminodiyl" refers to a divalent group that is nonaromatic prior to attachment, wherein the substituted alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon nitrogen double bond that is non-aromatic at least prior to attachment and at least one atom independently selected from the group consisting of O, F, Cl, Br, I, Si, P, and S, or having additional nitrogen atoms beyond those in the group's backbone. The following groups are non-limiting example of a substituted alkenylaminodiyl groups: —NH—CH=C(OH)—CH$_2$— and —N=CHC(Cl)H—.

The term "alkenylaminooxydiyl" when used without the "substituted" modifier refers to a divalent group, wherein the alkenylaminooxydiyl group is attached with two σ-bonds, which may become aromatic upon attachment, with two atoms selected from the group consisting of carbon, oxygen and nitrogen as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon nitrogen or oxygen and having at least one of each of these three atoms in the backbone, and no side chains comprising groups other than hydrogen or alkyl. The group —O—CH=N—, is a non-limiting example of an alkenylaminooxydiyl group. The term "substituted alkenylaminooxydiyl" refers to a divalent group that is attached with two σ-bonds, which may become aromatic upon attachment with two atoms selected from the group consisting of carbon, oxygen and nitrogen as points of attachment, further having a linear or branched, cyclo, cyclic or acyclic structure, at least one carbon-carbon double bond or carbon nitrogen double bond that is non-aromatic at least prior to attachment and at least one atom independently selected from the group consisting of F, Cl, Br, I, Si, P, and S, or having one or more additional nitrogen and/or oxygen atoms beyond those in the group's backbone. The following groups are non-limiting example of a substituted alkenylaminooxydiyl groups: —NH—CH=C(OH)—O— and —N=CHC(Cl)H—O—.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_2$H, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "substituted alkylphosphate" refers to the group —OP(O)(OH)(OR), in which R is a substituted alkyl, as that term is defined above.

The term "dialkylphosphate" when used without the "substituted" modifier refers to the group —OP(O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include: —OP(O)(OMe)$_2$, —OP(O)(OEt)(OMe) and —OP(O)(OEt)$_2$. The term "substituted dialkylphosphate" refers to the group —OP(O)(OR)(OR'), in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached via the oxygen atoms to the phosphorous.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)$_2$R, in which R is a substituted alkyl, as that term is defined above. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)$_2$R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)$_2$R, in which R is substituted alkenyl, alkynyl, aryl, aralkyl, heteroaryl and heteroaralkyl, respectively.

The term "alkylsulfinyl" when used without the "substituted" modifier refers to the group —S(O)R, in which R is an alkyl, as that term is defined above. Non-limiting examples of alkylsulfinyl groups include: —S(O)CH$_3$, —S(O)CH$_2$CH$_3$, —S(O)CH$_2$CH$_2$CH$_3$, —S(O)CH(CH$_3$)$_2$, —S(O)CH(CH$_2$)$_2$, —S(O)-cyclopentyl, and —S(O)-cyclohexyl. The term "substituted alkylsulfinyl" refers to the group —S(O)R, in which R is a substituted alkyl, as that term is defined above. For example, —S(O)CH$_2$CF$_3$ is a substituted alkylsulfinyl group.

Similarly, the terms "alkenylsulfinyl", "alkynylsulfinyl", "arylsulfinyl", "aralkylsulfinyl", "heteroarylsulfinyl", and "heteroaralkylsulfinyl" when used without the "substituted" modifier, refers to groups, defined as —S(O)R, in which R is alkenyl, alkynyl, aryl, aralkyl, heteroaryl, and heteroaralkyl, respectively, as those terms are defined above. When any of the terms alkenylsulfinyl, alkynylsulfinyl, arylsulfinyl, aralkylsulfinyl, heteroarylsulfinyl, and heteroaralkylsulfinyl is modified by "substituted," it refers to the group —S(O)R, in which R is substituted alkenyl, alkynyl, aryl, aralkyl, heteroaryl and heteroaralkyl, respectively.

The term "alkylsilyl" when used without the "substituted" modifier refers to a monovalent group, defined as —SiH$_2$R, —SiHRR', or —SiRR'R", in which R, R' and R" can be the same or different alkyl groups, or any combination of two of R, R' and R" can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers to —SiH$_2$R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A single dashed line between two atoms indicates an optional bond. The bond may not be present at all, it may be present as a single bond, or it may be present as a double bound. If an atom is only connected to dashed lines, then the atom itself is optional. It may be present or it may not be present.

A bond shown as a combination of a solid and a dashed line indicates that the bond is either a single bond or a double bond. Thus, for example, the structure

includes the structures

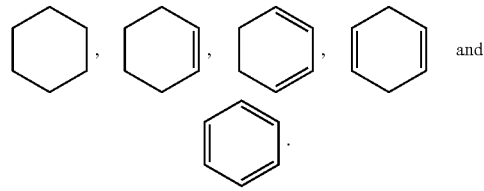

As will be understood by a person of skill in the art, no one such ring atom forms part of more than one double bond.

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $—[—CH_2CH_2—]_n—$, the repeat unit is $—CH_2CH_2—$. The subscript "n" denotes the degree of polymerisation, that is, the number of repeat units linked together. When the value for "n" is left undefined, it simply designates repetition of the formula within the brackets as well as the polymeric nature of the material. The concept of a repeat unit applies equally to where the connectivity between the repeat units extends three dimensionally, such as in metal organic frameworks, cross-linked polymers, thermosetting polymers, etc.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five, and optionally amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds for the Treatment of Obesity

In one aspect of the present disclosure, there are provided methods of reducing weight in a patient in need thereof comprising administering to the subject an antioxidant inflammation modulator (AIM) in an amount sufficient to reduce the patient's weight. These compounds, and molecules containing similar structural features and pharmacology, are known as antioxidant inflammation modulators, or AIMs. A structural feature shared by AIMs is the presence of at least one substructure comprising an alpha, beta-unsaturated carbonyl group with a nitrile group, CF$_3$ group, or other electron-withdrawing group attached to the alpha carbon. These compounds have shown the ability to activate Nrf2, as measured by elevated expression of one or more Nrf2 target genes (e.g., NQO1 or HO-1; Dinkova-Kostova et al., 2005). Further, these compounds are capable of indirect and direct inhibition of pro-inflammatory transcription factors including NF-kappa B and STAT3 (Ahmad et al., 2006; Ahmad et al., 2008). In some aspects, there are provided methods of inhibiting a weight gene in a subject in need thereof comprising administering to the subject an antioxidant inflammation modulator (AIM), including any of the specific compounds disclosed herein, in an amount sufficient to inhibit the weight gene in the subject. In some aspects, there are provided methods of preventing obesity in a subject in need thereof comprising administering to the subject an antioxidant inflammation modulator (AIM), including any of the specific compounds disclosed herein, in an amount sufficient to prevent obesity in the subject. In some aspects, there are provided methods of preventing progression of obesity in a subject in need thereof comprising administering to the subject an antioxidant inflammation modulator (AIM), including any of the specific compounds disclosed herein, in an amount sufficient to prevent progression of obesity in the subject.

In some embodiments, the AIM is a selective activator of the antioxidant transcription factor Nrf2. AIMs for use with this inventions may be represented by the following moiety:

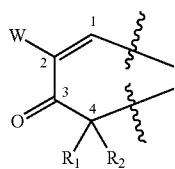

wherein W is nitrile, $CF_3$ or other electron-withdrawing group, and $R_1$ and $R_2$ are as defined above and in the claims below. This pharmacore is found in a variety of synthetic triterpenoids, such as those described by Honda et al. (2000a); Honda et al., (2000b); Honda et al. (2002); and U.S. Patent Application Publications 2009/0326063, 2010/0056777, 2010/0048892, 2010/0048911 and 2010/0041904, each of which is incorporated herein by reference. This pharmacore is also found in a variety of other, non-triterpenoid compounds, for example, tricyclic bis-enones (e.g., TBE-31) as embodied in US Patent Application Publications 2003/0232786 and 2008/0261985, both of which are incorporated by reference herein. Also this pharmacore is also disclosed in U.S. Patent Application Publication 2010/0048887, which is also incorporated by reference herein. Many of these compounds, both the triterpenoid and non-triterpenoid, are highly potent and selective activators of the antioxidant transcription factor Nrf2. Further many of these compounds have been tied to a variety of anti-inflammatory-related activities including, for example, anti-proliferative activities and/or antioxidant activities such as induction of heme oxygenase-1 (HO-1) in vitro and in vivo, induction of CD11b expression, inhibition of iNOS induction, inhibition of COX-2 induction, inhibition of NO production, induction of apoptosis in cancer cells, inhibition of NF-κB, activation of the JNK pathway, and phase 2 induction (elevation of NAD(P)H-quinone oxidoreductase and HO-1). Induction of the Phase 2 response is related to activation of the transcription factor Nrf2, which has been shown to activate the antioxidant response element (ARE) in the promoter region of many antioxidant, anti-inflammatory, and cytoprotective genes, and Phase 2 activation is highly correlated with potent inhibition of NO production in activated macrophages (e.g., Dinkova-Kostova et al., 2005).

One AIM, bardoxolone methyl (BARD), is in advanced clinical trials for the treatment of chronic kidney disease. Data from these and other clinical trials have shown that BARD induces Nrf2 activity in blood cells at therapeutic doses. In the course of these studies the current inventors have identified a clinical scenario in which, following treatment with bardoxolone methyl, overweight or obese patients exhibit a reduction in weight (Table 1).

In certain embodiments, compounds amenable to modification with the above pharmacore include, but are not limited to, triterpenoids (non-limiting examples include argentatin, betulinic acid, lanostane, oleanic acid, ursolic acid, glycyrrhetinic acid, boswellic acid, faradiol, calenduladiol, and moronic acid), saponins (e.g., ginsenoside), avicins, resveratrol, curcumin, gossypol, epigallocatechin, epigallocatechin-3-gallate (EGCG), gossypol, lapachol, other flavonoids (non-limiting examples include quercetin, daidzein, luteolin, coumarin, wogonin and baicalin), dehydroandrosterone (DHEA), cholic acid, deoxycholic acid, ginsenoside (e.g., 20(S)-ginsenoside), silymarin, anthocyanins, avenanthramides, cucurbitacins, aloesin, aloe-emodin, and/or tubeimosides.

Non-limiting examples of triterpenoids that may be used in accordance with the methods of this invention are shown here.

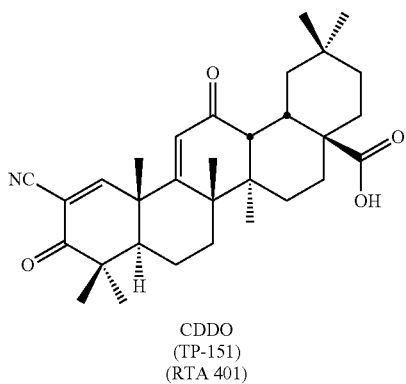

CDDO
(TP-151)
(RTA 401)

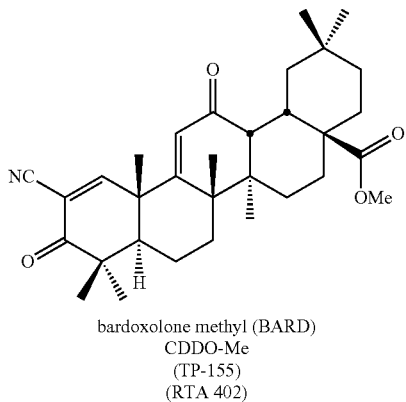

bardoxolone methyl (BARD)
CDDO-Me
(TP-155)
(RTA 402)

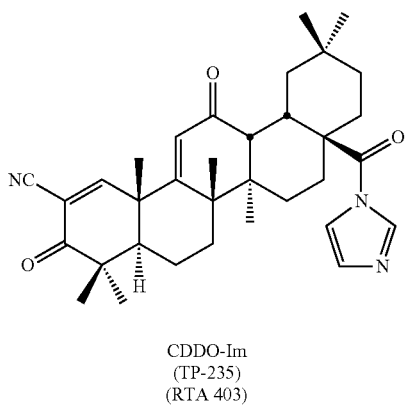

CDDO-Im
(TP-235)
(RTA 403)

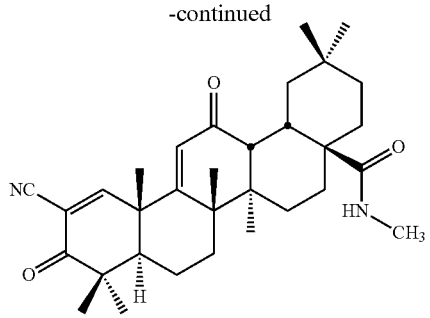
CDDO-MA
(TP-224)
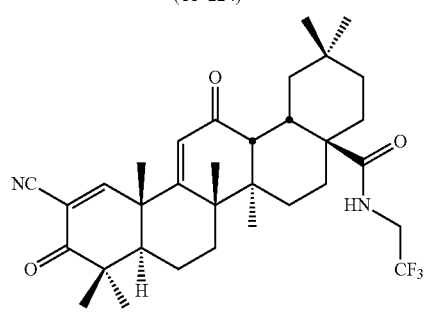
CDDP-TFEA
(TP-500)
(RTA 404)
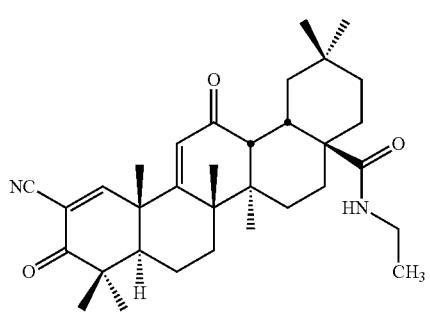
CDDO-EA
(TP-319)
(RTA 405)
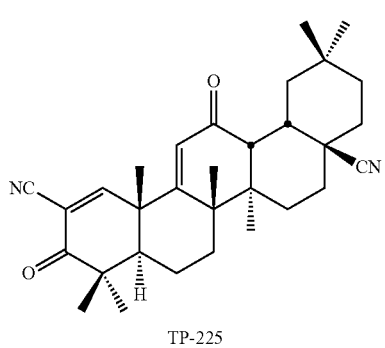
TP-225
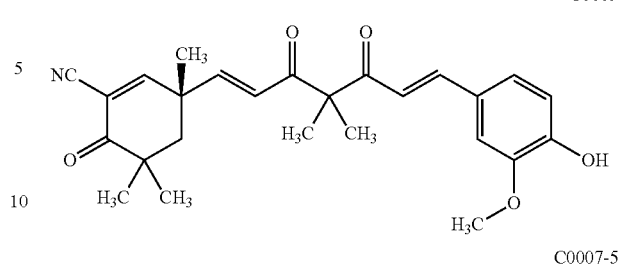
C0009
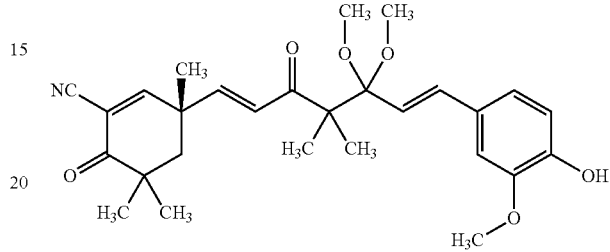
C0007-5
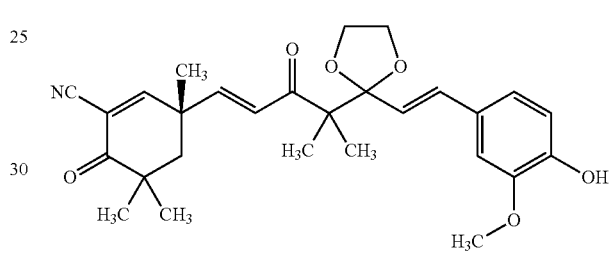
C0010
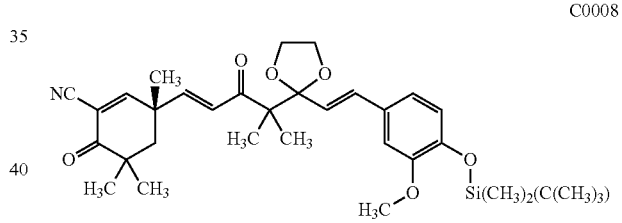
C0008
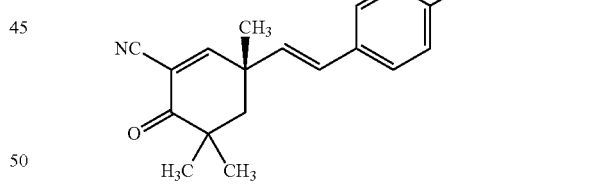
R00142
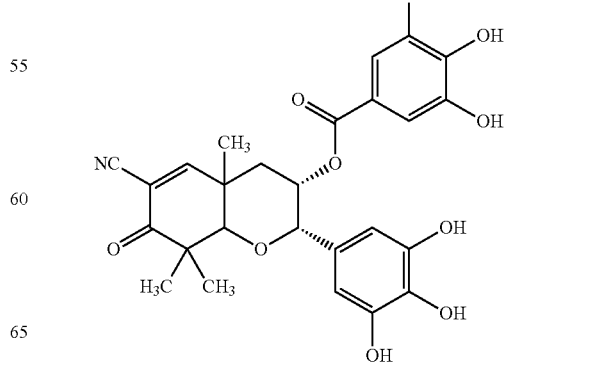
EGCG 1
Non-limiting examples of non-triterpenoid compounds that may be used in accordance with the methods of this invention are shown here.

-continued
EGCG 2
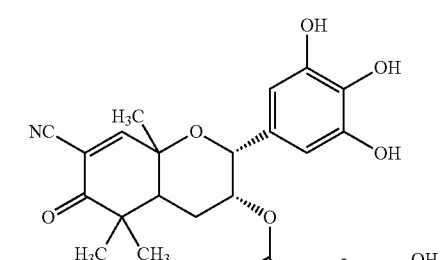
H0001
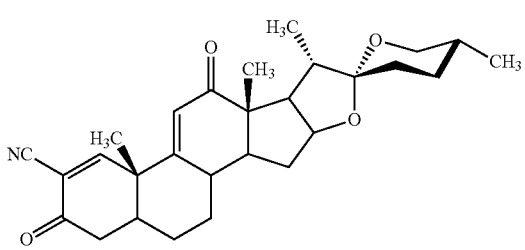
R00141
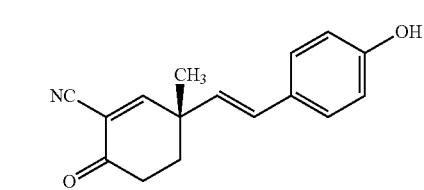
R00142-1
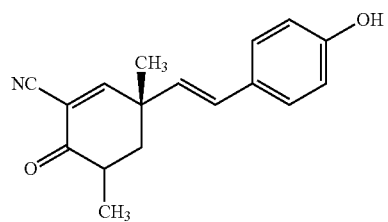
D0018
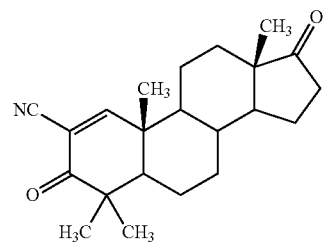
D0017
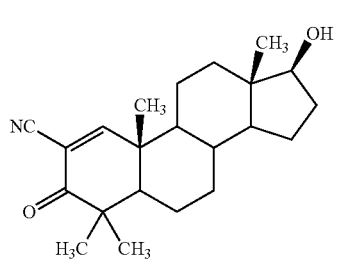
-continued
D0016
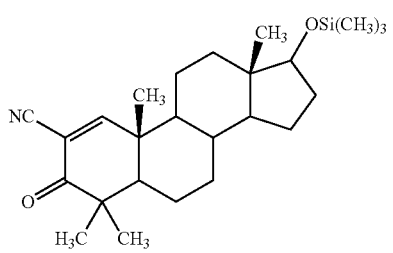
63290
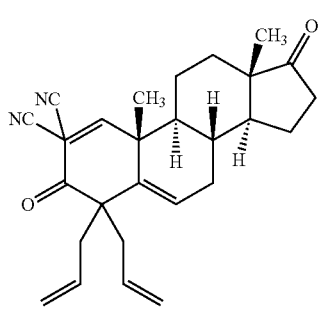
63291
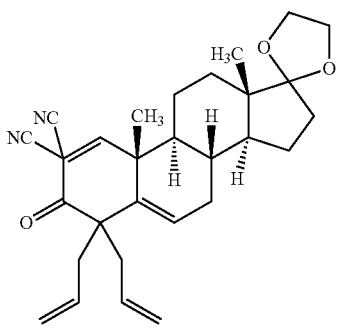
63304
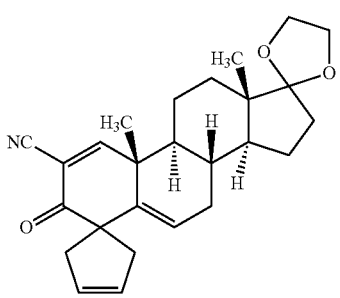
63311
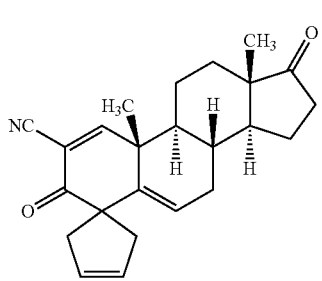

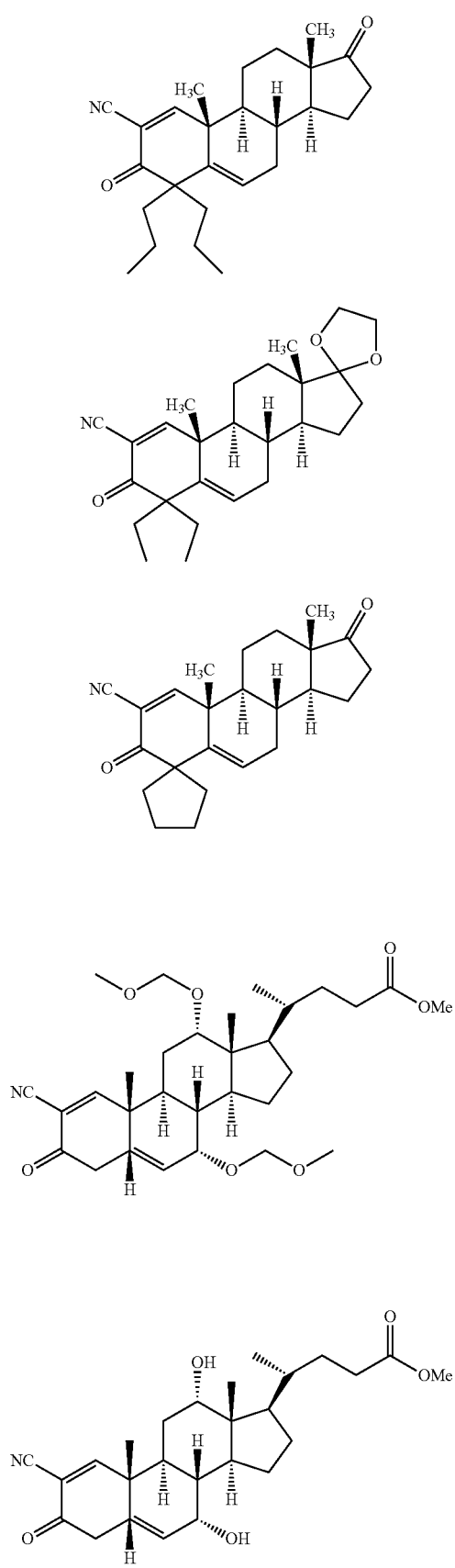

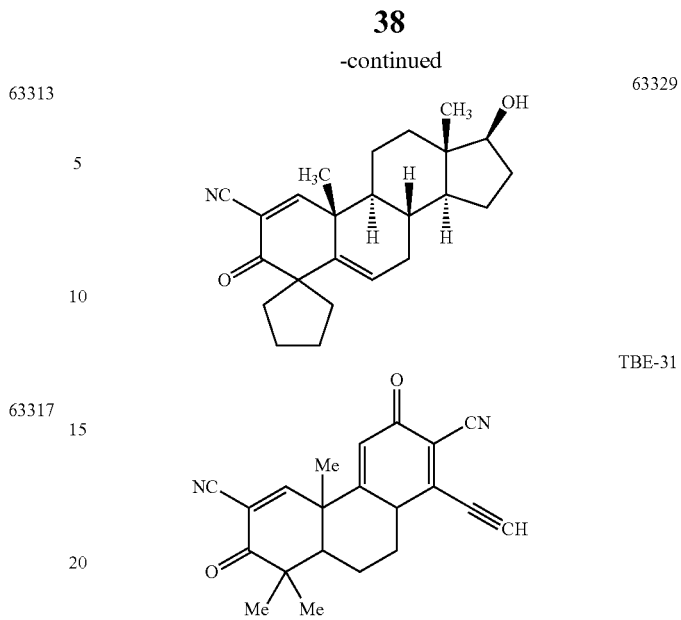

Although some of the most potent and selective known activators of Nrf2 are AIMs, compounds based on other molecular scaffolds have also been reported to activate Nrf2. These include sulforaphane, oltipraz, dimethyl fumarate, statins, cyclopentenone prostaglandins, and NO-donating molecules (see, e.g., Yates et al., 2006; 2009; Habeos et al., 2008; Nguyen et al., 2009; Kansanen et al., 2009; Kobayashi et al., 2009; Gao et al., 2006).

Compounds employed in may be made using the methods described by Honda et al. (2000a); Honda et al., (2000b); Honda et al. (2002); and U.S. Patent Application Publications 2009/0326063, 2010/0056777, 2010/0048892, 2010/0048911, 2010/0041904, 2003/0232786, 2008/0261985 and 2010/0048887, all of which are incorporated by reference herein. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is also incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Polymorphic forms of the compounds of the present invention, e.g., Forms A and B of CDDO-Me, may be used in accordance with the methods of this inventions. Form B displays a bioavailability that is surprisingly better than that of Form A. Specifically the bioavailability of Form B was higher than that of Form A CDDO-Me in monkeys when the monkeys received equivalent dosages of the two forms orally, in gelatin capsules. See U.S. Patent Application Publication 2009/0048204, which is incorporated by reference herein in its entirety.

"Form A" of CDDO-Me (RTA 402) is unsolvated (non-hydrous) and can be characterized by a distinctive crystal structure, with a space group of $P4_3\,2_12$ (no. 96) unit cell dimensions of a=14.2 Å, b=14.2 Å and c=81.6 Å, and by a packing structure, whereby three molecules are packed in helical fashion down the crystallographic b axis. In some embodiments, Form A can also be characterized by X-ray powder diffraction (XRPD) pattern (CuKα) comprising significant diffraction peaks at about 8.8, 12.9, 13.4, 14.2 and 17.4°θ. In some variations, the X-ray powder diffraction of Form A is substantially as shown in FIG. 1A or FIG. 1B.

Unlike Form A, "Form B" of CDDO-Me is in a single phase but lacks such a defined crystal structure. Samples of Form B show no long-range molecular correlation, i.e., above roughly 20 Å. Moreover, thermal analysis of Form B samples reveals a glass transition temperature ($T_g$) in a range from about 120° C. to about 130° C. In contrast, a disordered nanocrystalline material does not display a $T_g$ but instead only a melting temperature ($T_m$), above which crystalline structure becomes a liquid. Form B is typified by an XRPD spectrum (FIG. 1C) differing from that of Form A (FIG. 1A or FIG. 1B). Since it does not have a defined crystal structure, Form B likewise lacks distinct XRPD peaks, such as those that typify Form A, and instead is characterized by a general "halo" XRPD pattern. In particular, the non-crystalline Form B falls into the category of "X-ray amorphous" solids because its XRPD pattern exhibits three or fewer primary diffraction halos. Within this category, Form B is a "glassy" material.

Form A and Form B of CDDO-Me are readily prepared from a variety of solutions of the compound. For example, Form B can be prepared by fast evaporation or slow evaporation in MTBE, THF, toluene, or ethyl acetate. Form A can be prepared in several ways, including via fast evaporation, slow evaporation, or slow cooling of a CDDO-Me solution in ethanol or methanol. Preparations of CDDO-Me in acetone can produce either Form A, using fast evaporation, or Form B, using slow evaporation.

Various means of characterization can be used together to distinguish Form A and Form B CDDO-Me from each other and from other forms of CDDO-Me. Illustrative of the techniques suitable for this purpose are solid state Nuclear Magnetic Resonance (NMR), X-ray powder diffraction (compare FIGS. 1A & B with FIG. 1C), X-ray crystallography, Differential Scanning calorimetry (DSC), dynamic vapor sorption/desorption (DVS), Karl Fischer analysis (KF), hot stage microscopy, modulated differential screening calorimetry, FT-IR, and Raman spectroscopy. In particular, analysis of the XRPD and DSC data can distinguish Form A, Form B, and a hemibenzenate forms of CDDO-Me. See U.S. Patent Application Publication 2009/0048204, which is incorporated by reference herein in its entirety.

Additional details regarding polymorphic forms of CDDO-Me are described in U.S. Patent Application Publication 2009/0048204, PCT Publication WO 2009/023232 and PCT Publication WO 2010/093944, which are both incorporated herein by reference in their entireties.

Non-limiting specific formulations of the compounds disclosed herein include CDDO-Me polymer dispersions. See, for example, PCT Publication WO 2010/093944, which is incorporated herein by reference in its entirety. Some of the formulations reported therein exhibited higher bioavailability than either the micronized Form A or nanocrystalline Form A formulations. Additionally, the polymer dispersion based formulations demonstrated further surprising improvements in oral bioavailability relative to the micronized Form B formulations. For example, the methacrylic acid copolymer, Type C and HPMC-P formulations showed the greatest bioavailability in the subject monkeys. See, for example, PCT Publication WO 2010/093944, which is incorporated herein by reference in its entirety.

Compounds employed in methods of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Compounds employed in methods of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art for use in the indications stated herein.

III. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, and chronic obstructive pulmonary disease is closely associated with the presence of chronic oxidative stress and inflammation, leading to the development of fibrosis and eventual loss of organ function.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases involving oxidative stress and dysregulation of inflammatory processes including cancer, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the above-stated indications or otherwise.

In one aspect, the compounds disclosed herein may be used to function as antioxidant inflammation modulators (AIMs) having potent anti-inflammatory properties that mimic the biological activity of cyclopentenone prostaglandins (cyPGs). In one embodiment, the compounds disclosed herein may be used to control the production of pro-inflammatory cytokines by selectively targeting regulatory cysteine residues (RCRs) on proteins that regulate the transcriptional activity of redox-sensitive transcription factors. Activation of RCRs by cyPGs or AIMs has been shown to initiate a pro-resolution program in which the activity of the antioxidant and cytoprotective transcription factor Nrf2 is potently induced, and the activities of the pro-oxidant and pro-inflammatory transcription factors NF-κB and the STATs are suppressed. This increases the production of antioxidant and reductive molecules (e.g., NQO1, HO-1, SOD1, and/or γ-GCS) and/or decreases oxidative stress and the production of pro-oxidant and pro-inflammatory molecules (e.g., iNOS, COX-2, and/or TNF-α).

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, autoimmune diseases such as rheumatoid arthritis, lupus, and MS, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

A. Obesity

Another aspect of the present disclosure concerns new methods and compounds for the treatment and prevention of obesity. Obesity is a medical condition in which excess body fat has accumulated to the extent that it may have an adverse effect on health. It is typically defined by body mass index (BMI) and may be further evaluated in terms of fat distribution via the waist-hip ratio and total cardiovascular risk factors. BMI is related to both percentage body fat and total body fat.

BMI is calculated by dividing the subject's mass by the square of his or her height (in metric units: kilograms/meters$^2$). The definitions established by the World Health Organization (WHO) in 1997 and published in 2000 are listed below:

| BMI | Classification |
|---|---|
| <18.5 | underweight |
| 18.5-24.9 | normal weight |
| 25.0-29.9 | overweight |
| 30.0-34.9 | class I obesity |
| 35.0-39.9 | class II obesity |
| ≥40.0 | class III obesity |

Obesity increases the risk of many physical and mental conditions. These comorbidities are most commonly shown in metabolic syndrome, a combination of medical disorders which includes: diabetes mellitus type 2, high blood pressure, high blood cholesterol, and high triglyceride levels.

A substantial body of research supports an association between obesity and a chronic, "smoldering" inflammatory state. Obesity is associated with overproduction of inflammatory cytokines and chronic activation of inflammatory signaling pathways, including the NF-kB pathway (Hotamisligil, 2006). Chronic inflammation in adipose tissue is linked with the development of insulin resistance in skeletal muscle (Guilherme et al., 2008). Chronic activation of the NF-κB pathway has been shown to induce insulin resistance and NF-κB inhibition has been proposed as a therapeutic strategy for the treatment of Type 2 diabetes (Arkan et al., 2005; Shoelson et al., 2006).

In a fashion analogous to the development of insulin resistance, obesity has been associated with the development of resistance to the action of leptin. Leptin, a peptide hormone, has complex biological effects but one important site of action is the mediobasal hypothalamus. This structure of the brain is known to exert control over feeding behavior and energy homeostasis. Recently, oxidative stress and activation of the NF-κB pathway in the hypothalamus were shown to be linked to hypothalamic insulin and leptin resistance (Zhang et al., 2008). Activation of the antioxidant transcription factor Nrf2 is known to inhibit NF-κB activity, and Nrf2 activation by a semisynthetic triterpenoid has been reported to inhibit the development of obesity in mice fed on a high-fat diet (Shin et al., 2009).

The effect of Nrf2 activation on body weight in adult humans with established obesity, however, has not been reported. In the course of a clinical trial of bardoxolone methyl (BARD), in patients with chronic kidney disease and Type 2 diabetes, the inventors noted that essentially all patients treated with bardoxolone methyl lost significant amounts of body weight over a two-month period. The primary purpose of the trial was to study the effects of BARD on parameters related to renal function, with secondary endpoints related to glycemic control and cardiovascular disease. Body weight measurements were a routine component of the safety dataset for this trial. Treatment with BARD produced statistically significant improvements in measures of renal function (serum creatinine, estimated glomerular filtration rate, serum phosphorus, blood urea nitrogen, and uricemia), glycemic control (fasting glucose and hemoglobin A1c percentage), and cardiovascular disease (circulating endothelial cells). The ability of BARD to promote weight loss, while simultaneously improving a variety of measures related to obesity-associated diseases, is both fortuitous and unprecedented.

In a clinical trial of bardoxolone methyl in patients having Type 2 diabetes and chronic kidney disease, designed to measure the drug's effect on measures of kidney function, glycemic control, insulin resistance, and cardiovascular disease, clear improvements in all these parameters were noted. See Example 1, below. Patients received 25 mg bardoxolone methyl once per day for 28 days, followed by 75 mg once per day for 28 days. In this study, the protocol stipulated that patient weights were to be taken at baseline (D−1=1 day before initiation of dosing), Day 28, and Day 56. Weight data were available for all but one patient who started the study (a baseline weight was not recorded for this patient). In the remaining patients, 14 of 17 had lost weight at Day 28 (mean weight loss was 1.6% of baseline weight) and 17 of 17 had lost weight at Day 56 (mean weight loss was 3.7% of baseline, with a median of 3.1%). All patients, including the patient who did not have a baseline weight available, lost weight between Day 28 and Day 56. A large majority of these patients was overweight or clinically obese (Mean baseline weight was 101 kg). As shown in Table 1, all but three patients lost more than 2% of their baseline weight between Day −1 and Day 56. In general, the drug was very well tolerated in these patients.

This combination of effects (weight loss and improvement in measures related to glycemic control, cardiovascular disease, and renal function) is highly useful. As noted above, many drugs that have shown the ability to induce weight loss have also shown unacceptable side effects. In addition to its excellent overall tolerability profile, bardoxolone methyl has shown beneficial effects in measures related to several serious obesity-related diseases.

A twelve-month toxicity study for bardoxolone methyl was also conducted on cynomolgus monkeys and their weight was monitored. All the animals were healthy and within normal weights for their age at the start of the study. Interestingly, all groups of animals treated with bardoxolone methyl gained significant amounts of weight at both 26 weeks and 50 weeks. This is consistent with the observation that BARD does not indiscriminately induce weight loss. Instead, in some embodiments its effects appear to be selective to those patients that are overweight and/or obese.

B. Renal Failure

Renal failure, resulting in inadequate clearance of metabolic waste products from the blood and abnormal concentrations of electrolytes in the blood, is a significant medical problem throughout the world, especially in developed countries. See U.S. Patent Application Publication 2009/0326063A1, which is incorporated by reference herein in its entirety. Diabetes and hypertension are among the most important causes of chronic renal failure (CKD), but it is also associated with other conditions such as lupus. Acute renal failure may arise from exposure to certain drugs (e.g., acetaminophen) or toxic chemicals, or from ischemia-reperfusion injury associated with shock or surgical procedures such as transplantation, and may result in chronic renal failure. In many patients, renal failure advances to a stage in which the patient requires regular dialysis or kidney transplantation to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Inflammation contributes significantly to the pathology of CKD. There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001). Furthermore, several studies have demonstrated that HO-1 expression is induced in response to renal damage and inflammation and that this enzyme and its products—bilirubin and carbon monoxide—play a protective role in the kidney (Nath et al., 2006).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

C. Cardiovascular Disease

Cardiovascular (CV) disease is among the most important causes of mortality worldwide, and is the leading cause of death in many developed nations. See U.S. Patent Application Publication 2009/0326063A1, which is incorporated by reference herein in its entirety. The etiology of CV disease is complex, but the majority of causes are related to inadequate or completely disrupted supply of blood to a critical organ or tissue. Frequently such a condition arises from the rupture of one or more atherosclerotic plaques, which leads to the formation of a thrombus that blocks blood flow in a critical vessel. Such thrombosis is the principal cause of heart attacks, in which one or more of the coronary arteries is blocked and blood flow to the heart itself is disrupted. The resulting ischemia is highly damaging to cardiac tissue, both from lack of oxygen during the ischemic event and from excessive formation of free radicals after blood flow is restored (a phenomenon known as ischemia-reperfusion injury). Similar damage occurs in the brain during a thrombotic stroke, when a cerebral artery or other major vessel is blocked by thrombosis. Hemorrhagic strokes, in contrast, involve rupture of a blood vessel and bleeding into the surrounding brain tissue. This creates oxidative stress in the immediate area of the hemorrhage, due to the presence of large amounts of free heme and other reactive species, and ischemia in other parts of the brain due to compromised blood flow. Subarachnoid hemorrhage, which is frequently accompanied by cerebral vasospasm, also causes ischemia/reperfusion injury in the brain.

Alternatively, atherosclerosis may be so extensive in critical blood vessels that stenosis (narrowing of the arteries) develops and blood flow to critical organs (including the heart) is chronically insufficient. Such chronic ischemia can lead to end-organ damage of many kinds, including the cardiac hypertrophy associated with congestive heart failure.

Atherosclerosis, the underlying defect leading to many forms of cardiovascular disease, occurs when a physical defect or injury to the lining (endothelium) of an artery triggers an inflammatory response involving the proliferation of vascular smooth muscle cells and the infiltration of leukocytes into the affected area. Ultimately, a complicated lesion known as an atherosclerotic plaque may form, composed of the above-mentioned cells combined with deposits of cholesterol-bearing lipoproteins and other materials (e.g., Hansson and Anton, 2006).

Pharmaceutical treatments for cardiovascular disease include preventive treatments, such as the use of drugs intended to lower blood pressure or circulating levels of cholesterol and lipoproteins, as well as treatments designed to reduce the adherent tendencies of platelets and other blood cells (thereby reducing the rate of plaque progression and the risk of thrombus formation). More recently, drugs such as streptokinase and tissue plasminogen activator have been introduced and are used to dissolve the thrombus and restore blood flow. Surgical treatments include coronary artery bypass grafting to create an alternative blood supply, balloon angioplasty to compress plaque tissue and increase the diameter of the arterial lumen, and carotid endarterectomy to remove plaque tissue in the carotid artery. Such treatments, especially balloon angioplasty, may be accompanied by the use of stents, expandable mesh tubes designed to support the artery walls in the affected area and keep the vessel open. Recently, the use of drug-eluting stents has become common in order to prevent post-surgical restenosis (renarrowing of the artery) in the affected area. These devices are wire stents coated with a biocompatible polymer matrix containing a drug that inhibits cell proliferation (e.g., paclitaxel or rapamycin). The polymer allows a slow, localized release of the drug in the affected area with minimal exposure of non-target tissues. Despite the significant benefits offered by such treatments, mortality from cardiovascular disease remains high and significant unmet needs in the treatment of cardiovascular disease remain.

As noted above, induction of HO-1 has been shown to be beneficial in a variety of models of cardiovascular disease, and low levels of HO-1 expression have been clinically correlated with elevated risk of CV disease. Compounds disclosed herein, therefore, may be used in treating or preventing a variety of cardiovascular disorders including but not limited to atherosclerosis, hypertension, myocardial infarction, chronic heart failure, stroke, subarachnoid hemorrhage, and restenosis.

D. Diabetes

Diabetes is a complex disease characterized by the body's failure to regulate circulating levels of glucose. See U.S. Patent Application Publication 2009/0326063A1, which is incorporated by reference herein in its entirety. This failure may result from a lack of insulin, a peptide hormone that regulates the both the production and absorption of glucose in various tissues. Deficient insulin compromises the ability of muscle, fat, and other tissues to absorb glucose properly, leading to hyperglycemia (abnormally high levels of glucose in the blood). Most commonly, such insulin deficiency results from inadequate production in the islet cells of the pancreas. In the majority of cases this arises from autoimmune destruction of these cells, a condition known as type 1 or juvenile-onset diabetes, but may also be due to physical trauma or some other cause.

Diabetes may also arise when muscle and fat cells become less responsive to insulin and do not absorb glucose properly, resulting in hyperglycemia. This phenomenon is known as insulin resistance, and the resulting condition is known as Type 2 diabetes. Type 2 diabetes, the most common type, is highly associated with obesity and hypertension. Obesity is associated with an inflammatory state of adipose tissue that is thought to play a major role in the development of insulin resistance (e.g., Hotamisligil, 2006; Guilherme et al., 2008).

Diabetes is associated with damage to many tissues, largely because hyperglycemia (and hypoglycemia, which can result from excessive or poorly timed doses of insulin) is a significant source of oxidative stress. Chronic kidney failure, retinopathy, peripheral neuropathy, peripheral vasculitis, and the development of dermal ulcers that heal slowly or not at all are among the common complications of diabetes. Because of their ability to protect against oxidative stress, particularly by the induction of HO-1 expression, compounds disclosed herein may be used in treatments for many complications of diabetes. As noted above (Cai et al., 2005), chronic inflammation and oxidative stress in the liver are suspected to be primary contributing factors in the development of Type 2 diabetes. Furthermore, PPARγ agonists such as thiazolidinediones are capable of reducing insulin resistance and are known to be effective treatments for Type 2 diabetes.

Based on experimental results obtained, including those presented in this application, the compounds and methods of this invention may be used for treating patients with neuroinflammation.

The effect of treatment of diabetes may be evaluated as follows. Both the biological efficacy of the treatment modality as well as the clinical efficacy are evaluated, if possible. For example, disease manifests itself by increased blood sugar, the biological efficacy of the treatment therefore can be evaluated, for example, by observation of return of the evaluated blood glucose towards normal. Measuring a clinical endpoint which can give an indication of b-cell regeneration after, for example, a six-month period of time, can give an indication of the clinical efficacy of the treatment regimen.

E. Liver Disease

Liver disease (also called hepatic disease) is a broad term describing any single number of diseases affecting the liver. Many are accompanied by jaundice caused by increased levels of bilirubin in the system. The bilirubin results from the breakup of the hemoglobin of dead red blood cells; normally, the liver removes bilirubin from the blood and excretes it through bile.

Various types of liver disease include:
Hepatitis, inflammation of the liver, caused mainly by various viruses but also by some poisons (e.g., alcohol), autoimmunity (autoimmune hepatitis) or hereditary conditions;
Non-alcoholic fatty liver disease, a spectrum in disease, associated with obesity and characterized as an abundance of fat in the liver; may lead to a hepatitis, i.e., steatohepatitis and/or cirrhosis;
Cirrhosis (the formation of fibrous tissue in the liver, replacing dead liver cells), cause by viral hepatitis, alcoholism or contact with other liver-toxic chemicals;
Haemochromatosis, a hereditary disease causing the accumulation of iron in the body, eventually leading to liver damage;
Cancer of the liver (primary hepatocellular carcinoma or cholangiocarcinoma and metastatic cancers, usually from other parts of the gastrointestinal tract);
Wilson's disease, a hereditary disease which causes the body to retain copper;
Primary sclerosing cholangitis, an inflammatory disease of the bile duct, likely autoimmune in nature;
Primary biliary cirrhosis, autoimmune disease of small bile ducts;
Budd-Chiari syndrome, obstruction of the hepatic vein;
Gilbert's syndrome, a genetic disorder of bilirubin metabolism, found in about 5% of the population; and
Glycogen storage disease type II, the build-up of glycogen causes progressive muscle weakness (myopathy) throughout the body and affects various body tissues, particularly in the heart, skeletal muscles, liver and nervous system.

There are also many pediatric liver disease, including biliary atresia, alpha-1 antitrypsin deficiency, alagille syndrome, and progressive familial intrahepatic cholestasis, to name but a few.

The external signs of liver disease include a coated tongue, bad breath, itchy skin, excessive sweating, offensive body odor, dark circles under the eyes, red swollen and itchy eyes, acne rosacea, brownish spots and blemishes on the skin, flushed facial appearance or excessive facial blood vessels. Other symptoms include jaundice, dark urine, pale stool, bone loss, easy bleeding, itching, small, spider-like blood vessels visible in the skin, enlarged spleen, fluid in the abdominal cavity, chills, pain from the biliary tract or pancreas, and an enlarged gallbladder.

The symptoms related to liver dysfunction include both physical signs and a variety of symptoms related to digestive problems, blood sugar problems, immune disorders, abnormal absorption of fats, and metabolism problems. The malabsorption of fats may lead to symptoms that include indigestion, reflux, deficit of fatsoluble vitamins, hemorrhoids, gall stones, intolerance to fatty foods, intolerance to alcohol, nausea and vomiting attacks, abdominal bloating, and constipation.

Nervous system disorders include depression, mood changes, especially anger and irritability, poor concentration and "foggy brain," overheating of the body, especially the face and torso, and recurrent headaches (including migraine) associated with nausea. The blood sugar problems include a craving for sugar, hypoglycaemia and unstable blood sugar levels, and the onset of type 2 diabetes.

Abnormalities in the level of fats in the blood stream include high or low levels of lipids. Hypercholesterolemia includes elevated LDL cholesterol, reduced HDL cholesterol, elevated triglycerides, clogged arteries leading to high blood pressure heart attacks and strokes, build up of fat in other body organs (fatty degeneration of organs), lumps of fat in the skin (lipomas and other fatty tumors), excessive weight gain (which may lead to obesity), inability to lose weight even while dieting, sluggish metabolism, protuberant abdomen (pot belly), cellulite, and/or fatty liver. Hypocholesterolemia is low total cholesterol, low LDL and VLDL cholesterol, and/or low triglyderides.

A number of liver function tests are available to test the proper function of the liver. These test for the presence of enzymes in blood that are normally most abundant in liver tissue, metabolites or products. If alcohol-induced liver disease is suspected, blood tests and imaging tests (MRI, CT scan, or ultrasound) may help in diagnosis and to rule out other causes of liver disease but proof is best established by liver biopsy.

A specific X-ray known as the hepatic angiography is used to investigate the veins and arteries that supply blood to the liver. Usually an X-ray is requested only if the CT scan or MRI do not show conclusive information. During a hepatic angiography, a thin and flexible tube is inserted into a blood vessel through a cut into the groin. Then a dye is injected, which lights up the blood vessels for better visualization. This procedure is generally performed under local anesthetic and it is not painful but may be uncomfortable.

Medical imaging tests allow doctors to examine a patient by looking at still and moving images of their internal organs and tissue One of the first tests a patient may be required to take is the ultrasound. This is a routine procedure that is not harmful in any way to the patient since it does not utilize radioactive waves. It normally takes up to 15 minutes to be completed. Before the procedure is performed, a gel is applied on the skin. Its main purposes are to promote easy movements and to make sure that wave sounds are directed through the skin. The solid masses are turned into images that are seen on a monitor by a radiologist. The pictures are recorded and the radiologist will make a report which is to be discussed with the patient's doctor during a specific appointment.

CT scans or computed tomography is a painless procedure used in order to obtain pictures of the body organs and tissues. Unlike the ultrasound, the CT scan uses radiation but with minimal risks. The tomograms taken by a CT scanner can show if there are any abnormalities in the lungs, bones, soft tissues and blood vessels. It is mostly used for studying the abdomen and chest and it can take up to 30 minutes. The CT scanner is a large machine, in which the patient is moved forward and backwards. Before the test is taken, the patient gets an iodine dye into a vein which helps visualizing blood vessels and kidneys and also makes it easier to observe differences between normal and abnormal tissue in the liver and other organs.

Magnetic resonance imaging (MRI) is able to get more detailed images than a CT scan. It is a new technology, a kind of a tube scanner used to create magnetic fields by releasing radio frequency energy. The MRI is mostly used to observe and investigate tumors before and after treatment. It is not a painful procedure and a regular scan session does not usually takes more than 30 minutes. However, some patients may feel claustrophobic during the scan. Some of the patients who have specific implants may not have a MRI due to the existence of metal in their bodies.

The treatment of liver disease is different depending on the type of condition. Liver diseases affect the proper functioning of the liver. Treatment for liver diseases is normally directed towards the relief of symptoms and complications. Most of the time is focused on avoiding the risk factors.

All types of hepatitis are addressed with intravenous therapy fluids due to the dehydration caused by vomiting and diarrhea. Usually, patients whose symptoms are not severe, can treat the disease at home, otherwise, hospitalization may be needed. Medication for nausea and vomiting is also available. Hepatitis B and C may become chronic and unfortunately, there is no medication that can prevent this to happen. Once hepatitis B becomes chronic, it may be treated with antiviral drugs but this type of medication is not effective on all patients. Chronic hepatitis C is treated with the so called pegylated interferon alpha agent (Pegasys or PEG-Intron) that may be combined with an antiviral called ribavirin. The treatment for chronic hepatitis B and C is given based on the results of several tests regarding the functioning of the liver and the type of medication administrated is decided after consulting a gastroenterologist and a liver specialist. However, the usage of interferon in order to treat hepatitis C may be restricted in cases of active alcohol abuse or drug abuse, in cases of depression, autoimmune diseases or low hemoglobin levels.

Treatment for cirrhosis is mainly directed towards the relief of complications. Medication may be used to treat the underlying cause. Some of these include steroids, penicillamine and an anti-inflammatory agent such as colchicine. Their effect is still being studied and at this moment they do not seem to improve the patient's condition. Cirrhosis caused by portal hypertension may be treated with β blockers that lower the blood pressure.

IV. Pharmaceutical Formulations and Routes of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

The compounds of the present disclosure may also be formulated and/or prepared in a variety of ways, including as a solid dispersion. See, for example, PCT Publication WO 2010/093944, which is incorporated herein by reference in its entirety.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Liquid or semi-liquid dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. In some embodiments, the compound, for example bardoxolone methyl, is formulated as a capsule. For oral therapeutic administration, the therapeutic compound may be incorporated with excipients and used in the form of ingestible tablets, buccal tablets, troches, capsules, elixirs, suspensions, syrups, wafers, and the like. In some embodiments, the compound, for example bardoxolone methyl, is formulated as an ingestible tablet. The percentage of the therapeutic compound in the compositions and preparations may, of course, be varied. The amount of the therapeutic compound in such therapeutically useful compositions is such that a suitable dosage will be obtained.

In some embodiments the daily dose of the therapeutic compound for human patients will be from 5 mg to 500 mg. In some of these embodiments, the dose will be from 10 mg to 300 mg. In some of these embodiments, the dose will be from 10 mg to 250 mg. In some of these embodiments, the dose will be from 25 mg to 150 mg. For example in some embodiments, the daily dose of bardoxolone methyl will be about 25 mg, about 75 mg or about 150 mg. In some embodiments, about 25 mg, about 75 mg or about 150 mg of bardoxolone methyl may be incorporated with expedients and/or other pharmaceutically suitable ingredients into an ingestible capsule or tablet. In some of these embodiments, the form of the bardoxolone methyl will be Form A.

In some embodiments the daily dose of the therapeutic compound for human patients will be from 5 mg to 50 mg. In some of these embodiments, the dose will be from 10 mg to 40 mg. For example in some embodiments, the daily dose of bardoxolone methyl will be about 10 mg, about 20 mg or about 40 mg. In some embodiments, about 10 mg, about 20 mg or about 40 mg of bardoxolone methyl may be incorporated with expedients and/or other pharmaceutically suitable ingredients into an ingestible capsule or tablet. In some of these embodiments, the form of the bardoxolone methyl will be Form B. In some of these embodiments, the form of the bardoxolone methyl will be a solid dispersion of Form B. See, for example, PCT Publication WO 2010/093944, which is incorporated herein by reference in its entirety.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In addition to the dosages disclosed above, the an effective amount of the compounds may vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 500 mg/kg/day, less than 250 mg/kg/day, less than 100 mg/kg/day, less than 50 mg/kg/day, less than 25 mg/kg/day, less than 10 mg/kg/day or less than less than 1 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

V. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as when a compound of the present invention is "A" and "B" represents a secondary agent, non-limiting examples of which are described below:

| A/B/A | B/A/B | B/B/A | A/A/B | A/B/B | B/A/A | A/B/B/B | B/A/B/B |
| B/B/B/A | | B/B/A/B | A/A/B/B | A/B/A/B | A/B/B/A | B/B/A/A |
| B/A/B/A | | B/A/A/B | A/A/A/B | B/A/A/A | A/B/A/A | A/A/B/A |

It is contemplated that other anti-inflammatory agents may be used in conjunction with the treatments of the current invention. For example, other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See also U.S. Pat. No. 6,025,395, which is incorporated herein by reference.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention.

Other particular secondary therapies include immunosuppressants (for transplants and autoimmune-related RKD), anti-hypertensive drugs (for high blood pressure-related RKD, e.g., angiotensin-converting enzyme inhibitors and angiotensin receptor blockers), insulin (for diabetic RKD), lipid/cholesterol-lowering agents (e.g., HMG-CoA reductase inhibitors such as atorvastatin or simvastatin), treatments for hyperphosphatemia or hyperparathyroidism associated with CKD (e.g., sevelamer acetate, cinacalcet), dialysis, and dietary restrictions (e.g., protein, salt, fluid, potassium, phosphorus).

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Clinical Weight Reduction Data in Phase 2 Study

In a clinical trial of bardoxolone methyl in patients having Type 2 diabetes and chronic kidney disease, designed to measure the drug's effect on measures of kidney function, glycemic control, insulin resistance, and cardiovascular disease, clear improvements in all these parameters were noted. See U.S. Patent Application Publication 2009/0326063A1, which is incorporated by reference herein in its entirety.

Patients received 25 mg bardoxolone methyl once per day for 28 days (given orally in capsule form), followed by 75 mg once per day for 28 days (given orally in capsule form). In this study, the protocol stipulated that patient weights were to be taken at baseline (D-1=1 day before initiation of dosing), Day 28, and Day 56. Weight data were available for all but one patient who started the study (a baseline weight was not recorded for this patient). In the remaining patients, 14 of 17 had lost weight at Day 28 (mean weight loss was 1.6% of baseline weight) and 17 of 17 had lost weight at Day 56 (mean weight loss was 3.7% of baseline, with a median of 3.1%). All patients, including the patient who did not have a baseline weight available, lost weight between Day 28 and Day 56. A large majority of these patients were overweight or clinically obese (Mean baseline weight was 101 kg). As shown in Table 1, all but three patients lost more than 2% of their baseline weight between Day -1 and Day 56. In general, the drug was very well tolerated in these patients. Additional patient data is provided in Tables 2 and 3.

Prior to initiation of treatment, basic clinical observations (e.g., weight, blood pressure, height) were recorded along with baseline values for serum creatinine, blood urea nitrogen, serum phosphorus, serum uric acid, angiotensin II, fasting glucose, hemoglobin A1c, circulating endothelial cells (CECs), and iNOS-positive CECs.

Parameters related to renal function improved significantly after 28 days of treatment (eGFR increased approximately 10%) and still further after 56 days of treatment (eGFR increased more than 20% compared to baseline). Reductions of more than 10% were also observed in BUN, serum creatinine, uric acid, and urinary albumin creatinine ratio. Significant reductions in CECs and iNOS-positive CECs were also noted. Results are summarized in Table 4.

TABLE 1

Weigh Levels and Percent Change in Response to Bardoxolone Methyl in Chronic Kidney Disease (CKD) Patients

| Patient ID | Start Dose (mg) | Escalated Dose (mg) | Weight (kg) | | | Percent Change D28/D-1 | Percent Change D56/D-1 |
| --- | --- | --- | --- | --- | --- | --- | --- |
| | | | D-1 | D28 | D56 | | |
| 032 | 25 | 75 | 88.0 | 88.0 | 87.1 | 0.0% | -1.0% |
| 033 | 25 | 75 | 80.7 | 80.7 | 75.7 | 0.0% | -6.2% |
| 036 | 25 | 75 | 76.2 | 75.7 | 74.4 | -0.7% | -2.4% |
| 029 | 25 | 75 | 111.6 | 108.9 | 107.0 | -2.4% | -4.1% |
| 045 | 25 | 75 | 81.6 | 80.3 | 78.5 | -1.6% | -3.8% |
| 039 | 25 | 75 | 104.3 | 100.7 | 97.1 | -3.5% | -6.9% |
| 044 | 25 | 75 | 111.6 | 108.9 | 108.0 | -2.4% | -3.2% |
| 047 | 25 | 75 | 114.3 | 112.9 | 111.1 | -1.2% | -2.8% |
| 038 | 25 | 75 | 86.2 | 78.9 | 77.1 | -8.5% | -10.6% |
| 049 | 25 | 75 | 89.8 | 88.5 | 88 | -1.4% | -2.0% |
| 050 | 25 | 75 | N/A | 104.3 | 102.1 | N/A | N/A |
| 084 | 25 | 75 | 169.4 | 169.3 | 165.9 | -0.1% | -2.1% |
| 051 | 25 | 75 | 60.3 | 52.6 | 52.2 | -12.8% | -13.4% |
| 052 | 25 | 75 | 83.9 | 83.5 | 80.3 | -0.5% | -4.3% |
| 055 | 25 | 75 | 159.2 | 159.7 | 157.9 | 0.3% | -0.8% |
| 102 | 25 | 75 | 114.4 | 114 | 110.4 | -0.3% | -3.5% |
| 008 | 25 | N/A | 93.0 | 92.1 | 91.6 | -1.0% | -1.5% |
| 100 | 25 | N/A | 92.7 | 89.9 | 87.4 | -3.0% | -5.7% |
| Mean | | All | 101.0 | 99.4 | 97.3 | -1.6% | -3.7% |

TABLE 2

Additional Patient Data

| Patient ID | Age | Sex | Diabetes Duration | ACE | ARB | Other Renal | Statin | Insulin | Epo and Related Drugs | Non-renal Diabetic Complications | Hypertensive |
| --- | --- | --- | --- | --- | --- | --- | --- | --- | --- | --- | --- |
| 032 | 87 | M | 49 | N | Y | Y | Y | N | Y | Y | Y |
| 033 | 76 | F | 8 | N | Y | Y | N | N | N | N | Y |
| 036 | 63 | F | 15 | N | Y | Y | Y | Y | N | N | Y |
| 029 | 50 | M | 3 | N | N | N | Y | N | N | Y | Y |
| 045 | 62 | F | 7 | N | N | Y | Y | Y | Y | N | Y |
| 039 | 73 | F | 26 | N | Y | Y | Y | Y | Y | Y | Y |
| 044 | 70 | M | 1 | N | Y | N | Y | N | N | N | Y |
| 047 | 61 | F | 15 | Y | Y | Y | Y | Y | N | N | Y |
| 038 | 34 | F | 10 | N | Y | Y | Y | Y | N | N | Y |
| 049 | 79 | F | 10 | N | N | Y | N | Y | N | Y | Y |
| 050 | 65 | F | 5 | Y | N | N | Y | Y | N | N | Y |
| 084 | 61 | F | 18 | Y | N | Y | Y | Y | N | Y | Y |
| 051 | 71 | M | 35 | N | N | Y | N | N | Y | Y | Y |
| 052 | 57 | F | 8 | N | Y | Y | Y | Y | N | N | Y |
| 055 | 60 | M | 10 | Y | N | Y | Y | Y | N | N | Y |
| 102 | 68 | M | 29 | N | N | Y | Y | Y | N | N | Y |
| 008 | 56 | M | 3 | N | N | Y | Y | Y | N | Y | Y |
| 100 | 69 | M | 26 | N | Y | Y | Y | N | N | Y | N |

TABLE 3

| Demographics of Patients Completing the Study | (n = 18) |
|---|---|
| Average Age (mean) | 65 |
| Average Diabetes Duration (in yrs) (mean) | 16 |
| Chronic Kidney Disease | 100% |
| Average Baseline eGFR (ml/min/1.73 m$^2$) (mean) | 31.0 |
| Stage 4 CKD | 50% |
| Non-Renal Diabetic Complications[1] | 50% |
| Hypertensive | 94% |
| Hgb A1c (%) | 7.9% |
| Failed Oral Antihyperglycemics | 67% |
| On Stable Renal Meds | 94% |
| RAS Blocker | 78% |
| Ca Channel Blocker | 39% |
| Statin Use | 83% |

[1]Includes neuropathy and retinopathy

TABLE 4

Non-Weight Related Results

| Summary of Stratum 2 Data | All Patients (n = 18) |
|---|---|
| Patients with eGFR Increase | 89% |
| eGFR | +24.1%*** |
| Serum Creatinine | −17.5%** |
| Creatinine Clearance | +38.2%† |
| Urine Albumin to Creatinine Ratio | −14.1% |
| Blood Urea Nitrogen | −14.9% |
| Phosphorus | −2.5% |
| Uric Acid | −13.3%† |
| Hemoglobin A1c (%; BL ≥ 7.0%) | −0.1 |
| Circulating Endothelial Cells | −34.8%† |
| iNOS+ Circulating Endothelial Cells | −65.8%* |

†$p < 0.05$;
*$p < 0.01$;
**$p < 0.001$;
***$p < 0.0001$

Example 2—Toxicity Study in Monkeys

Bardoxolone methyl and vehicle were administered once per day for 353 days during the study via oral gavage to a group of cynomolgus monkeys. All the animals were healthy and within normal weights for their age at the start of the study. The dose levels were 0, 30/5, 100/30, and 300 mg/kg/day and administered at a dose volume of 3 mL per dose. The control group received the vehicle in the same manner as the treated groups. Just prior to administration, the test article for each animal was added to the syringe containing the vehicle for each animal and vortexed until thoroughly mixed to achieved the desired concentrations of 30, 100, and 300 mg/mL through Day 42 (Week 6). During administration, the syringe containing the test article preparation for each animal was pushed through the gavage tube. The 1 mL vehicle rinse was then added to the dosing syringe and administered. After administration of both volumes, a 5 mL flush of the vehicle was used to rinse the gavage tube and ensure that the entire amount of the test article was administered to the animal. Analysis of whole blood samples from Days 1 and 28 indicated no significant differences in exposure across the three dose levels. Therefore, dose levels were adjusted so that different blood exposures could be examined. During Week 7 dosing for all animals was stopped for four days (Days 43 to 46). The initial dose levels of 30 and 100 mg/kg/day were reduced to 5 and 30 mg/kg/day, respectively, and dosing was resumed on Day 47 through Day 353. Individual doses were based on the most recent body weights. Results of this study are summarized in Table 5. All treated groups gained weight during the study, indicating that bardoxolone methyl treatment did not induce weight loss in healthy monkeys with normal body weights.

TABLE 5

Body Weight Observations in 12-Month Toxicology Study of Bardoxolone Methyl in Cynomolgus Monkeys

| | Males | | | | | Females | | | | |
|---|---|---|---|---|---|---|---|---|---|---|
| | Pretest Weight (kg) | Week 26 Weight (kg) | Week 50 Weight (kg) | kg gained | % gain | Pretest Weight (kg) | Week 26 Weight (kg) | Week 50 Weight (kg) | kg gained | % gain |
| Control | 2.119 | 2.791 | 3.35 | 1.231 | 58.09% | 2.047 | 2.608 | 2.892 | 0.845 | 41.28% |
| 30/5 | 2.128 | 2.567 | 2.975 | 0.847 | 39.80% | 2.069 | 2.454 | 2.608 | 0.539 | 26.05% |
| 100/30 | 2.152 | 2.464 | 2.725 | 0.573 | 26.63% | 2.058 | 2.293 | 2.68 | 0.622 | 30.22% |
| 300 | 2.141 | 2.52 | 2.808 | 0.667 | 31.15% | 2.084 | 2.552 | 2.68 | 0.596 | 28.60% |

Example 3—Clinical Weight Reduction Data in Phase 2b/3 Study

The efficacy and safety of bardoxolone methyl were studied in a Phase 2b/3 trial in patients with Stage 3b or Stage 4 CKD and Type 2 diabetes. Weight measurements were included in the study as a basic clinical parameter.

A. Patient Population

The study randomized adults with moderate to severe CKD and type 2 diabetes mellitus who had screening estimated GFR (using the MDRD formula) between 20 and 45 mL/min/1.73 m$^2$. Screening estimated GFR was calculated as the mean of two estimated GFR results (differing no more than 25%) collected at least 5 days apart within a 3-week period. Treatment with an angiotensin converting enzyme inhibitor, an angiotensin receptor blocker, or both for at least three months with a stable dose for at least eight weeks prior to screening was required; 98% of patients met this criterion. Exclusion criteria included type 1 diabetes, non-diabetic kidney disease, hemoglobin A1c>10%, QTc Fredericia interval >450 milliseconds, evidence of hepatic dysfunction, and recent cardiovascular disease.

B. Study Design

The study randomized 227 patients 1:1:1:1 to receive placebo, 25, 75, or 150 mg bardoxolone methyl for 52 weeks, inclusive of titration to the assigned dose level. The study had four periods: (1) 21-days of screening/placebo run-in; (2) 8-week titration period to reach the randomized dose, with an extension up to 20 weeks in patients who had trouble tolerating the drug or an abnormal laboratory test result that precluded final titration within 8 weeks; (3) dose maintenance period from end of titration through Week 52; and (4) 4-week follow-up period after the last dose of study drug. Study drug was taken orally once daily in the morning one hour prior to food intake. Dose titration occurred as follows: (1) placebo; (2) 25 mg; (3) 25 mg, increased to 75 mg after 4 weeks; and (4) 25 mg, increased to 75 mg after 4 weeks, further increased to 150 mg after an additional 4 weeks. Randomization was stratified by CKD stage (3b versus 4), urinary albumin to creatinine ratio (ACR; ≤ versus >300 mg/g), and glucose control (hemoglobin A1c< versus ≥7%). An independent Data Safety Monitoring Board monitored patient safety.

C. Procedures and Outcomes

Estimated GFR and routine safety laboratory testing was done at screening and every four weeks thereafter using a central laboratory. Adverse events and clinical laboratory parameters were assessed at each visit. Analysis of the primary outcome, change from baseline estimated GFR at Week 24, occurred after all randomized patients completed Week 24 or previously discontinued study. Exploratory outcomes included change from baseline at Week 24 in serum creatinine, blood urea nitrogen, serum phosphorus, uric acid, ACR, hemoglobin A1c, and intact parathyroid hormone.

D. Patient Characteristics

Treatment groups were generally well balanced with respect to baseline variables (Table 6) although the placebo group had a slightly lower percentage of males (49%) than the active groups (59%). Mean age was 67 years. Mean time between diagnosis of diabetes mellitus and randomization was 18 years; diabetes was well controlled with mean baseline hemoglobin A1c of 7.2%. At study entry, mean estimated GFR was 32.4 mL/min/1.73 m$^2$, with 62% of patients having Stage 3b CKD and 38% having Stage 4 CKD. Median baseline ACR was 596 mg/g. ACR>300 mg/g (macroalbuminuria), 30-300 mg/g (microalbuminuria), and <30 mg/g were each represented by one-third of the patients. Ninety-eight percent of patients were receiving ACE inhibitor, ARB therapy, or both; the remaining patients received a waiver from the inclusion criteria because they were intolerant to these medications.

E. Primary Outcome

Figure 2:
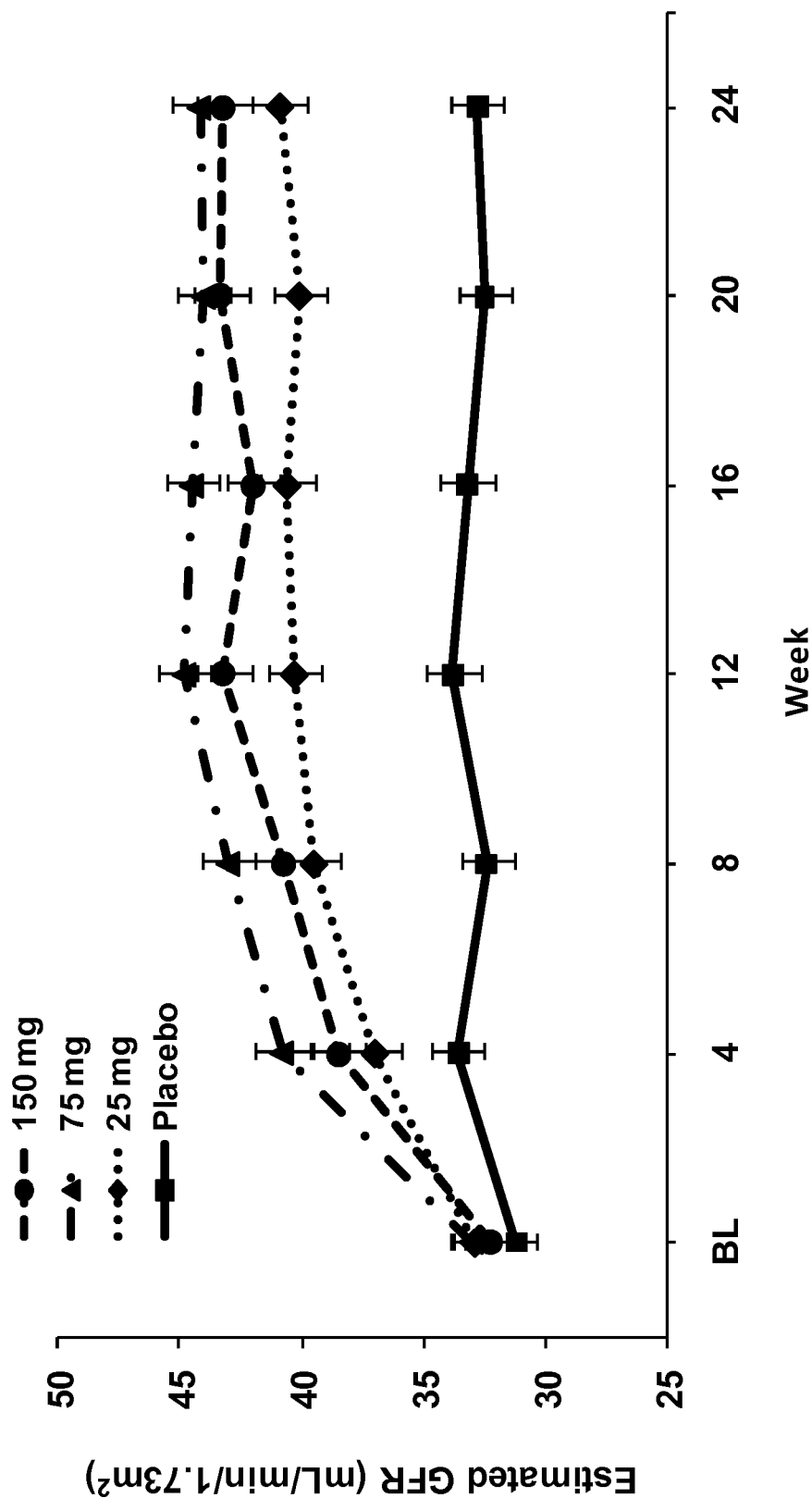
FIG. 2—Estimated GFR Changes Over Time and Magnitude of Change in Diabetic CKD Patients Treated with Bardoxolone Methyl for 24 Weeks. Estimated GFR changes for patients by dose group at Week 24, based on results of longitudinal model, using the ITT population. Data are depicted as mean±standard error; n=57 (placebo, 25 mg, and 75 mg); n=56 (150 mg).
Figure 3:
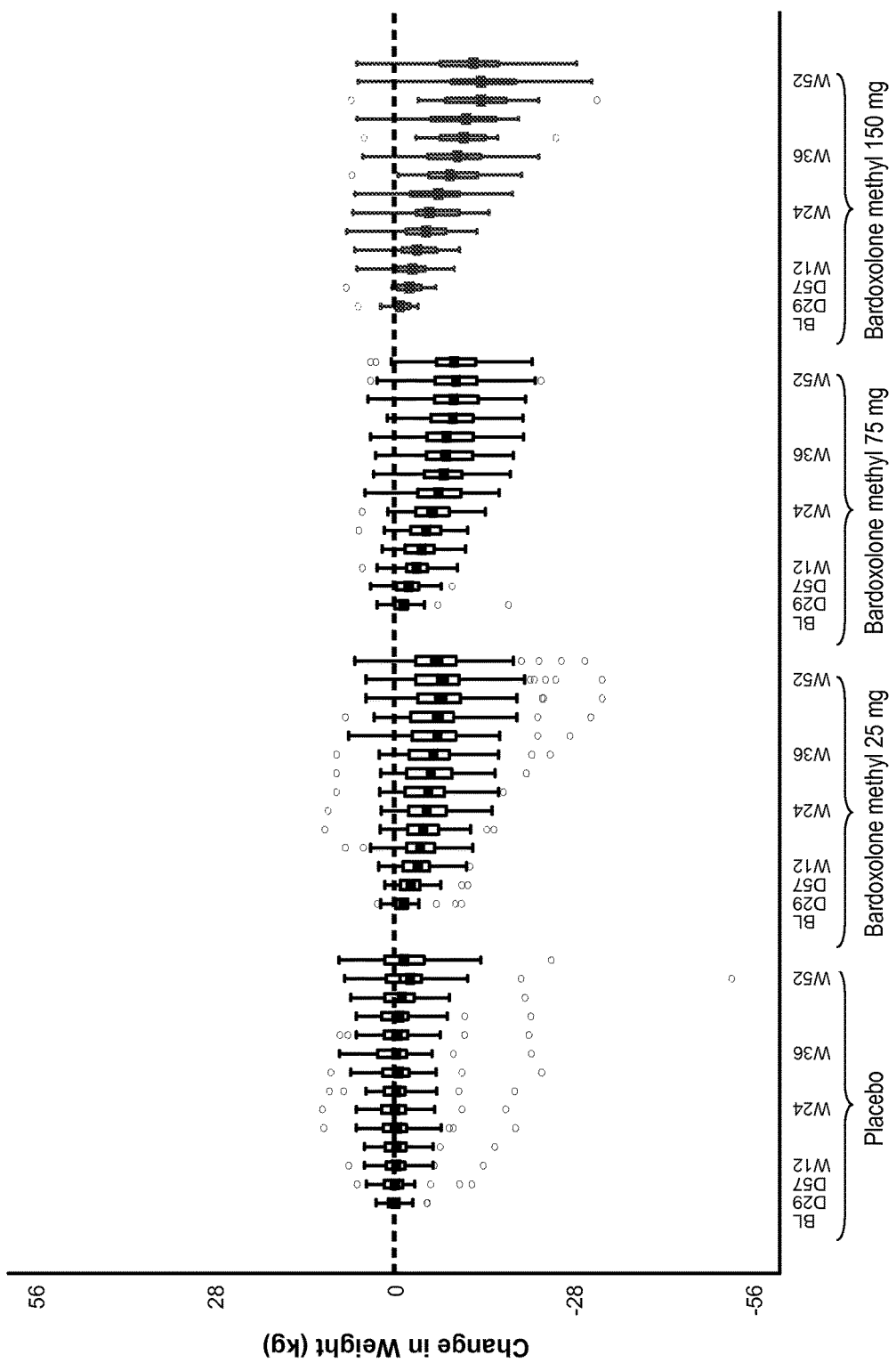
FIG. 3—Weight over Time by Last Dose Received. This figure compares the weight change over 52 weeks for the patient population of Examples 3 and 4. BL=baseline. W=weeks. D=days.

At Week 24, all bardoxolone methyl groups showed increases in estimated GFR both relative to baseline and to changes in the placebo group, with mean increases compared to placebo of 8.3±1.1, 11.5±1.1, and 10.6±1.1 mL/min/1.73 m$^2$ among the 25, 75, and 150 mg groups, respectively (p<0.001, all groups). The placebo group showed essentially no change (0.1±1.1 mL/min/1.73 m$^2$) (Table 7). The difference between the 25 and 75 mg groups was statistically significant (nominal p=0.039) but the difference between the 75 and 150 mg groups was not (p=0.54). Increases in estimated GFR were observed within 4 weeks of treatment initiation for the bardoxolone methyl groups, peaked at Week 12, and remained stable through Week 24 (FIG. 2). At Week 24, 74% of bardoxolone methyl patients experienced more than a 10% increase in estimated GFR, and 24% of bardoxolone methyl patients reported more than a 50% increase in estimated GFR compared to a single placebo patient (data not shown).

Most patients treated with bardoxolone methyl experienced an improvement in CKD stage from Stage 4 to Stage 3b or from Stage 3b to Stage 3a. The percentages improving were 17% in the placebo group, 53% in the 25 mg group, 69% in the 75 mg group, and 61% in the 150 mg group. Furthermore, fewer patients in each bardoxolone methyl group experienced a worsening of CKD stage than in the placebo group (2 patients [4%] in each bardoxolone methyl group compared to 7 patients [13%] in the placebo group).

Weight was reduced over time in the active treatment cohorts. Mean weight change at Week 24 was −5.9, −4.7, and −5.8 kg in the 25, 75, and 150 mg groups, respectively, while no weight change was observed in the placebo group.

Example 4—Clinical Weight Reduction Resulting from 12 Months of Treatment

In a continuation of the study described in Example 3, patients remained in their assigned treatment group (placebo, 25 mg bardoxolone methyl/day, 75 mg bardoxolone methyl/day, 150 mg bardoxolone methyl/day) for an additional 28 weeks, bringing the total treatment period to 52 weeks. The double-blinded structure of the study was maintained throughout the 52-week period. At week 52, patients in all treatment groups had lost additional weight relative to week 24. As shown in Table 8, at least two thirds of patients treated with bardoxolone methyl had lost more than 5 kg by week 52, compared to 21% of placebo-treated patients. Approximately one third of patients treated with bardoxolone methyl had lost more than 10 kg by week 52, compared to 6% of placebo-treated patients. Table 9 shows weight data in 4 week increments for each group over the entire 52 week period of treatment. Treatment was discontinued in all groups at week 52 (including the placebo group), and final clinical and laboratory measurements were taken at week 56. The data in Table 9 demonstrate that patients in the bardoxolone methyl treatment groups lost weight at a relatively uniform rate throughout the 52-week treatment period.

TABLE 6

Demographics and Baseline Characteristics

|  | Placebo<br>N = 57 | Bardoxolone methyl | | | Total<br>N = 227 |
|---|---|---|---|---|---|
|  |  | 25 mg<br>N = 57 | 75 mg<br>N = 57 | 150 mg<br>N = 56 |  |
| Demographic Characteristics |  |  |  |  |  |
| Male, n (%) | 28 (49) | 34 (60) | 33 (58) | 33 (59) | 128 (56) |
| Age, mean (SD) | 67.7 (10) | 66.9 (9.2) | 66.1 (8.7) | 66.7 (9.2) | 66.8 (9.3) |
| Race, n (%) |  |  |  |  |  |
| White | 44 (77) | 44 (77) | 41 (72) | 44 (79) | 173 (76) |
| Black | 10 (18) | 10 (18) | 11 (19) | 11 (20) | 42 (19) |
| Other | 3 (5) | 3 (5) | 5 (9) | 1 (2) | 12 (5) |
| Hispanic or Latino, n (%) | 18 (32) | 12 (21) | 21 (37) | 11 (20) | 62 (27) |
| Baseline Characteristics | Mean (SD) | Mean (SD) | Mean (SD) | Mean (SD) | Mean (SD) |
| Time from diabetes diagnosis to randomization (years) | 17.1 (9.9) | 18.2 (10.8) | 17.8 (9.8) | 18.6 (9.8) | 18.0 (10.0) |
| Weight (kg) | 95.2 (22.8) | 103.0 (22.9) | 97.7 (23.1) | 103.6 (25.3) | 99.8 (23.7) |
| BMI (kg/m$^2$) | 34.4 (8.0) | 36.3 (7.8) | 35.0 (7.6) | 35.8 (7.3) | 35.4 (7.7) |
| SPB (mmHg) | 130.5 (13.5) | 129.5 (12.6) | 130.2 (13.2) | 130.5 (11.8) | 130.2 (12.7) |
| DBP (mmHg) | 67.3 (9.0) | 68.7 (8.3) | 69.7 (8.1) | 68.6 (8.7) | 68.6 (8.5) |
| Hemoglobin A$_{1c}$ (%) | 7.2 (1.2) | 7.2 (0.9) | 7.3 (1.0) | 7.1 (1.1) | 7.2 (1.0) |
| Baseline Laboratory Results | Mean (SD) | Mean (SD) | Mean (SD) | Mean (SD) | Mean (SD) |
| eGFR (mL/min/1.73 m$^2$) | 31.2 (6.3) | 32.9 (7.0) | 33.0 (6.6) | 32.3 (7.6) | 32.4 (6.9) |
| Serum creatinine (mg/dL) | 2.0 (0.5) | 1.0 (0.5) | 2.0 (0.5) | 2.0 (0.6) | 2.0 (0.5) |
| ACR (mg/g), median (IQ range) | 689 (1692) | 507 (855) | 656 (1131) | 531 (819) | 596 (1173) |

Column header counts are the number of randomized patients within each group. Each line includes data only for patients with relevant data.

TABLE 7

Change from Baseline eGFR at Week 24 Using the Longitudinal Model

| Estimates | n | Change from baseline eGFR (mL/min/1.73 m$^2$) mean ± SE | Nominal 95% CI | p-value |
|---|---|---|---|---|
| Treatment group[a] |  |  |  |  |
| Bardoxolone methyl, 25 mg | 57 | 8.3 ± 1.1 | (6.1, 10.4) | <0.001 |
| Bardoxolone methyl, 75 mg | 57 | 11.5 ± 1.1 | (9.3, 13.7) | <0.001 |
| Bardoxolone methyl, 150 mg | 56 | 10.6 ± 1.1 | (8.4, 12.7) | <0.001 |
| Combined bardoxolone methyl, all doses | 170 | 10.1 ± 0.6 | (8.9, 11.4) | <0.001 |
| Placebo | 57 | 0.1 ± 1.1 | (−2.0, 2.2) | 0.92 |
| Differences between bardoxolone methyl and placebo[b] |  |  |  |  |
| Bardoxolone methyl, 25 mg | 57 vs. 57 | 8.2 ± 1.5 | (4.5, 11.8) | <0.001 |
| Bardoxolone methyl, 75 mg | 57 vs. 57 | 11.4 ± 1.5 | (7.8, 15.0) | <0.001 |
| Bardoxolone methyl, 150 mg | 56 vs. 57 | 10.5 ± 1.5 | (6.8, 14.1) | <0.001 |
| Combined bardoxolone methyl | 170 vs. 57 | 10.0 ± 1.3 | (7.5, 12.5) | <0.001 |

The estimates come from a longitudinal model with (1) post-baseline measurements as the response variable; (2) treatment group, time, treatment group by time interaction, and continuous covariates (baseline eGFR, hemoglobin A1c, and ACR); and (3) a Toeplitz covariance structure.

[a]Each p-value comes from a test comparing the mean changes to zero.

[b]Each p-value comes from a test comparing the difference in means between one bardoxolone methyl group and placebo.

TABLE 8

Changes in weight from baseline to Week 52

| | | Bardoxolone methyl | | |
|---|---|---|---|---|
| Change in weight | Placebo N = 52 n (%) | 25 mg N = 48 n (%) | 75 mg N = 48 n (%) | 150 mg N = 45 n (%) |
| Increase | | | | |
| >5 kg | 4 (8) | 0 | 0 | 1 (2) |
| within 5 kg | 18 (35) | 5 (10) | 4 (8) | 2 (4) |
| Decrease | | | | |
| within 5 kg | 19 (37) | 8 (17) | 12 (25) | 8 (18) |
| >5 kg | 11 (21) | 35 (73) | 32 (67) | 34 (76) |
| >10 kg | 3 (6) | 16 (33) | 14 (29) | 22 (49) |
| >15 kg | 2 (4) | 9 (19) | 4 (8) | 12 (27) |

Column header N counts (and denominators for calculating percentages) are the number of treated patients within each randomized group having both baseline and Week 52 weight results.

TABLE 9

Weight over Time

Weight (kg)

| | | Placebo | | Bardoxolone methyl | | | | |
|---|---|---|---|---|---|---|---|---|
| | | | | 25 mg | | 75 mg | | 150 mg |
| Timepoint | n | Mean (95% CI) | n | Mean (95% CI) | n | Mean (95% CI) | n | Mean (95% CI) |
| Baseline | 57 | 95.2 (89.1, 101.3) | 57 | 103.0 (96.9, 109.1) | 57 | 97.7 (91.5, 103.8) | 56 | 103.6 (96.8, 110.3) |
| Week 4 | 56 | 94.9 (88.8, 101.0) | 54 | 102.9 (96.8, 109.0) | 56 | 95.7 (89.7, 101.7) | 55 | 102.0 (95.2, 108.9) |
| Week 8 | 55 | 94.6 (88.4, 100.7) | 53 | 102.0 (95.8, 108.2) | 52 | 94.8 (88.8, 100.8) | 55 | 101.2 (94.4, 108.1) |
| Week 12 | 52 | 94.5 (87.9, 101.1) | 52 | 101.0 (94.6, 107.5) | 52 | 94.0 (88.1, 99.9) | 54 | 100.3 (93.5, 107.2) |
| Week 16 | 54 | 94.9 (88.5, 101.2) | 52 | 100.0 (93.6, 106.4) | 53 | 91.7 (85.7, 97.6) | 53 | 98.1 (91.3, 104.8) |
| Week 20 | 54 | 94.9 (88.6, 101.2) | 50 | 99.8 (93.0, 106.6) | 52 | 92.0 (86.1, 97.9) | 52 | 96.7 (89.8, 103.6) |
| Week 24 | 53 | 95.0 (88.4, 101.5) | 51 | 98.5 (91.9, 105.0) | 52 | 91.7 (85.9, 97.6) | 51 | 95.5 (88.6, 102.4) |
| Week 28 | 52 | 95.0 (88.4, 101.6) | 49 | 98.0 (91.3, 104.8) | 50 | 91.8 (85.7, 97.8) | 47 | 95.1 (87.7, 102.4) |
| Week 32 | 52 | 94.6 (88.1, 101.2) | 49 | 97.9 (91.1, 104.7) | 48 | 91.6 (85.4, 97.8) | 47 | 94.1 (86.8, 101.3) |
| Week 36 | 53 | 95.1 (88.6, 101.6) | 46 | 96.9 (90.1, 103.8) | 49 | 91.0 (84.9, 97.1) | 48 | 95.7 (88.1, 103.2) |
| Week 40 | 53 | 95.0 (88.5, 101.5) | 47 | 96.8 (90.3, 103.3) | 50 | 90.6 (84.7, 96.6) | 46 | 95.2 (87.4, 103.0) |
| Week 44 | 51 | 94.6 (87.9, 101.3) | 48 | 96.1 (89.6, 102.5) | 48 | 90.8 (84.5, 97.0) | 45 | 94.7 (86.8, 102.6) |
| Week 48 | 53 | 94.3 (87.9, 100.7) | 48 | 95.5 (89.1, 101.9) | 47 | 90.4 (84.0, 96.7) | 46 | 94.4 (86.7, 102.1) |
| Week 52 | 52 | 92.9 (86.1, 99.8) | 48 | 95.0 (88.6, 101.5) | 48 | 90.0 (83.9, 96.2) | 45 | 94.5 (86.7, 102.3) |
| Week 56 | 51 | 92.9 (86.4, 99.3) | 46 | 97.2 (90.4, 104.0) | 43 | 90.7 (84.5, 97.0) | 40 | 93.6 (85.3, 102.0) |

Change from baseline weight (kg)

| | | Placebo | | Bardoxolone methyl | | | | |
|---|---|---|---|---|---|---|---|---|
| | | | | 25 mg | | 75 mg | | 150 mg |
| Timepoint | n | Mean (95% CI) | n | Mean (95% CI) | n | Mean (95% CI) | n | Mean (95% CI) |
| Baseline | — | — | — | — | — | — | — | — |
| Week 4 | 56 | −0.2 (−0.6, 0.3) | 54 | −1.4 (−1.9, −0.9) | 56 | −1.4 (−2.0, −0.8) | 55 | −1.3 (−2.1, −0.6) |
| Week 8 | 55 | 0.1 (−0.5, 0.8) | 53 | −2.7 (−3.3, −2.1) | 52 | −2.6 (−3.5, −1.7) | 55 | −2.1 (−2.7, −1.5) |
| Week 12 | 52 | −0.2 (−1.1, 0.7) | 52 | −3.9 (−4.8, −3.1) | 52 | −3.4 (−4.2, −2.6) | 54 | −3.3 (−4.2, −2.5) |
| Week 16 | 54 | −0.3 (−1.1, 0.6) | 52 | −4.3 (−5.3, −3.4) | 53 | −4.1 (−5.0, −3.1) | 53 | −3.9 (−4.8, −2.9) |

TABLE 9-continued

Weight over Time

| | | | | | | | | |
|---|---|---|---|---|---|---|---|---|
| Week 20 | 54 | −0.3 (−1.4, 0.9) | 50 | −5.0 (−6.1, −3.8) | 52 | −4.4 (−5.5, −3.3) | 52 | −5.0 (−6.1, −3.8) |
| Week 24 | 53 | 0.0 (−1.2, 1.1) | 51 | −5.9 (−7.1, −4.7) | 52 | −4.7 (−5.8, −3.5) | 51 | −5.8 (−7.1, −4.6) |
| Week 28 | 52 | −0.2 (−1.4, 1.0) | 49 | −6.3 (−7.7, −4.9) | 50 | −5.1 (−6.4, −3.8) | 47 | −6.7 (−8.1, −5.2) |
| Week 32 | 52 | −0.6 (−1.9, 0.7) | 49 | −6.7 (−8.2, −5.3) | 48 | −6.2 (−7.6, −4.7) | 47 | −7.2 (−8.8, −5.7) |
| Week 36 | 53 | −0.3 (−1.6, 0.9) | 46 | −7.4 (−9.1, −5.7) | 49 | −6.1 (−7.6, −4.5) | 48 | −8.1 (−9.7, −6.5) |
| Week 40 | 53 | −0.5 (−1.8, 0.8) | 47 | −7.9 (−9.6, −6.1) | 50 | −6.5 (−8.1, −5.0) | 46 | −8.7 (−10.4, −7.0) |
| Week 44 | 51 | −0.7 (−2.0, 0.6) | 48 | −8.2 (−10.2, −6.3) | 48 | −6.9 (−8.5, −5.3) | 45 | −9.2 (−11.0, −7.4) |
| Week 48 | 53 | −1.1 (−2.4, 0.1) | 48 | −8.8 (−10.8, −6.8) | 47 | −7.4 (−9.1, −5.7) | 46 | −10 (−12.2, −7.8) |
| Week 52 | 52 | −2.4 (−4.8, 0.0) | 48 | −9.3 (−11.4, −7.1) | 48 | −7.7 (−9.4, −5.9) | 45 | −10 (−12.3, −7.8) |
| Week 56 | 51 | −1.6 (−3.1, −0.0) | 46 | −7.7 (−9.9, −5.6) | 43 | −7.6 (−9.4, −5.9) | 40 | −9.6 (−11.7, −7.4) |

For mean weight, the number of treated patients within each randomized group who have measurements at that timepoint is displayed. For change from baseline weight, the number of treated patients within each randomized group who have both a baseline and a post-baseline measurement at that time is displayed.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 6,025,395
U.S. Ser. No. 61/389,090
U.S. Ser. No. 61/323,276
U.S. Patent Publn. 2003/0232786
U.S. Patent Publn. 2008/0261985
U.S. Patent Publn. 2009/0048204
U.S. Patent Publn. 2009/0326063
U.S. Patent Publn. 2010/0041904
U.S. Patent Publn. 2010/0048887
U.S. Patent Publn. 2010/0048892
U.S. Patent Publn. 2010/0048911
U.S. Patent Publn. 2010/0056777
PCT Appln. WO 2002/092768
PCT Appln. WO 2005/113761
PCT Appln. WO 2009/023232
PCT Appln. WO 2010/093944
Abraham and Kappas, *Free Radical Biol. Med.,* 39:1-25, 2005.
Ahmad et al., *Cancer Res.,* 68:2920-2926, 2008.
Ahmad et al., *J. Biol. Chem.,* 281:35764-35769, 2006.
Araujo et al., *J. Immunol.,* 171(3):1572-1580, 2003.
Arkan et al., *Nat. Med.,* 11(2):191-198, 2005.
Bach, *Hum. Immunol.,* 67(6):430-432, 2006.
Cai et al., *Nat. Med.,* 11(2):183-190, 2005.
Chauhan and Chauhan, *Pathophysiology,* 13(3):171-181 2006.
Dickerson et al., *Prog Neuropsychopharmacol Biol. Psychiatry,* Mar. 6, 2007.
Dinkova-Kostova et al., *Proc. Natl. Acad. Sci. USA,* 102(12):4584-4589, 2005.
Dudhgaonkar et al., *Eur. J. Pain,* 10(7):573-9, 2006.
Forstermann, *Biol. Chem.,* 387:1521, 2006.
Gao et al., *Carcinogenesis,* 27(4):803-10, 2006.
Goodman et al., *Kidney Int.,* 72(8):945-953, 2007.
Guilherme et al., *Nat. Rev. Mol. Cell Biol.,* 9(5):367-377, 2008.
Habeos et al., *J. Mol Med.,* 86(11):1279-85, 2008.
*Handbook of Pharmaceutical Salts: Properties, and Use* (Stahl and Wermuth Eds., Verlag Helvetica Chimica Acta, 2002.
Hanson et al., *BMC Medical Genetics,* 6(7), 2005.
Hansson and Anton, *Annu. Rev. Entomol.,* 45, 203-231, 2006.
Honda et al. *Bioorg. Med. Chem. Lett.,* 12:1027-1030, 2002.
Honda et al., *J. Med. Chem.,* 43:4233-4246, 2000a.
Honda, et al., *J. Med. Chem.,* 43:1866-1877, 2000b.
Hotamisligil, *Nature,* 444(7121):860-867, 2006.
Ishikawa et al., *Circulation,* 104(15):1831-1836, 2001.
Kansanen et al., *Free Radic. Biol. Med.,* 47(9):1310-7, 2009.
Kawakami et al., *Brain Dev.,* 28(4):243-246, 2006.
Kendall-Tackett, *Trauma Violence Abuse,* 8(2):117-126, 2007.
Kobayashi et al., *Mol. Cell Biol.,* 29(2):493-502, 2009.
Kruger et al., *J. Pharmacol. Exp. Ther.,* 319(3):1144-1152, 2006.
Lee et al., *Glia.,* 55(7):712-22, 2007.
Lencz et al., *Mol. Psychiatry,* 12(6):572-80, 2007.
Liu et al., *FASEB J.,* 20(2):207-216, 2006.
*March's Advanced Organic Chemistry: Reactions, Mechanisms, and Structure,* 2007.
McIver et al., *Pain,* 120(1-2):161-9, 2005.
Morris et al., *J. Mol. Med.,* 80(2):96-104, 2002.
Morse and Choi, *Am. J. Respir. Crit. Care Med.,* 172(6):660-670, 2005.

Morse and Choi, *Am. J. Respir. Crit. Care Med.*, 27(1):8-16, 2002.
Nath et al., *Neurology*, 66(1):149-150, 2006.
Nguyen et al., *J. Biol Chem.*, 284(20):13291-5, 2009.
Nichols, *Drug News Perspect.*, 17(2):99-104, 2004.
Pall, *Med. Hypoth.*, 69:821-825, 2007.
Rajakariar et al., *Proc. Natl. Acad. Sci. USA*, 104(52):20979-84, 2007.
Ross et al., *Am. J. Clin. Pathol.*, 120(Suppl):S53-71, 2003.
Ross et al., *Expert Rev. Mol. Diagn.*, 3(5):573-585, 2003.
Ruster et al., *Scand. J. Rheumatol.*, 34(6):460-3, 2005.
Sacerdoti et al., *Curr Neurovasc Res.* 2(2):103-111, 2005.
Salvemini et al., *J. Clin. Invest.*, 93(5):1940-1947, 1994.
Sarchielli et al., *Cephalalgia*, 26(9):1071-1079, 2006.
Satoh et al., *Proc. Natl. Acad. Sci. USA*, 103(3):768-773, 2006.
Schulz et al., *Antioxid. Redox. Sig.*, 10:115, 2008.
Shin et al., *Eur. J. Pharmacol.*, 620(1-3):138-144, 2009.
Shoelson et al., *J. Clin. Invest.*, 116(7):1793-1801, 2006.
Strejan et al., *J. Neuroimmunol.*, 7:27, 1984.
Szabo et al., *Nature Rev. Drug Disc.*, 6:662-680, 2007.
Takahashi et al., *Cancer Res.*, 57:1233-1237, 1997.
Tamir and Tannenbaum, *Biochim. Biophys. Acta.*, 1288:F31-F36, 1996.
Tumlin et al., *Am. J. Cardiol.*, 98(6A):14K-20K, 2006.
Wardle, *Nephrol. Dial. Transplant.*, 16(9):1764-8, 2001.
Yates et al., *Cancer Res.*, 66(4):2488-94, 2006.
Yates et al., *Carcinogenesis*, 30(6):1024-1031, 2009.
Yoh et al., *Kidney Int.*, 60(4):1343-1353, 2001.
Zhang et al., *Cell*, 135(1):61-73, 2008.
Zhou et al., *Am. J. Pathol.*, 166(1):27-37, 2005.
Zhou et al., *Cancer Sci.*, 98:882-889, 2007.
Zingarelli et al., *J. Immunol.*, 171(12):6827-6837, 2003.

The invention claimed is:

1. A method of reducing the weight of a human patient that is overweight, comprising administering to the human patient a pharmaceutical composition, comprising an excipient and a compound of the formula:

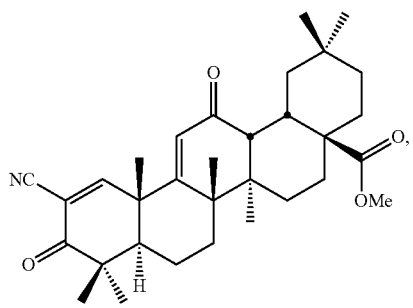

wherein administration of the pharmaceutical composition reduces the patient's weight, and wherein the patient does not have diabetes, chronic kidney disease (CKD) or cancer.

2. The method of claim 1, wherein the compound is administered in a daily dose from 5 mg to 50 mg.

3. The method of claim 2, wherein the daily dose is about 10 mg.

4. The method of claim 2, wherein the daily dose is about 20 mg.

5. The method of claim 2, wherein the daily dose is about 40 mg.

6. The method of claim 1, wherein at least a portion of the compound is present as an amorphous form having an X-ray diffraction pattern (CuKα) with a halo peak at approximately 13.5°2θ, substantially as shown in FIG. 1C, and a $T_g$ from about 120° C. to about 135° C.

7. The method of claim 1, wherein the excipient is a methacrylic acid-ethyl acrylate copolymer.

8. The method of claim 7, wherein the compound is administered in a daily dose from 5 mg to 50 mg.

9. The method of claim 8, wherein the daily dose is about 10 mg.

10. The method of claim 8, wherein the daily dose is about 20 mg.

11. The method of claim 8, wherein the daily dose is about 40 mg.

12. The method of claim 7, wherein the monomer ratio in the methacrylic acid-ethyl acrylate copolymer is about 1:1.

13. The method of any one of claim 1, wherein the compound and the excipient are formulated as a solid dispersion.

14. The method of claim 13, wherein the compound is administered in a daily dose from 5 mg to 50 mg.

15. The method of claim 14, wherein the daily dose is about 10 mg.

16. The method of claim 14, wherein the daily dose is about 20 mg.

17. The method of claim 14, wherein the daily dose is about 40 mg.

18. The method of claim 1, wherein the patient does not have insulin resistance or glucose intolerance.

19. The method of claim 1, wherein the patient does not have cardiovascular disease.

20. The method of claim 1, wherein the patient does not have fatty liver disease.

21. The method of claim 1, wherein the patient does not have metabolic syndrome.

22. The method of claim 1, wherein the patient does not have autoimmune disease, respiratory disease, neurodegenerative disease, liver disease, or infectious disease.

23. The method of claim 1, wherein the patient is obese.

* * * * *

UNITED STATES PATENT AND TRADEMARK OFFICE
CERTIFICATE OF CORRECTION

PATENT NO. : 10,105,372 B2
APPLICATION NO. : 13/085338
DATED : October 23, 2018
INVENTOR(S) : Colin J. Meyer et al.

Page 1 of 1

It is certified that error appears in the above-identified patent and that said Letters Patent is hereby corrected as shown below:

In Claim 6, Column 70, Line 15, delete the word "substantially".

Signed and Sealed this
Fourth Day of December, 2018

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,105,372 B2 |
| APPLICATION NO. | : 13/085338 |
| DATED | : October 23, 2018 |
| INVENTOR(S) | : Meyer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this
Seventh Day of February, 2023

Katherine Kelly Vidal
*Director of the United States Patent and Trademark Office*